(12) United States Patent
Heald et al.

(10) Patent No.: US 8,841,462 B2
(45) Date of Patent: Sep. 23, 2014

(54) BICYCLIC HETEROCYCLES AS MEK KINASE INHIBITORS

(76) Inventors: Robert A. Heald, Harlow Essex (GB); Philip Jackson, Harlow Essex (GB); Joseph P. Lyssikatos, Piedmont, CA (US); Stephen Price, Harlow Essex (GB); Pascal Pierre Alexandre Savy, Harlow Essex (GB)

( * ) Notice: Subject to any disclaimer, the term of this patent is extended or adjusted under 35 U.S.C. 154(b) by 421 days.

(21) Appl. No.: 12/999,003

(22) PCT Filed: Jul. 1, 2009

(86) PCT No.: PCT/US2009/049453
§ 371 (c)(1),
(2), (4) Date: Feb. 3, 2011

(87) PCT Pub. No.: WO2010/003025
PCT Pub. Date: Jan. 7, 2010

(65) Prior Publication Data
US 2011/0190257 A1 Aug. 4, 2011

Related U.S. Application Data

(60) Provisional application No. 61/077,426, filed on Jul. 1, 2008.

(51) Int. Cl.
| C07D 275/04 | (2006.01) |
| C07D 231/56 | (2006.01) |
| C07D 513/04 | (2006.01) |
| C07D 471/04 | (2006.01) |
| A61K 31/437 | (2006.01) |
| A61K 31/428 | (2006.01) |
| A61K 31/416 | (2006.01) |

(52) U.S. Cl.
USPC ........ 548/207; 548/361.1; 546/120; 546/114; 514/301; 514/303; 514/373; 514/403

(58) Field of Classification Search
USPC ............................. 546/120; 548/207, 361.1
See application file for complete search history.

(56) References Cited

U.S. PATENT DOCUMENTS

| 3,736,326 A | 5/1973 | Denzel |
| 3,780,047 A * | 12/1973 | Denzel et al. ............... 540/555 |
| 4,012,373 A | 3/1977 | Denzel et al. |
| 4,621,089 A | 11/1986 | Ward et al. |
| 2005/0049276 A1 | 3/2005 | Kaufman et al. |
| 2005/0153942 A1 | 7/2005 | Wallace et al. |
| 2006/0030610 A1 | 2/2006 | Koch et al. |

FOREIGN PATENT DOCUMENTS

| DE | 2123318 A1 | 12/1971 |
| GB | 1319565 A | 4/1971 |
| JP | 2002 020386 A | 1/2002 |
| WO | WO 02/06213 A2 | 1/2002 |
| WO | WO 03/077855 A1 | 9/2003 |
| WO | WO 03/077914 A1 | 9/2003 |
| WO | WO 2004/022556 A1 | 3/2004 |
| WO | WO 2005/005416 A1 | 1/2005 |
| WO | WO 2005/005417 A1 | 1/2005 |
| WO | WO 2005/013996 A2 | 2/2005 |
| WO | WO 2005/023759 A2 | 3/2005 |
| WO | 2005/051906 | 6/2005 |
| WO | WO 2005/051300 A1 | 6/2005 |
| WO | WO 2005/054176 A1 | 6/2005 |
| WO | WO 2005/058858 A1 | 6/2005 |
| WO | WO 2005/061476 A2 | 7/2005 |
| WO | WO 2005/063296 A2 | 7/2005 |
| WO | WO 2007/027855 A2 | 3/2007 |
| WO | WO 2007/044515 A1 | 4/2007 |
| WO | WO 2008/028141 A2 | 3/2008 |

OTHER PUBLICATIONS (International Search Report on Patentability for International Patent Application No. PCT/US2009/049453).
(Database Beilstein [online], Beilstein Institute for Organic Chemistry, Frankfurt-Main., DE; Database Accession No. 10461885 (BRN), Others Acc. No. 10461887, 10462248 (BRNs) abstract & J. Chem. Res. Synopsis 7:437-439 (2006)).
De Mello et al., "Antileishmanial pyrazolopyridine derivatives: synthesis and structure-activity relationship analysis" *J. Med. Chem.* 47(22):5427-5432.
Denzel and Hohn, "Isoxazolopyridine" *Arch. Pharm.* 305:833-839 (1972).

(Continued)

*Primary Examiner* — Laura L. Stockton

(57) ABSTRACT

The invention relates to bicyclic heterocycles of formulae I and II with anti-cancer and/or anti-inflammatory activity and more specifically with MEK kinase inhibitory activity. The invention provides compositions and methods useful for inhibiting abnormal cell growth, treating a hyperproliferative disorder, or treating an inflammatory disease in a mammal. The invention also relates to methods of using the compounds for in vitro, in situ, and in vivo diagnosis or treatment of mammalian cells, or associated pathological conditions.

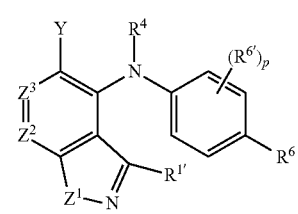

I

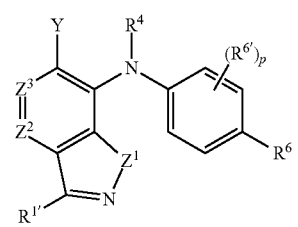

II

19 Claims, No Drawings

(56) References Cited

OTHER PUBLICATIONS

Hamblin et al., "Pyrazolopyridines as a novel structural class of potent and selective PDE4 inhibitors" *Biorg. Med. Chem. Lett.* 18(14):4237-4241 (May 17, 2008).

Hoshino et al., "Constitutive activation of the 41-/43-kDa mitogen-activated protein kinase signaling pathway in human tumors" *Oncogene* 18:813-822 (1999).

Lewis et al., "Signal transduction through MAP kinase cascades" *Adv Cancer Res.* 74:49-139 (1998).

Ochiai et al., "New orally active PDE4 inhibitors with therapeutic potential" *Bioorg. Med. Chem.* 12:4089-4100 (2004).

Ochiai et al., "New orally active PDE4 inhibitors with therapeutic potential" *Bioorg. Med. Chem. Lett.* 14:29-32 (2004).

Ochiai, "Discovery of new orally active phosphodiesterase (PDE4) inhibitors" *Chem. Pharm. Bull.* 52(9):1098-1104 (2004).

Price, B., "Putative allosteric MEK1 and MEK2 inhibitors" *Expert Opin. Ther. Patents* 18(6):603-627 (2008).

Sebolt-Leopold et al., "Blockade of the MAP kinase pathway suppresses growth of colon tumors in vivo" *Nature Medicine* 5(7):810-816 (Jul. 1999).

\* cited by examiner

BICYCLIC HETEROCYCLES AS MEK KINASE INHIBITORS

This application is made under 35 US §371 based on International Application PCT/US2009/049453 filed on Jul. 1, 2009, and claims the benefit of U.S. Provisional application No. 61/077,426, filed Jul. 1, 2008, both of which are incorporated herein by reference in their entirety.

BACKGROUND OF THE INVENTION

The invention relates to bicyclic heterocycles of formulae I and II with anti-cancer activity and more specifically with MEK kinase inhibitory activity. The invention provides compositions and methods useful for inhibiting abnormal cell growth, treating hyperproliferative disorders, or treating inflammatory diseases in a mammal. The invention also relates to methods of using the compounds for in vitro, in situ, and in vivo diagnosis or treatment of mammalian cells, or associated pathological conditions.

In the quest to understand how Ras transmits extracellular growth signals, the MAP (mitogen-activated protein) kinase (MAPK) pathway has emerged as the crucial route between membrane-bound Ras and the nucleus. The MAPK pathway encompasses a cascade of phosphorylation events involving three key kinases, namely Raf, MEK (MAP kinase kinase) and ERK (MAP kinase). Active GTP-bound Ras results in the activation and indirect phosphorylation of Raf kinase. Raf then phosphorylates MEK1 and 2 on two serine residues (S218 and S222 for MEK1 and S222 and S226 for MEK2) (Ahn et al., *Methods in Enzymology* 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn et al., *Methods in Enzymology* 2001, 332, 417-431). Phosphorylated ERK dimerizes and then translocates to the nucleus where it accumulates (Khokhlatchev et al., *Cell* 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell* 2000, 6, 1343-1354). Overall, treatment of cells with growth factors leads to the activation of ERK1 and 2 which results in proliferation and, in some cases, differentiation (Lewis et al., *Adv. Cancer Res.* 1998, 74, 49-139).

There has been strong evidence that genetic mutations and/or overexpression of protein kinases involved in the MAP kinase pathway lead to uncontrolled cell proliferation and, eventually, tumor formation, in proliferative diseases. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., *Science* 1993, 260, 1834-1837). Recently, bRaf mutations have been identified in more than 60% of malignant melanoma (Davies, H. et al., *Nature* 2002, 417, 949-954). These mutations in bRaf result in a constitutively active MAP kinase cascade. Studies of primary tumor samples and cell lines have also shown constitutive or over-activation of the MAP kinase pathway in cancers of pancreas, colon, lung, ovary and kidney (Hoshino, R. et al., *Oncogene* 1999, 18, 813-822).

MEK has emerged as an attractive therapeutic target in the MAP kinase cascade pathway. MEK, downstream of Ras and Raf, is highly specific for the phosphorylation of MAP kinase; in fact, the only known substrates for MEK phosphorylation are the MAP kinases, ERK1 and 2. Inhibition of MEK has been shown to have potential therapeutic benefit in several studies. For example, small molecule MEK inhibitors have been shown to inhibit human tumor growth in nude mouse xenografts, (Sebolt-Leopold et al., *Nature-Medicine* 1999, 5 (7), 810-816); Trachet et al., AACR Apr. 6-10, 2002, Poster #5426; Tecle, H. IBC 2.sup.nd International Conference of Protein Kinases, Sep. 9-10, 2002), block static allodynia in animals (WO 01/05390 published Jan. 25, 2001) and inhibit growth of acute myeloid leukemia cells (Milella et al., *J Clin Invest* 2001, 108 (6), 851-859).

Several small molecule MEK inhibitors have also been discussed in, for example, WO02/06213, WO 03/077855 and WO03/077914. There still exists a need for new MEK inhibitors as effective and safe therapeutics for treating a variety of proliferative disease states, such as conditions related to the hyperactivity of MEK, as well as diseases modulated by the MEK cascade.

SUMMARY OF THE INVENTION

The invention relates generally to bicyclic heterocycles of formulae I and II (and/or solvates, hydrates and/or salts thereof) with anti-cancer and/or anti-inflammatory activity, and more specifically with MEK kinase inhibitory activity. Certain hyperproliferative and inflammatory disorders are characterized by the modulation of MEK kinase function, for example by mutations or overexpression of the proteins. Accordingly, the compounds of the invention and compositions thereof are useful in the treatment of hyperproliferative disorders such as cancer and/or inflammatory diseases such as rheumatoid arthritis.

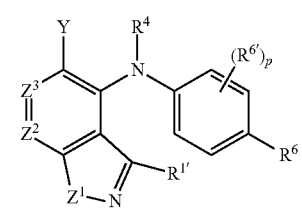

I

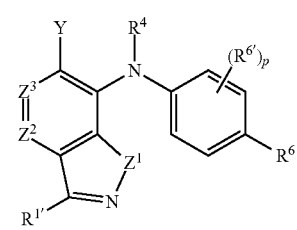

II wherein:
$Z^1$ is $NR^1$, S or O;
$R^1$ is H, $C_1$-$C_3$ alkyl, $CF_3$, $CHF_2$, or cyclopropyl;
$R^{1'}$ is H, $C_1$-$C_3$ alkyl, cyclopropyl, halo, $CF_3$, $CHF_2$, CN, $NR^A R^A$ or $OR^B$;
each $R^A$ is independently H or $C_1$-$C_3$ alkyl;
$R^B$ is H, or $C_1$-$C_3$ alkyl optionally substituted with one or more halo;
$Z^2$ is $CR^2$ or N;

$Z^3$ is $CR^3$ or N; provided that $Z^2$ and $Z^3$ are not both N at the same time;

$R^2$ and $R^3$ are independently selected from H, halo, CN, $CF_3$, $-OCF_3$, $-NO_2$, $-(CR^{14}R^{15})_nC(=Y')R^{11}$, $-(CR^{14}R^{15})_nC(=Y')OR^{11}$, $-(CR^{14}R^{15})_nC(=Y')NR^{11}R^{12}$, $-(CR^{14}R^{15})_nNR^{11}R^{12}$, $-(CR^{14}R^{15})_nOR^{11}$, $-(CR^{14}R^{15})_nSR^{11}$, $-(CR^{14}R^{15})_nNR^{12}C(=Y')R^{11}$, $-(CR^{14}R^{15})_nNR^{12}C(=Y')OR^{11}$, $-(CR^{14}R^{15})_nNR^{13}C(=Y')NR^{11}R^{12}$, $-(CR^{14}R^{15})_nNR^{12}SO_2R^{11}$, $-(CR^{14}R^{15})_nOC(=Y')R^{11}$, $-(CR^{14}R^{15})_nOC(=Y')OR^{11}$, $-(CR^{14}R^{15})_nOC(=Y')NR^{11}R^{12}$, $-(CR^{14}R^{15})_nOS(O)_2(OR^{11})$, $-(CR^{14}R^{15})_nOP(=Y')(OR^{11})(OR^{12})$, $-(CR^{14}R^{15})_nOP(OR^{11})(OR^{12})$, $-(CR^{14}R^{15})_nS(O)R^{11}$, $-(CR^{14}R^{15})_nS(O)_2R^{11}$, $-(CR^{14}R^{15})_nS(O)_2NR^{11}R^{12}$, $-(CR^{14}R^{15})_nS(O)(OR^{11})$, $-(CR^{14}R^{15})_nS(O)_2(OR^{11})$, $-(CR^{14}R^{15})_nSC(=Y')R^{11}$, $-(CR^{14}R^{15})_nSC(=Y')OR^{11}$, $-(CR^{14}R^{15})_nSC(=Y')NR^{11}R^{12}$, $C_1$-$C_{12}$ alkyl, $C_2$-$C_8$ alkenyl, $C_2$-$C_8$ alkynyl, carbocyclyl, heterocyclyl, aryl, and heteroaryl;

$R^4$ is H, $C_1$-$C_6$ alkyl or $C_3$-$C_4$ carbocyclyl;

Y is W—C(O)— or W';

W is

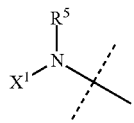

or

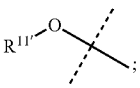

$R^5$ is H or $C_1$-$C_{12}$ alkyl;

$X^1$ is selected from $R^{11'}$ and $-OR^{11'}$; when $X^1$ is $R^{11'}$, $X^1$ is optionally taken together with $R^5$ and the nitrogen atom to which they are bound to form a 4-7 membered saturated or unsaturated ring having 0-2 additional heteroatoms selected from O, S and N, wherein said ring is optionally substituted with one or more groups selected from halo, CN, $CF_3$, $-OCF_3$, $-NO_2$, oxo, $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_n-SR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$;

each $R^{11'}$ is independently H, $C_1$-$C_{12}$ alkyl, $C_2$-$C_8$ alkenyl, $C_2$-$C_8$ alkynyl, carbocyclyl, heterocyclyl, aryl, or heteroaryl;

$R^{11}$, $R^{12}$ and $R^{13}$ are independently H, $C_1$-$C_{12}$ alkyl, $C_2$-$C_8$ alkenyl, $C_2$-$C_8$ alkynyl, carbocyclyl, heterocyclyl, aryl, or heteroaryl, or $R^{11}$ and $R^{12}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, $CF_3$, $-OCF_3$, $-NO_2$, $C_1$-$C_6$ alkyl, $-OH$, $-SH$, $-O(C_1$-$C_6$ alkyl), $-S(C_1$-$C_6$ alkyl), $-NH_2$, $-NH(C_1$-$C_6$ alkyl), $-N(C_1$-$C_6$ alkyl)$_2$, $-SO_2(C_1$-$C_6$ alkyl), $-CO_2H$, $-CH_2(C_1$-$C_6$ alkyl), $-C(O)NH_2$, $-C(O)NH(C_1$-$C_6$ alkyl), $-C(O)N(C_1$-$C_6$ alkyl)$_2$, $-N(C_1$-$C_6$ alkyl)C(O)(C_1$-$C_6$ alkyl), $-NHC(O)(C_1$-$C_6$ alkyl), $-NHSO_2(C_1$-$C_6$ alkyl), $-N(C_1$-$C_6$ alkyl)SO_2(C_1$-$C_6$ alkyl), $-SO_2NH_2$, $-SO_2NH(C_1$-$C_6$ alkyl), $-SO_2N(C_1$-$C_6$ alkyl)$_2$, $-OC(O)NH_2$, $-OC(O)NH(C_1$-$C_6$ alkyl), $-OC(O)N(C_1$-$C_6$ alkyl)$_2$, $-OC(O)O(C_1$-$C_6$ alkyl), $-NHC(O)NH(C_1$-$C_6$ alkyl), $-NHC(O)N(C_1$-$C_6$ alkyl)$_2$, $-N(C_1$-$C_6$ alkyl)C(O)NH(C_1$-$C_6$ alkyl), $-N(C_1$-$C_6$ alkyl)C(O)N(C_1$-$C_6$ alkyl)$_2$, $-NHC(O)NH(C_1$-$C_6$ alkyl), $-NHC(O)N(C_1$-$C_6$ alkyl)$_2$, $-NHC(O)O(C_1$-$C_6$ alkyl), and $-N(C_1$-$C_6$ alkyl)C(O)O(C_1$-$C_6$ alkyl);

$R^{14}$ and $R^{15}$ are independently selected from H, $C_1$-$C_{12}$ alkyl, aryl, carbocyclyl, heterocyclyl, and heteroaryl;

W' is

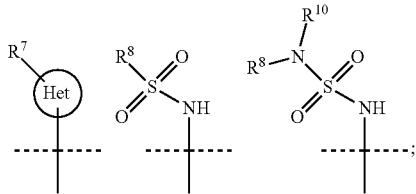

wherein

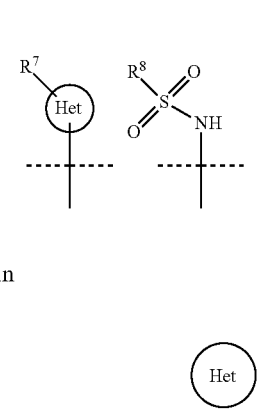

is

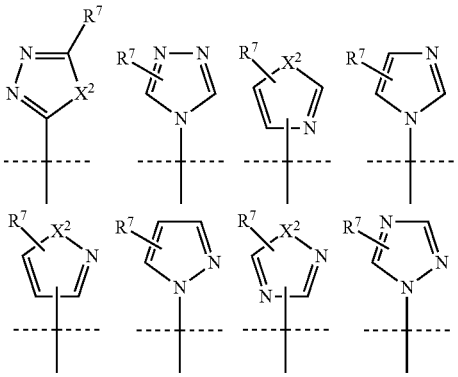

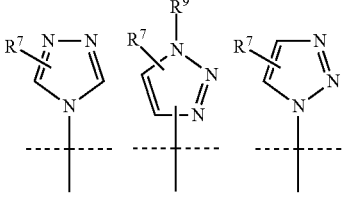

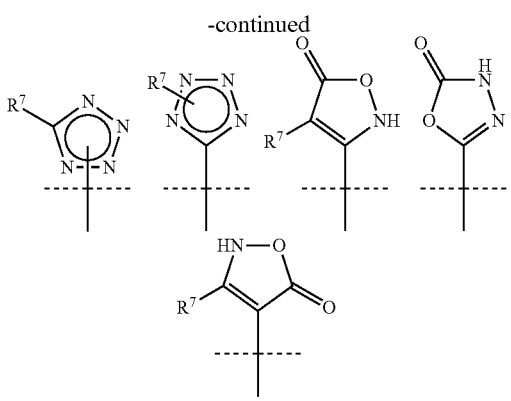

$X^2$ is O, S, or $NR^9$;

$R^7$ is selected from H, halo, CN, $CF_3$, —$OCF_3$, —$NO_2$, —$(CR^{14}R^{15})_nC(=Y')R^{11}$, —$(CR^{14}R^{15})_nC(=Y')OR^{11}$, —$(CR^{14}R^{15})_nC(=Y')NR^{11}R^{12}$, —$(CR^{14}R^{15})_nNR^{11}R^{12}$, —$(CR^{14}R^{15})_nOR^{11}$, —$(CR^{14}R^{15})_nSR^{11}$, —$(CR^{14}R^{15})_nNR^{12}C(=Y')R^{11}$, —$(CR^{14}R^{15})_nNR^{12}C(=Y')OR^{11}$, —$(CR^{14}R^{15})_nNR^{13}C(=Y')NR^{11}R^{12}$, —$(CR^{14}R^{15})_nNR^{12}SO_2R^{11}$, —$(CR^{14}R^{15})_nOC(=Y')R^{11}$, —$(CR^{14}R^{15})_nOC(=Y')OR^{11}$, —$(CR^{14}R^{15})_nOC(=Y')NR^{11}R^{12}$, —$(CR^{14}R^{15})_nOS(O)_2(OR^{11})$, —$(CR^{14}R^{15})_nOP(=Y')(OR^{11})(OR^{12})$, —$(CR^{14}R^{15})_nOP(OR^{11})(OR^{12})$, —$(CR^{14}R^{15})_nS(O)R^{11}$, —$(CR^{14}R^{15})_nS(O)_2R^{11}$, —$(CR^{14}R^{15})_nS(O)_2NR^{11}R^{12}$, —$(CR^{14}R^{15})_nS(O)(OR^{11})$, —$(CR^{14}R^{15})_nS(O)_2(OR^{11})$, —$(CR^{14}R^{15})_nSC(=Y')R^{11}$, —$(CR^{14}R^{15})_nSC(=Y')OR^{11}$, —$(CR^{14}R^{15})_nSC(=Y')NR^{11}R^{12}$, $C_1-C_{12}$ alkyl, $C_2-C_8$ alkenyl, $C_2-C_8$ alkynyl, carbocyclyl, heterocyclyl, aryl, and heteroaryl;

$R^8$ is selected from $C_1-C_{12}$ alkyl, aryl, carbocyclyl, heterocyclyl, and heteroaryl;

$R^9$ is selected from H, —$(CR^{14}R^{15})_nC(=Y')R^{11}$, —$(CR^{14}R^{15})_nC(=Y')OR^{11}$, —$(CR^{14}R^{15})_nC(=Y')NR^{11}R^{12}$, —$(CR^{14}R^{15})_qNR^{11}R^{12}$, —$(CR^{14}R^{15})_qOR^{11}$, —$(CR^{14}R^{15})_qSR^{11}$, —$(CR^{14}R^{15})_qNR^{12}C(=Y')R^{11}$, —$(CR^{14}R^{15})_qNR^{12}C(=Y')OR^{11}$, —$(CR^{14}R^{15})_qNR^{13}C(=Y')NR^{11}R^{12}$, —$(CR^{14}R^{15})_qNR^{12}SO_2R^{11}$, —$(CR^{14}R^{15})_qOC(=Y')R^{11}$, —$(CR^{14}R^{15})_qOC(=Y')OR^{11}$, —$(CR^{14}R^{15})_qOC(=Y')NR^{11}R^{12}$, —$(CR^{14}R^{15})_qOS(O)_2(OR^{11})$, —$(CR^{14}R^{15})_qOP(=Y')(OR^{11})(OR^{12})$, —$(CR^{14}R^{15})_qOP(OR^{11})(OR^{12})$, —$(CR^{14}R^{15})_nS(O)R^{11}$, —$(CR^{14}R^{15})_nS(O)_2R^{11}$, —$(CR^{14}R^{15})_nS(O)_2NR^{11}R^{12}$, $C_1-C_{12}$ alkyl, $C_2-C_8$ alkenyl, $C_2-C_8$ alkynyl, carbocyclyl, heterocyclyl, aryl, and heteroaryl;

$R^{10}$ is H, $C_1-C_6$ alkyl or $C_3-C_4$ carbocyclyl;

$R^6$ is H, halo, $C_1-C_6$ alkyl, $C_2-C_8$ alkenyl, $C_2-C_8$ alkynyl, carbocyclyl, heteroaryl, heterocyclyl, —$OCF_3$, —$NO_2$, —$Si(C_1-C_6$ alkyl$)$, —$(CR^{19}R^{20})$—$NR^{16}R^{17}$, —$(CR^{19}R^{20})_nOR^{16}$, or —$(CR^{19}R^{20})_nSR^{16}$;

each $R^{6'}$ is independently H, halo, $C_1-C_6$ alkyl, $C_2-C_8$ alkenyl, $C_2-C_8$ alkynyl, carbocyclyl, heterocyclyl, aryl, heteroaryl, $CF_3$, —$OCF_3$, —$NO_2$, —$Si(C_1-C_6$ alkyl$)$, —$(CR^{19}R^{20})_nNR^{16}R^{17}$, —$(CR^{19}R^{20})_nOR^{16}$, or —$(CR^{19}R^{20})_nSR^{16}$; provided that $R^6$ and $R^{6'}$ are not both H at the same time;

p is 0, 1, 2 or 3;

n is 0, 1, 2 or 3;

q is 2 or 3;

wherein each said alkyl, alkenyl, alkynyl, carbocyclyl, heterocyclyl, aryl and heteroaryl of $R^2$, $R^3$, $R^4$, $R^5$, $R^6$, $R^{6'}$, $R^7$, $R^8$, $R^9$, $R^{10}$, $R^{11}$, $R^{12}$, $R^{13}$, $R^{14}$ and $R^{15}$ is independently optionally substituted with one or more groups independently selected from halo, CN, $CF_3$, —$OCF_3$, —$NO_2$, oxo, —$Si(C_1-C_6$ alkyl$)$, —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_nSR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$;

each $R^{16}$, $R^{17}$ and $R^{18}$ is independently H, $C_1-C_{12}$ alkyl, $C_2-C_8$ alkenyl, $C_2-C_8$ alkynyl, carbocyclyl, heterocyclyl, aryl, or heteroaryl, wherein said alkyl, alkenyl, alkynyl, carbocyclyl, heterocyclyl, aryl, or heteroaryl is optionally substituted with one or more groups selected from halo, CN, —$OCF_3$, $CF_3$, —$NO_2$, $C_1-C_6$ alkyl, —OH, —SH, —$O(C_1-C_6$ alkyl$)$, —$S(C_1-C_6$ alkyl$)$, —$NH_2$, —$NH(C_1-C_6$ alkyl$)$, —$N(C_1-C_6$ alkyl$)_2$, $SO_2(C_1-C_6$ alkyl$)$, —$CO_2H$, —$CO_2(C_1-C_6$ alkyl$)$, —$C(O)NH_2$, —$C(O)NH(C_1-C_6$ alkyl$)$, —$C(O)N(C_1-C_6$ alkyl$)_2$, —$N(C_1-C_6$ alkyl$)C(O)(C_1-C_6$ alkyl$)$, —$NHSO_2(C_1-C_6$ alkyl$)$, —$NHC(O)(C_1-C_6$ alkyl$)$, —$N(C_1-C_6$ alkyl$)SO_2(C_1-C_6$ alkyl$)$, —$SO_2NH_2$, —$SO_2NH(C_1-C_6$ alkyl$)$, —$SO_2N(C_1-C_6$ alkyl$)_2$, —$OC(O)NH_2$, —$OC(O)NH(C_1-C_6$ alkyl$)$, —$OC(O)N(C_1-C_6$ alkyl$)_2$, —$OC(O)O(C_1-C_6$ alkyl$)$, —$NHC(O)NH(C_1-C_6$ alkyl$)$, —$NHC(O)N(C_1-C_6$ alkyl$)_2$, —$N(C_1-C_6$ alkyl$)C(O)NH(C_1-C_6$ alkyl$)$, —$N(C_1-C_6$ alkyl$)C(O)N(C_1-C_6$ alkyl$)_2$, —$NHC(O)NH(C_1-C_6$ alkyl$)$, —$NHC(O)N(C_1-C_6$ alkyl$)_2$, —$NHC(O)O(C_1-C_6$ alkyl$)$, and —$N(C_1-C_6$ alkyl$)C(O)O(C_1-C_6$ alkyl$)$;

or $R^{16}$ and $R^{17}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, —$OCF_3$, $CF_3$, —$NO_2$, $C_1-C_6$ alkyl, —OH, —SH, —$O(C_1-C_6$ alkyl$)$, —$S(C_1-C_6$ alkyl$)$, —$NH_2$, —$NH(C_1-C_6$ alkyl$)$, —$N(C_1-C_6$ alkyl$)_2$, —$SO_2(C_1-C_6$ alkyl$)$, —$CO_2H$, —$CO_2(C_1-C_6$ alkyl$)$, —$C(O)NH_2$, —$C(O)NH(C_1-C_6$ alkyl$)$, —$C(O)N(C_1-C_6$ alkyl$)_2$, —$N(C_1-C_6$ alkyl$)C(O)(C_1-C_6$ alkyl$)$, —$NHC(O)(C_1-C_6$ alkyl$)$, —$NHSO_2(C_1-C_6$ alkyl$)$, —$N(C_1-C_6$ alkyl$)SO_2(C_1-C_6$ alkyl$)$, —$SO_2NH_2$, —$SO_2NH(C_1-C_6$ alkyl$)$, —$SO_2N(C_1-C_6$ alkyl$)_2$, —$OC(O)NH_2$, —$OC(O)NH(C_1-C_6$ alkyl$)$, —$OC(O)N(C_1-C_6$ alkyl$)_2$, —$OC(O)O(C_1-C_6$ alkyl$)$, —$NHC(O)NH(C_1-C_6$ alkyl$)$, —$NHC(O)N(C_1-C_6$ alkyl$)_2$, —$N(C_1-C_6$ alkyl$)C(O)NH(C_1-C_6$ alkyl$)$, —$N(C_1-C_6$ alkyl$)C(O)N(C_1-C_6$ alkyl$)_2$, —$NHC(O)NH(C_1-C_6$ alkyl$)$, —$NHC(O)N(C_1-C_6$ alkyl$)_2$, —$NHC(O)O(C_1-C_6$ alkyl$)$, and —$N(C_1-C_6$ alkyl$)C(O)O(C_1-C_6$ alkyl$)$;

$R^{19}$ and $R^{20}$ are independently selected from H, $C_1-C_{12}$ alkyl, —$(CH_2)_n$-aryl, —$(CH_2)_n$-carbocyclyl, —$(CH_2)_n$-heterocyclyl, and —$(CH_2)_n$-heteroaryl;

$R^{21}$ is $C_1-C_{12}$ alkyl, $C_2-C_8$ alkenyl, $C_2-C_8$ alkynyl, carbocyclyl, heterocyclyl, aryl, or heteroaryl, wherein each member of $R^{21}$ is optionally substituted with one or more groups selected from halo, oxo, CN, —$OCF_3$, $CF_3$, —$NO_2$, $C_1-C_6$ alkyl, —OH, —SH, —$O(C_1-C_6$ alkyl$)$, —$S(C_1-C_6$ alkyl$)$, —$NH_2$, —$NH(C_1-C_6$ alkyl$)$, —$N(C_1-C_6$ alkyl$)_2$, —$SO_2(C_1-C_6$ alkyl$)$, —$CO_2H$, —$CO_2(C_1-C_6$ alkyl$)$, —$C(O)NH_2$, —$C(O)NH(C_1-C_6$ alkyl$)$, —$C(O)N(C_1-C_6$ alkyl$)_2$, —$N(C_1-C_6$ alkyl$)C(O)(C_1-C_6$ alkyl$)$, —$NHC(O)(C_1-C_6$ alkyl$)$, —$NHSO_2(C_1-C_6$ alkyl$)$, —$N(C_1-C_6$ alkyl$)SO_2(C_1-$ $C_6$ alkyl), $-SO_2NH_2$, $-SO_2NH(C_1-C_6$ alkyl), $-SO_2N(C_1-C_6$ alkyl)$_2$, $-OC(O)NH_2$, $-OC(O)NH(C_1-C_6$ alkyl), $-OC(O)N(C_1-C_6$ alkyl)$_2$, $-OC(O)O(C_1-C_6$ alkyl), $-NHC(O)NH(C_1-C_6$ alkyl), $-NHC(O)N(C_1-C_6$ alkyl)$_2$, $-N(C_1-C_6$ alkyl)$C(O)NH(C_1-C_6$ alkyl), $-N(C_1-C_6$ alkyl)$C(O)N(C_1-C_6$ alkyl)$_2$, $-NHC(O)NH(C_1-C_6$ alkyl), $-NHC(O)N(C_1-C_6$ alkyl)$_2$, $-NHC(O)O(C_1-C_6$ alkyl), and $-N(C_1-C_6$ alkyl)$C(O)O(C_1-C_6$ alkyl);

each Y' is independently O, $NR^{22}$, or S; and $R^{22}$ is H or $C_1-C_{12}$ alkyl;

provided that in formula (I), (i) when $Z^1$ is $NR^1$ and $Z^2$ is N, then Y is not $CO_2NH_2$; and (ii) when $Z^1$ is $NR^1$, $Z^2$ is N, $R^{1'}$ is H, $Z^3$ is $CR^3$ wherein $R^3$ is H, $CH_3$, $CF_3$, $CHF_2$, or $CH_2F$,

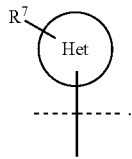

then Y is not $CO_2Et$ or

The present invention includes a composition (e.g., a pharmaceutical composition) comprising a compound of formula I or II (and/or solvates, hydrates and/or salts thereof) and a carrier (a pharmaceutically acceptable carrier). The present invention also includes a composition (e.g., a pharmaceutical composition) comprising a compound of formula I or II (and/or solvates, hydrates and/or salts thereof) and a carrier (a pharmaceutically acceptable carrier), further comprising a second chemotherapeutic and/or a second anti-inflammatory agent. The present compositions are useful for inhibiting abnormal cell growth or treating a hyperproliferative disorder in a mammal (e.g., human). The present compositions are also useful for treating inflammatory diseases in a mammal (e.g., human).

The present invention includes a method of inhibiting abnormal cell growth or treating a hyperproliferative disorder in a mammal (e.g., human) comprising administering to said mammal a therapeutically effective amount of a compound of formula I or II (and/or solvates and salts thereof) or a composition thereof, alone or in combination with a second chemotherapeutic agent.

The present invention includes a method of treating an inflammatory disease in a mammal (e.g., human) comprising administering to said mammal a therapeutically effective amount of a compound of formula I or II (and/or solvates and salts thereof) or a composition thereof, alone or in combination with a second anti-inflammatory agent.

The present invention includes a method of using the present compounds for in vitro, in situ, and in vivo diagnosis or treatment of mammalian cells, organisms, or associated pathological conditions.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

The term "alkyl" as used herein refers to a saturated linear or branched-chain monovalent hydrocarbon radical of one to twelve carbon atoms. Examples of alkyl groups include, but are not limited to, methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$), 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, $sp^2$ double bond, wherein the alkenyl radical includes radicals having "cis" and "trans" orientations, or alternatively, "E" and "Z" orientations. Examples include, but are not limited to, ethylenyl or vinyl ($-CH=CH_2$), allyl ($-CH_2CH=CH_2$), and the like.

The term "alkynyl" refers to a linear or branched monovalent hydrocarbon radical of two to twelve carbon atoms with at least one site of unsaturation, i.e., a carbon-carbon, sp triple bond. Examples include, but are not limited to, ethynyl ($-C\equiv CH$), propynyl (propargyl, $-CH_2C\equiv CH$), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronaphthalene, 1,2,3,4-tetrahydronaphthyl, and the like.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, and S) or a bicycle having 7 to 10 ring members (4 to 9 carbon atoms and 1 to 6 heteroatoms selected from N, O, and S), for example: a bicyclo[4,5], [5,5], [5,6], or [6,6] system. Heterocycles are described in Paquette, Leo A.; "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "halo" refers to F, Cl, Br or I. The heteroatoms present in heteroaryl or heterocyclcyl include the oxidized forms such as $N^+ \rightarrow O^-$, $S(O)$ and $S(O)_2$.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "abnormal cell growth" and "hyperproliferative disorder" are used interchangeably in this application. "Abnormal cell growth", as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, acute leukemia, as well as head/brain and neck cancer.

A "chemotherapeutic agent" is a compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LUR- TOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. Nos. 5,863,949, 5,861,510, and EP 780, 386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents that can be used in combination with the present compounds include inhibitors of PI3K (phosphoinositide-3 kinase), such as those reported in Yaguchi et al (2006) Jour. of the Nat. Cancer Inst. 98(8):545-556; U.S. Pat. Nos. 7,173,029; 7,037,915; 6,608, 056; 6,608,053; 6,838,457; 6,770,641; 6,653,320; 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.) and GDC-0941 (PI3K inhibitor, PIramed and Genenetch).

The term "inflammatory diseases" as used in this application includes, but not limited to, rheumatoid arthritis, atherosclerosis, congestive heart failure, inflammatory bowel disease (including, but not limited to, Crohn's disease and ulcerative colitis), chronic obstructive pulmonary disease in the lung, fibrotic disease in the liver and kidney, Crohn's disease, lupus, skin diseases such as psoriasis, eczema and scleroderma, osteoarthritis, multiple sclerosis, asthma, diseases and disorders related to diabetic complications, fibrotic organ failure in organs such as lung, liver, kidney, and inflammatory complications of the cardiovascular system such as acute coronary syndrome.

An "anti-inflammatory agent" is a compound useful in the treatment of inflammation. Examples of anti-inflammatory agents include injectable protein therapeutics such as Enbrel®, Remicade®, Humira® and Kineret®. Other examples of anti-inflammatory agents include non-steroidal anti-inflammatory agents (NSAIDs), such as ibuprofen or aspirin (which reduce swelling and alleviate pain); disease-modifying anti-rheumatic drugs (DMARDs) such as methotrexate; 5-aminosalicylates (sulfasalazine and the sulfa-free agents); corticosteroids; immunomodulators such as 6-mercaptoputine ("6-MP"), azathioprine ("AZA"), cyclosporines, and biological response modifiers such as Remicade® (infliximab) and Enbrel® (etanercept); fibroblast growth factors; platelet derived growth factors; enzyme blockers such as Arava® (leflunomide); and/or a cartilage protecting agent such as hyaluronic acid, glucosamine, and chondroitin.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as the MEK inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and trialkylsilyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention", "compounds of the present invention" and "compounds of formula I or II", unless otherwise indicated, include compounds of formula I or II and stereoisomers, geometric isomers, tautomers, solvates, metabolites, salts (e.g., pharmaceutically acceptable salts) and prodrugs thereof. Unless otherwise stated, structures depicted herein are also meant to include compounds that differ only in the presence of one or more isotopically enriched atoms. For example, compounds of formula I or II, wherein one or more hydrogen atoms are replaced deuterium or tritium, or one or more carbon atoms are replaced by a $^{13}$C- or $^{14}$C-enriched carbon are within the scope of this invention.

The present invention provides bicyclic heterocycles of formula I and II as described above useful as kinase inhibitors, particularly useful as MEK kinase inhibitors.

In an embodiment of the present invention, when $R^3$ is $-(CR^{14}R^{15})_nC(=O)R^{11}$, $-(CR^{14}R^{15})_nNR^{11}R^{12}$, $-(CR^{14}R^{15})_nOR^{11}$, $-(CR^{14}R^{15})_nSR^{11}$, $-(CR^{14}R^{15})_nS(O)R^{11}$, or $-(CR^{14}R^{15})_nS(O)_2R^{11}$; n is 0; and $Z^1$ is O, then said $R^{11}$ or $R^{12}$ is not aryl; when $Z^1$ is O, then $R^3$ is not $CH_2$-aryl; and all other variables are as defined in formula I.

In an embodiment of the present invention, compounds are of formula I-a (i.e., $Z^1$ is NH, and $Z^2$ and $Z^3$ are CH), I-b (i.e., $Z^1$ is NH, $Z^2$ is N and $Z^3$ is CH), I-c (i.e., $Z^1$ is NH, $Z^2$ is CH and $Z^3$ is N), I-d (i.e., $Z^1$ is S, $Z^2$ and $Z^3$ are CH), I-e (i.e., $Z^1$ is S, $Z^2$ is N and $Z^3$ is CH), I-f (i.e., $Z^1$ is S, $Z^2$ is CH and $Z^3$ is N), II-a (i.e., $Z^1$ is NH, and $Z^2$ and $Z^3$ are CH), II-b (i.e., $Z^1$ is NH, $Z^2$ is N and $Z^3$ is CH), II-c (i.e., $Z^1$ is NH, $Z^2$ is CH and $Z^3$ is N), II-d (i.e., $Z^1$ is S, $Z^2$ and $Z^3$ are CH), II-e (i.e., $Z^1$ is S, $Z^2$ is N and $Z^3$ is CH), or II-f (i.e., $Z^1$ is S, $Z^2$ is CH and $Z^3$ is N); and all other variables are as defined in formula I or II.

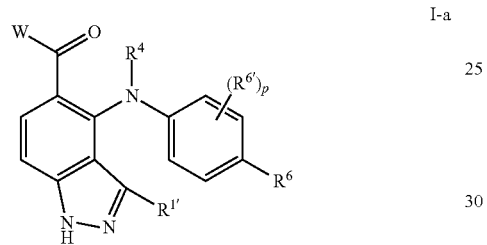

I-a

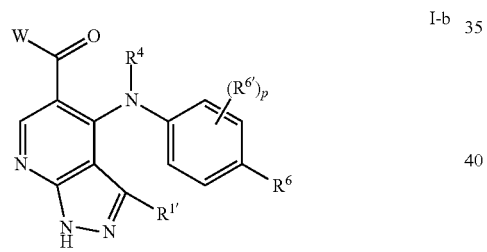

I-b

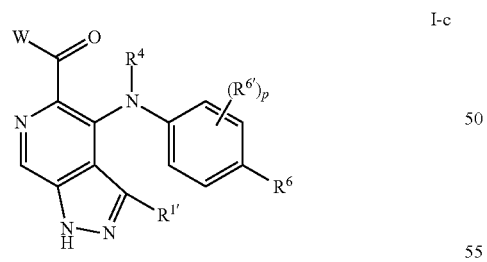

I-c

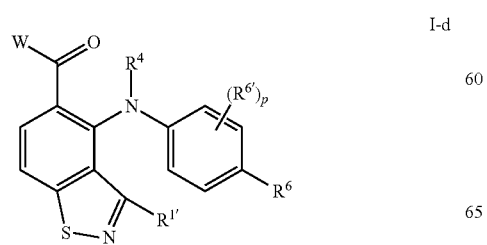

I-d

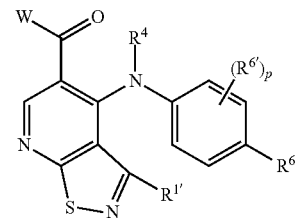

I-e

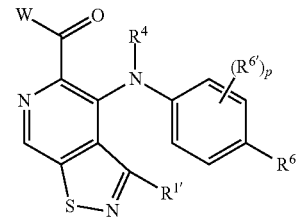

I-f

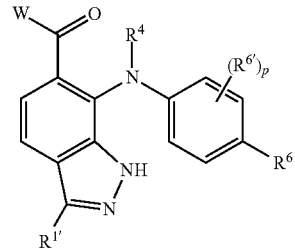

II-a

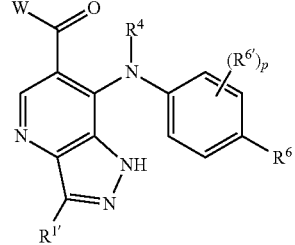

II-b

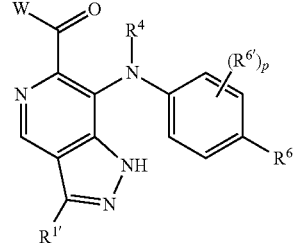

II-c

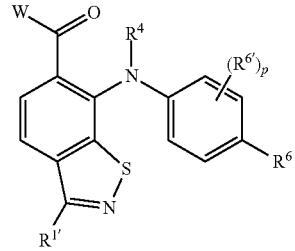

II-d

-continued

II-e

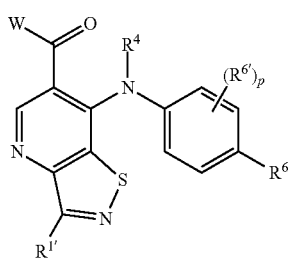

II-f

In an embodiment of the present invention, $Z^2$ is $CR^2$ and $R^2$ is H, halo, $CF_3$, or $C_1$-$C_3$ alkyl; and all other variables are as defined in formula I or II, or as defined in any one of the embodiments described above.

In another embodiment of the present invention, $Z^2$ is $CR^2$ and $R^2$ is H, methyl, $CF_3$, F, or Cl; and all other variables are as defined in formula I or II, or as defined in any one of the embodiments described above.

In another embodiment of the present invention, $Z^2$ is $CR^2$ and $R^2$ is H, F or Cl; and all other variables are as defined in formula I or II, or as defined in any one of the embodiments described above.

In another embodiment of the present invention, $Z^2$ is N; and all other variables are as defined in formula I or II, or as defined in any one of the embodiments described above.

In an embodiment of the present invention, $Z^3$ is $CR^3$ and $R^3$ is H, halo, $CF_3$, O—$C_1$-$C_3$ alkyl) or $C_1$-$C_3$ alkyl; and all other variables are as defined in formula I or II, or as defined in any one of the embodiments described above.

In another embodiment of the present invention, $Z^3$ is $CR^3$ and $R^3$ is H, methyl, $CF_3$, F, OMe, or Cl; and all other variables are as defined in formula I or II, or as defined in any one of the embodiments described above.

In another embodiment of the present invention, $Z^3$ is $CR^3$ and $R^3$ is H, F, OMe or Cl; and all other variables are as defined in formula I or II, or as defined in any one of the embodiments described above.

In another embodiment of the present invention, $Z^3$ is N; and all other variables are as defined in formula I or II, or as defined in any one of the embodiments described above.

In an embodiment of the present invention, $R^{1'}$ is H, and all other variables are as defined in formula I or II, or as defined in any one of the embodiments described above.

In another embodiment of the present invention, $Z^1$ is $NR^1$; and all other variables are as defined in formula I or II, or as defined in any one of the embodiments described above. In another embodiment, $R^1$ is H, and all other variables are as defined in formula I or II, or as defined in any one of the embodiments above.

In another embodiment of the present invention, $Z^1$ is S; and all other variables are as defined in formula I or II, or as defined in any one of the embodiments described above.

In an embodiment of the present invention, $R^4$ is H or $C_1$-$C_6$ alkyl; and all other variables are as defined in formula I or II, or as defined in any one of the embodiments above.

In another embodiment of the present invention, $R^4$ is H or methyl; and all other variables are as defined in formula I or II, or as defined in any one of the embodiments above. In another embodiment of the present invention, $R^4$ is H; and all other variables are as defined in formula I or II, or as defined in any one of the embodiments above.

In an embodiment of the present invention, $R^5$ is H or $C_1$-$C_6$ alkyl; and all other variables are as defined in formula I or II, or as defined in any one of the embodiments above.

In another embodiment of the present invention, $R^5$ is H or methyl; and all other variables are as defined in formula I or II, or as defined in any one of the embodiments above.

In another embodiment of the present invention, $R^5$ is H; and all other variables are as defined in formula I or II, or as defined in any one of the embodiments above.

In an embodiment of the present invention, $X^1$ is $OR^{11'}$ wherein $R^{11'}$ is H or $C_1$-$C_{12}$ alkyl (e.g., $C_1$-$C_6$ alkyl) substituted with one or more groups independently selected from halo, CN, $CF_3$, —$OCF_3$, —$NO_2$, oxo, —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_nSR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y)OR^{16}$, —$(CR^{19}R^{20})_nSC(=Y')NR^{16}R^{17}$, and $R^{21}$; and all other variables are as defined in formula I or II, or as defined in any one of the embodiments above.

In another embodiment of the present invention, $X^1$ is $OR^{11'}$ wherein $R^{11'}$ is heterocyclyl (e.g., 4- to 6-membered heterocyclyl) optionally substituted with one or more groups independently selected from halo, CN, $CF_3$, —$OCF_3$, —$NO_2$, oxo, —$(CR^{19}R^{20})_nC(=Y')OR^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_nSR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in formula I or II, or as defined in any one of the embodiments above.

In another embodiment of the present invention, $X^1$ is $OR^{11'}$ wherein $R^{11'}$ is 4- to 6-membered heterocyclyl having 1 nitrogen ring atom wherein said heterocyclyl is optionally substituted with one or more groups independently selected from halo, CN, $CF_3$, —$OCF_3$, —$NO_2$, oxo, —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_nSR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}$ $R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in formula I or II, or as defined in any one of the embodiments above.

In another embodiment of the present invention, $X^1$ is:

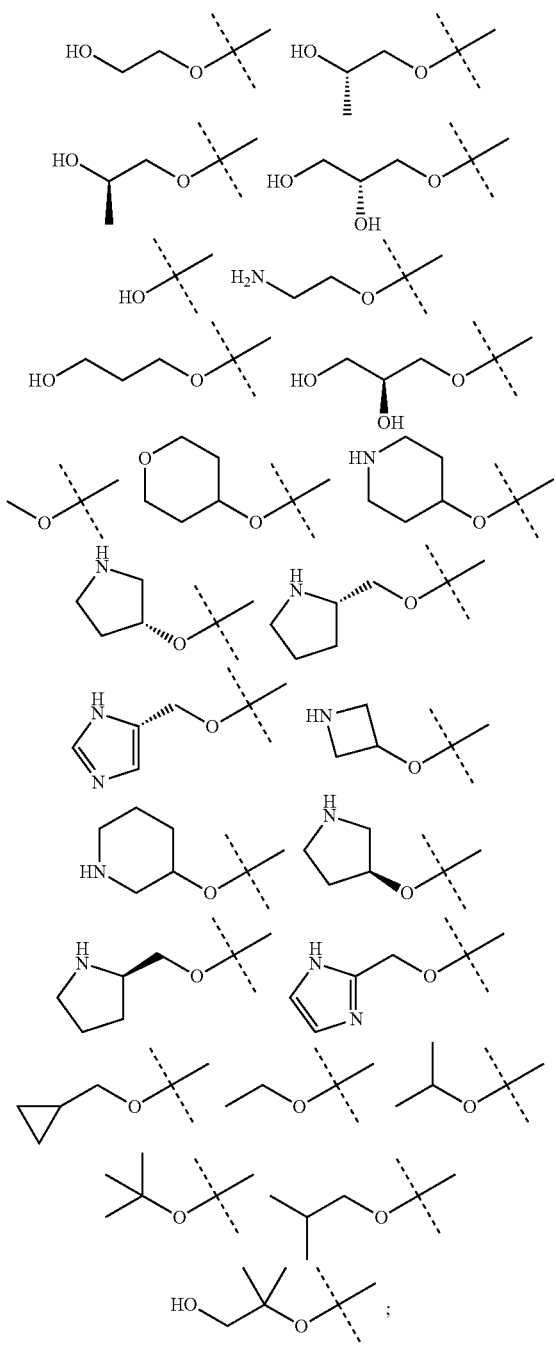

and all other variables are as defined in formula I or II, or as defined in any one of the embodiments above.

In another embodiment of the present invention, $X^1$ is

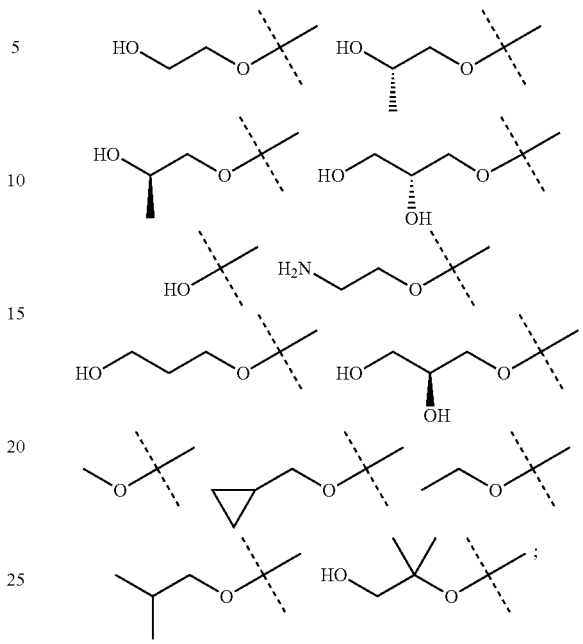

and all other variables are as defined in formula I or II, or as defined in any one of the embodiments above.

In an embodiment of the present invention, W is

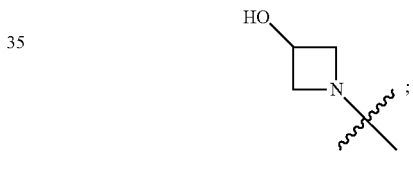

and all other variables are as defined in formula I or II, or as defined in any one of the embodiments above.

In an embodiment of the present invention, W is —$OR^{11'}$ wherein $R^{11'}$ is H or $C_1$-$C_{12}$ alkyl; and all other variables are as defined in formula I or II, or as defined in any one of the embodiments above.

In another embodiment of the present invention, W is —$OR^{11'}$ wherein $R^{11'}$ is H; and all other variables are as defined in formula I or II, or as defined in any one of the embodiments above.

In another embodiment of the present invention, W is —$OR^{11'}$ wherein $R^{11'}$ is $C_1$-$C_6$ alkyl; and all other variables are as defined in formula I or II, or as defined in any one of the embodiments above.

In an embodiment of the present invention, W' is —$NHSO_2R^8$; and all other variables are as defined in formula I or II, or as defined in any one of the embodiments above. In an embodiment of the present invention, $R^8$ is cyclopropyl; and all other variables are as defined in formula I or II, or as defined in any one of the embodiments above.

In an embodiment of the present invention, $R^6$ is halo, $C_2$-$C_8$ alkynyl, carbocyclyl, or —$SR^{16}$; and all other variables are as defined in formula I or II, or as defined in any one of the embodiments above.

In another embodiment of the present invention, $R^6$ is halo, $C_2$-$C_3$ alkynyl, $C_3$-carbocyclyl, or —$SR^{16}$ wherein $R^{16}$ is $C_1$-$C_2$ alkyl; and all other variables are as defined in formula I or II, or as defined in any one of the embodiments above.

In another embodiment of the present invention, $R^6$ is Br, I, SMe, $C_3$-carbocyclyl, or $C_2$ alkynyl; and all other variables are as defined in formula I or II, or as defined in any one of the embodiments above.

In an embodiment of the present invention, $R^{6'}$ is H, halo, or $C_1$-$C_3$ alkyl; and all other variables are as defined in formula I or II, or as defined in any one of the embodiments above.

In an embodiment of the present invention, $R^{6'}$ is H, F, Cl or methyl; and all other variables are as defined in formula I or II, or as defined in any one of the embodiments above.

In another embodiment of the present invention, $R^{6'}$ is F or Cl; and all other variables are as defined in formula I or II, or as defined in any one of the embodiments above.

In an embodiment of the present invention, p is 1 or 2; and all other variables are as defined in formula I or II, or as defined in any one of the embodiments above.

Another embodiment of the present invention includes compounds described in EXAMPLES 5-29 and compounds below:

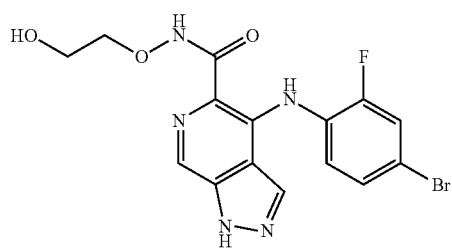

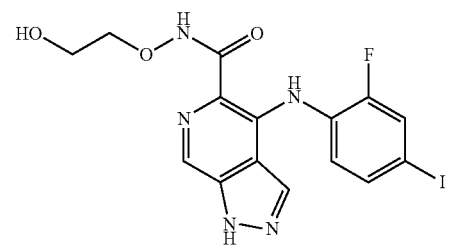

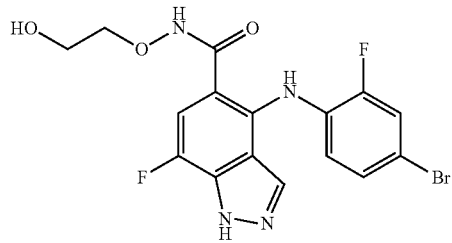

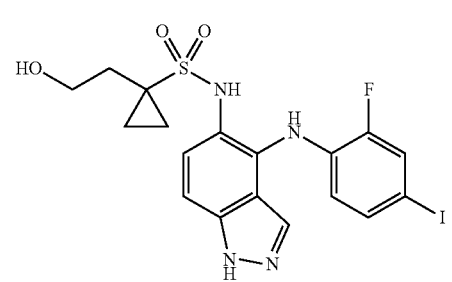

-continued

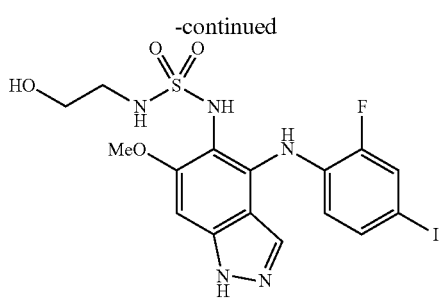

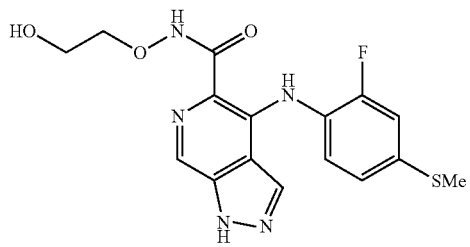

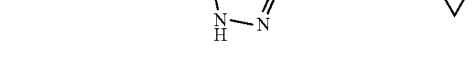
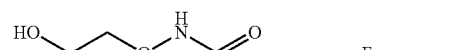

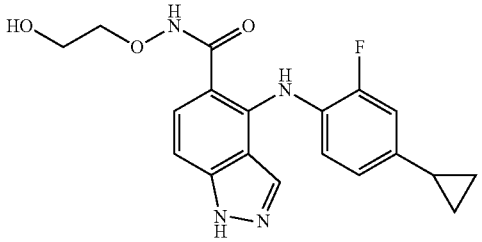

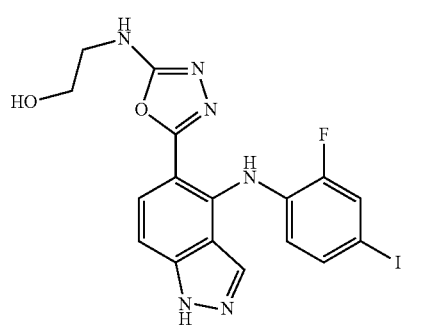

-continued
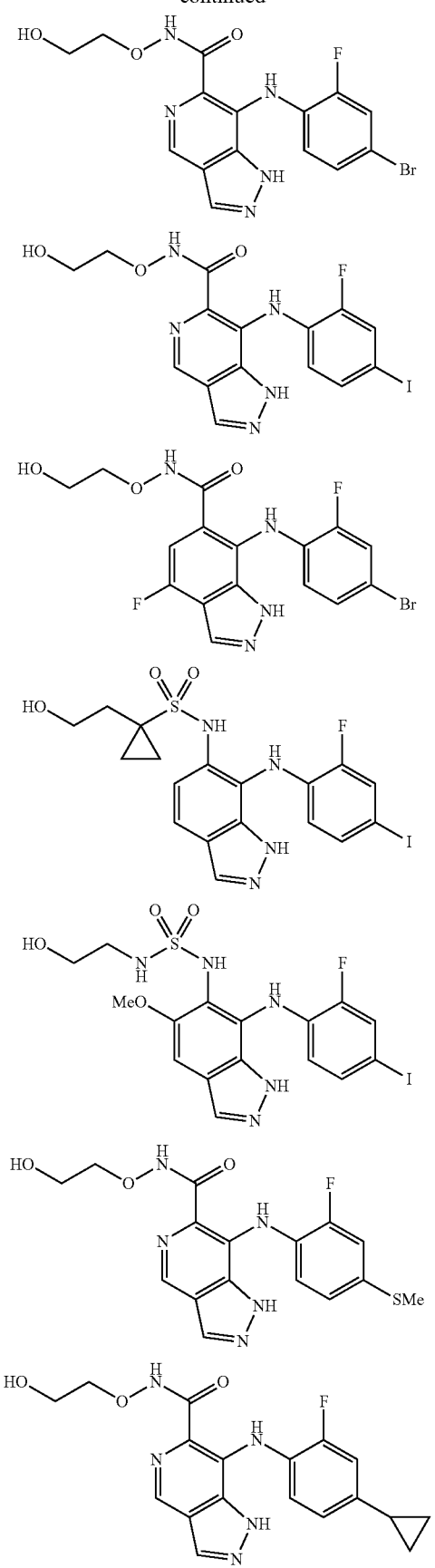
-continued
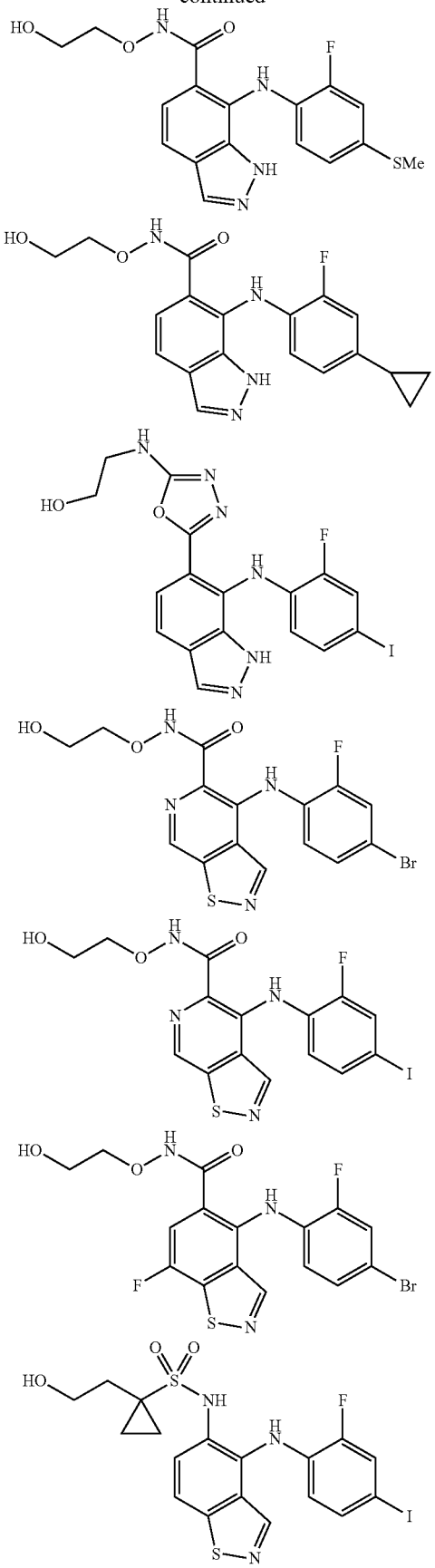

-continued
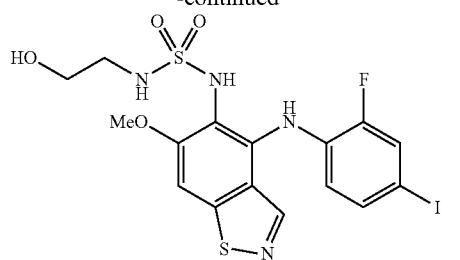
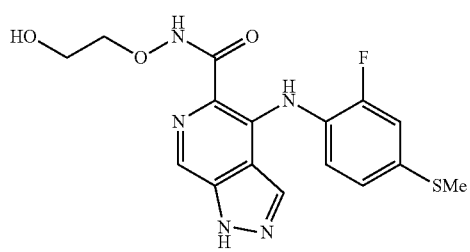
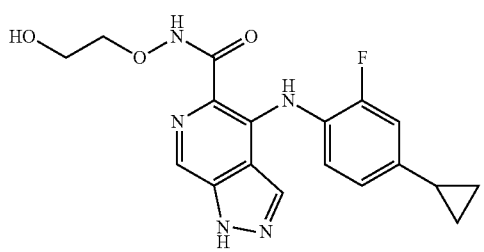
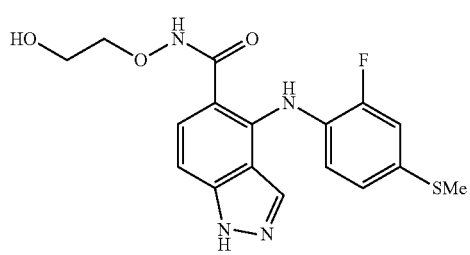
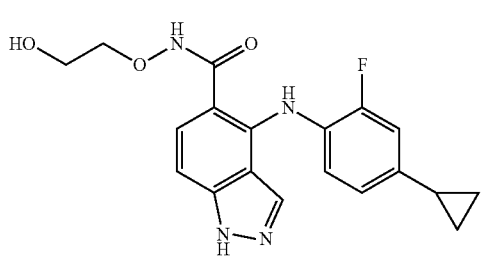
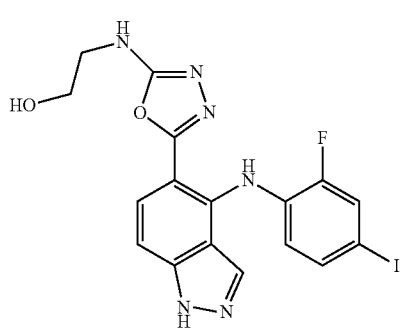
-continued
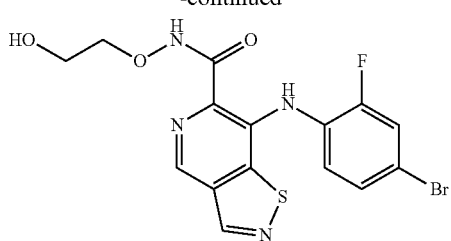
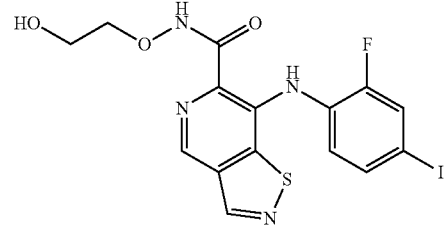
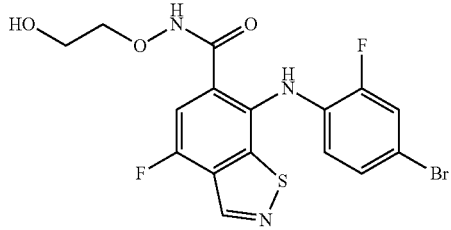
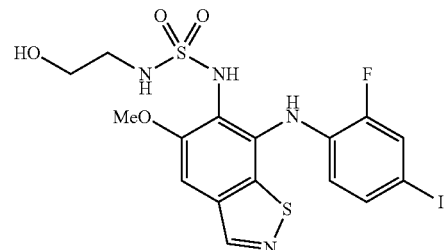
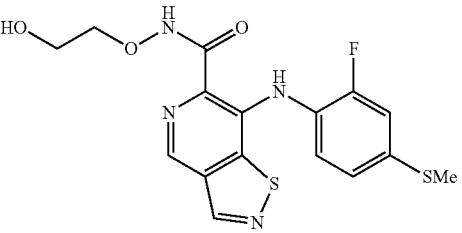
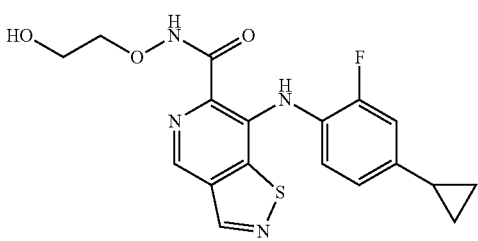

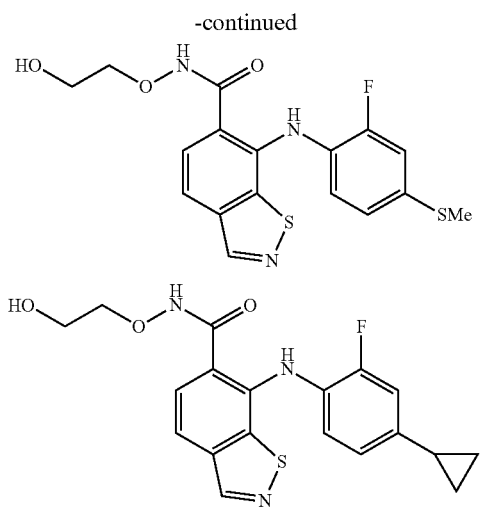
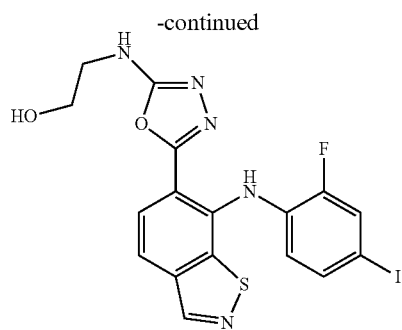

Compounds of formula I and II are prepared according to the procedures described below in the schemes and examples or by methods known in the art. For example, compounds of formula I may be prepared according to Scheme 1.

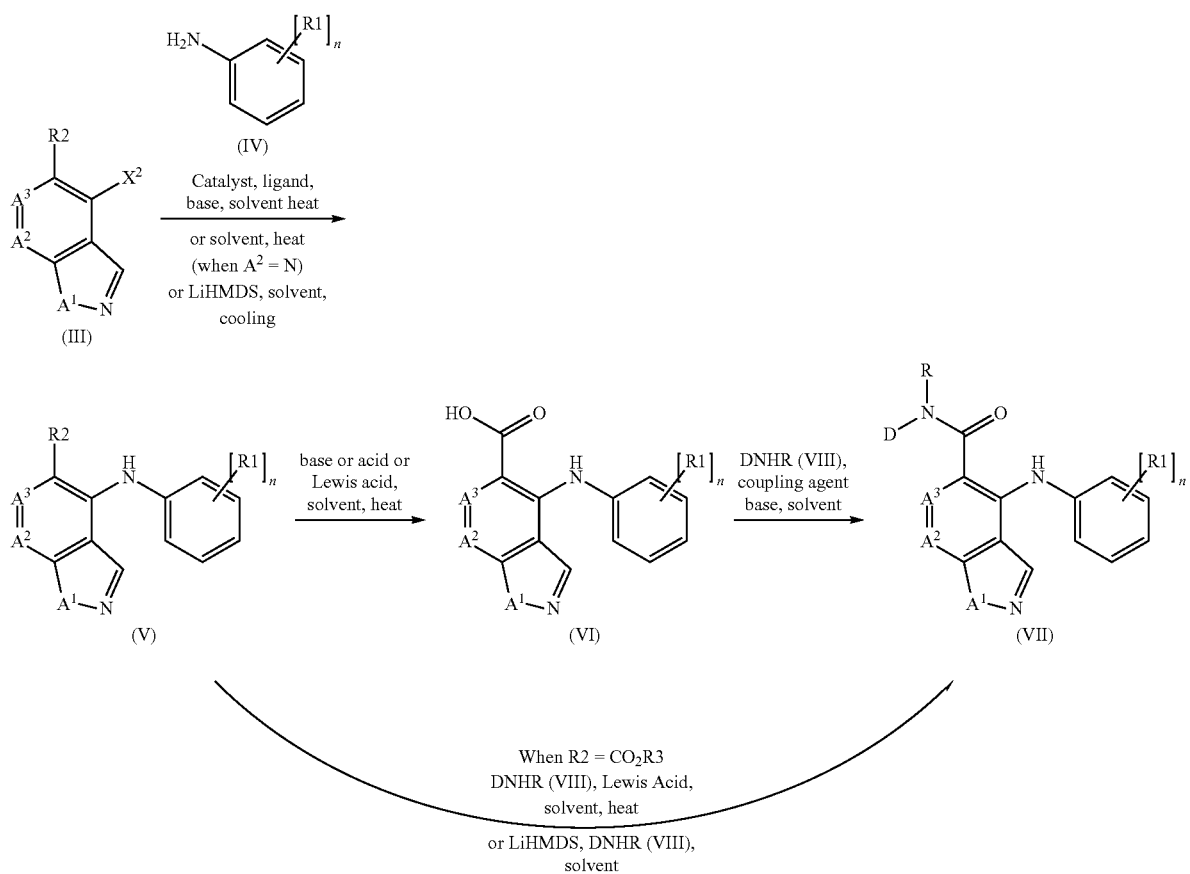

R1 = appropriate substituent, n = 1, 2, 3 or 4
R2 = CN, $CO_2H$, $CO_2R3$ (R3 = Me, Et, $^tBu$, lower alkyl)
$A^1$ = O, S, NH, NR5, NPG R5 = appropriate alkyl or substituted alkyl group
PG = appropriate protecting group (e.g. BOC, p-methoxybenzyl, p-toluenesulfonyl)
$A^2/A^3$ = CR4/N R4 = appropriate substituent
$X^2$ = halogen or other leaving group where DNHR may include, but is not limited to, a broad range of substituted and functionalised hydroxylamines (VIII) or amines Compounds of formula (VII) may be prepared from intermediates of formula (III) (prepared according to Schemes 2, 3 and 5-8 below). Compounds of formula (V) may be obtained from compounds of formula (III) by reaction with an aniline of formula (IV) (incorporating appropriate substituents R1), in the presence of a catalyst such as tris(dibenzylideneacetone) dipalladium (0) or palladium (II) acetate, a base such as potassium phosphate or cesium carbonate, a ligand such as Xantphos or 2-dicyclohexylphosphino-2',6'-(diisopropoxy)biphenyl, in a suitable solvent such as toluene or DME, at a temperature of from room temperature to the reflux temperature of the solvent, or under microwave irradiation at a temperature of from 70° C. to 150° C. Alternatively, compounds of formula (V) may be prepared from compounds of formula (III) by reaction of an aniline of formula (IV) in the presence of a strong base such as lithium bis(trimethylsilyl) amide, in a solvent such as THF at temperature of from −78° C. to room temperature. Alternatively, and preferentially when $A^2$ is N, the aniline and compound of formula (III) may be reacted in a solvent such as dioxane or DMF, in the presence of a base such as potassium carbonate at a temperature of from 50° C. to reflux temperature.

Compounds of formula (VI) can be obtained from compounds of formula (V) where R2 is $CO_2R3$ and R3 is Me, ethyl, other alkyl by reaction with a base such as sodium hydroxide, in a solvent such as ethanol or methanol, at a temperature of from room temperature up to reflux temperature. When R3 is $CO_2{}^tBu$ compounds of formula (VI) can be obtained from compounds of formula (V) by treatment with an acid such as TFA, neat, or in the presence of a solvent such as DCM at a temperature of from 0° C. to reflux. Alternatively, where R3 is Me saponification may be effected under non-basic conditions by treatment with a Lewis acid such as bis(tri-n-butyltin)oxide, in a solvent such as toluene, at a temperature of from room temperature to reflux.

Compounds of formula (VI) can be reacted with a functionalised hydroxylamine of formula (VIII) (commercially available or prepared according to Scheme 11) or an amine, and a suitable coupling agent, such as O-(7-aza-benzo-triazol-1-yl)-N,N,N',N'-tetra-methyluronium hexafluoro-phosphate, N-(3-dimethylaminopropyl)-N'-ethylcarbodiimide hydrochloride or N,N'-dicyclohexylcarbodiimide in the presence of N-hydroxy-1,2,3-benzotriazole, in the presence of a suitable base such as diisopropylethylamine or triethylamine in an inert solvent, such as tetrahydrofuran, N,N-dimethylformamide, or dichloromethane at a temperature of about room temperature, to obtain the compounds of formula (VII). Alternatively, compounds of formula (VII) can be obtained directly from compounds of formula (V) by reaction with an amine or hydroxylamine DNHR (VIII), in the presence of a strong base such as lithium bis(trimethylsilyl)amide, in a solvent such as THF, at a temperature of from −20° C. to room temperature. Alternatively, compounds of formula (VII) can be obtained directly from compounds of formula (V) by reaction with an amine or hydroxylamine DNHR (VIII) in the presence of a Lewis acid such as trimethyl aluminium, in a solvent such as DCM, at a temperature of from room temperature up to reflux temperature.

For compounds of formula (VII) where $A^1$ is N, protecting groups (NPG) may be added and removed at any stage of the synthesis as required.

Compounds of formula (III) where $A^1$ is NH, NR5 and NPG may be prepared according to Scheme 2.

Scheme 2

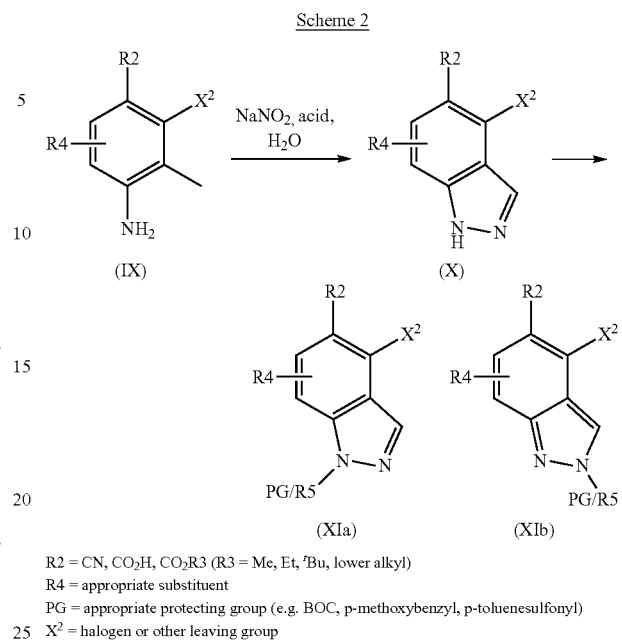

R2 = CN, $CO_2H$, $CO_2R3$ (R3 = Me, Et, $^tBu$, lower alkyl)
R4 = appropriate substituent
PG = appropriate protecting group (e.g. BOC, p-methoxybenzyl, p-toluenesulfonyl)
$X^2$ = halogen or other leaving group Compounds of formula (IX) may be prepared using methods described in the literature. Compounds of formula (X) may be prepared from compounds of formula (IX) by reaction with a diazotizing agent such as sodium nitrite, in the presence of an acid such as acetic acid or tetrafluoroboric acid and a solvent such as water, at a temperature of from −20° C. to 50° C. Compounds of formula (X) may be protected with a suitable protecting group to provide compounds of formula (XIa) and (XIb) by reaction with an appropriate sulfonyl chloride such as p-toluenesulfonyl chloride, or alkyl chloride such 2-(trimethylsilyl)ethoxymethyl chloride, in the presence of a base such as triethylamine or sodium hydride, in a solvent such as THF, or DCM, at a temperature of from 0° C. to room temperature. Alternatively, compounds of formula (X) may be protected with a carbamate protecting group such as tert-butyl carbamate by reaction of compounds of formula (X) with di-tert-butyl dicarbonate in the presence of a tertiary amine base such as triethylamine, in a solvent such as DCM, at a temperature of about room temperature. Indazoles prepared by these methods may be isolated as mixtures of isomers (XIa) and (XIb) as shown.

Alternatively, compounds of formula (III) where $A^1$ is NH, NR5, or NPG may be prepared according to Scheme 3.

Scheme 3

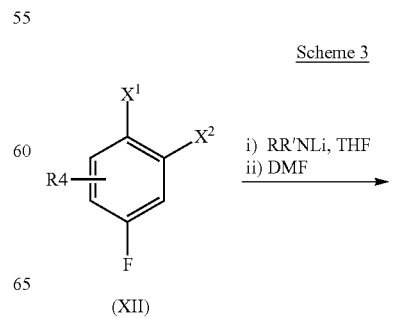

(XII)

-continued

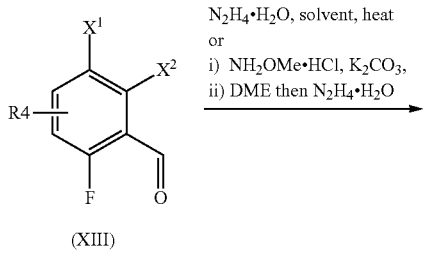

(XIII)

N₂H₄•H₂O, solvent, heat
or
i) NH₂OMe•HCl, K₂CO₃,
ii) DME then N₂H₄•H₂O

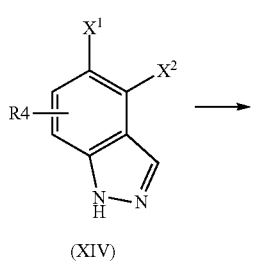

(XIV)

Catalyst, M$_x$(CN)$_n$,
solvent, heat
or
i) nBuLi or RMgX THF
ii) CO₂
or
Catalyst, CO, MEOH,
solvent

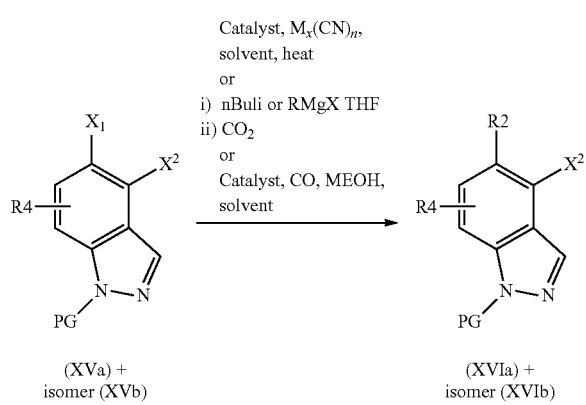

(XVa) + isomer (XVb)           (XVIa) + isomer (XVIb)

$X^1$ = Br, I
$X^2$ = Br, F, Cl, I
R2 = CO₂H, CO₂R3, CN
R5 = H, $^t$Bu
M = metal x = 1 or 2 n = 1, 2, 3 or 4
R4 = appropriate substituent

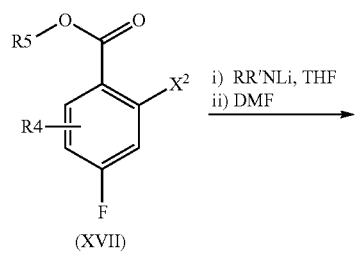

(XVII)

i) RR'NLi, THF
ii) DMF

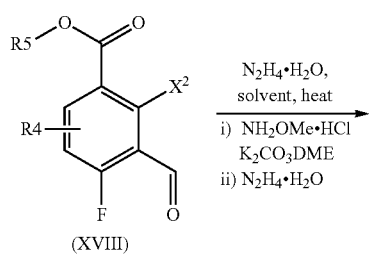

(XVIII)

N₂H₄•H₂O, solvent, heat
i) NH₂OMe•HCl K₂CO₃DME
ii) N₂H₄•H₂O

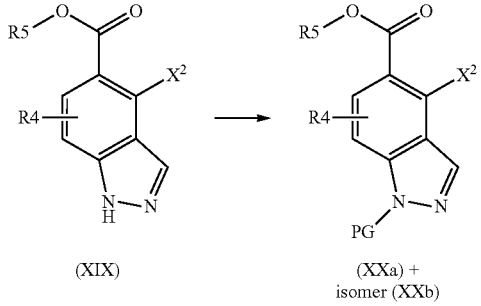

(XIX)                    (XXa) + isomer (XXb)

Compounds of formula (XII) and (XVII) may be obtained commercially or prepared using methods described in the literature. Compounds of formula (XIII) and (XVIII) may be prepared from compounds of formula (XII) and (XVII) respectively by reaction with a sterically hindered strong base such as lithium diisopropylamide, in a solvent such as THF, at a temperature of from −80° C. to 0° C., followed by quench with a formylating reagent such as DMF or 1-formylpiperidine. Compounds of formula (XIII) and (XVIII) may be converted to compounds of formula (XIV) and (XIX) by treatment with hydrazine hydrate, neat, or in a solvent such as ethanol or DME at a temperature of from room temperature to 150° C. Alternatively compounds of formula (XIV) and (XIX) may be prepared from compounds of formula (XIII) and (XVIII) by conversion to an intermediate oxime by reaction with a hydroxylamine such as O-methyl hydroxylamine, in a solvent such as DME, in the presence of a base such as potassium carbonate, at a temperature of from room temperature to reflux. The intermediate oximes may be converted to indazoles of formula (XIV) and (XIX) without isolation by treatment with hydrazine hydrate, neat, or in the presence of a solvent such as DME. Compounds of formula (XIV) and (XIX) may be converted to compounds of formula (XVa/XVb) and (XXa/XXb) using the methods described for the conversion of compounds of formula (X) to compounds of formula (XIa) and (X1b). Compounds of formula (XVa/XVb) where $X^1$ is I, Br may be converted to compounds of formula (XVIa/XVIb) where R2 is CO₂R3 by a number of different methods. Most preferentially, compounds of formula (XVIa/XVIb) may be prepared from compounds of formula (XVa/XVb) via metal-halogen exchange by treatment with a strong organometallic base such as n-butyllithium or a Grignard reagent such as isopropyl magnesium iodide in a solvent such as THF at a temperature of from −80° C. to 0° C. The intermediate aryl lithium or aryl magnesium species may be converted to compounds of formula (XVIa/XVIb) by quench with an electrophile such as CO₂ or methyl chloroformate. Alternatively, compounds of formula (XVIa/XVIb) may be prepared from compounds of formula (XVa/XVb) by transition metal catalyzed carbonylation using a catalyst such as palladium (II) acetate, a base such as DIPEA, a co-catalyst such as DMAP in a solvent such as methanol, and a carbon monoxide source such as Mo(CO)₆, at a temperature of from 80° C. to reflux, but preferentially using microwave irradiation at a temperature of from 150° C. to 200° C. at a pressure of from 1-10 bar. Compounds of formula (XVa/XVb) where $X^1$ is I or Br may be converted to compounds of formula (XVI) where R2 is CN by reaction with an metal cyanide such as zinc cyanide in the presence of a catalyst such as tetrakis (triphenylphosphine) palladium (0) in a solvent such as DMF at a temperature of from 50° C. to reflux temperature or using microwave heating at a temperature of from 120° C. to 200° C.

Compounds of formula (V) where $A^1$ is NH, NR5, or NPG may also be prepared according to Scheme 4.

Scheme 4

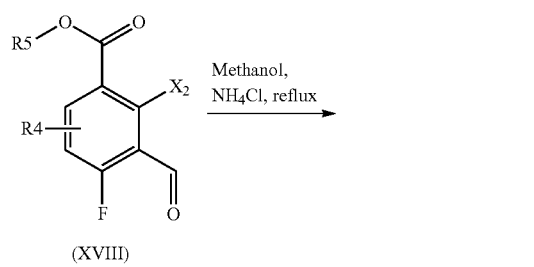

(XVIII)

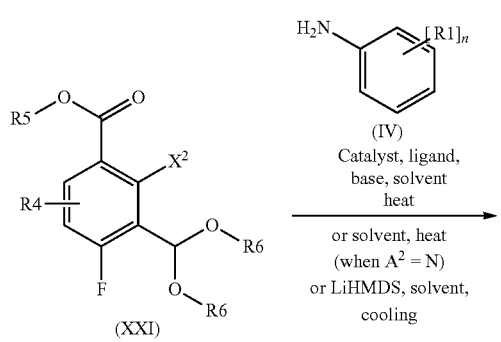

(XXI)

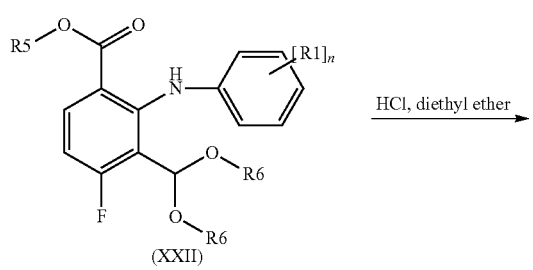

(XXII)

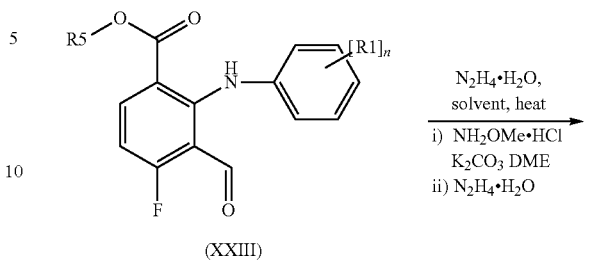

(XXIII)

(XXIV)

$X^2$ = Br, F, Cl, I
R2 = CO$_2$H, CO$_2$R3, CN
R3 = Me, Et, tButyl, lower alkyl
R4 = appropriate substituent
R5 = H, $^t$Bu
R6 = Me, Et, cycloalkyl
M = metal x = 1 or 2 n = 1, 2, 3 or 4

Compounds of formula (XVIII) may be obtained commercially or prepared using methods described in the literature. Compounds of formula (XVIII) may be converted to compounds of formula (XXI) by reaction with an alcohol such as methanol (R6=Me) in the presence of an acid such as ammonium chloride, at a temperature of about reflux. Compounds of formula (XXI) may be converted to compounds of formula (XXII) using the methods described for the conversion of compounds of formula (III) to compounds of formula (V) in Scheme 1. Compounds of formula (XXII) may be converted to compounds of formula (XXIII) by reaction with an acid such as hydrochloric acid in a solvent such as ether at a temperature of about room temperature. Compounds of formula (XXIII) may be converted to compounds of formula (XXIV) using the methods described for the conversion of compounds of formula (XVIII) to compounds of formula (XIX) in Scheme 3.

Compounds of formula (III) where $A^1$ is S and R2 is CO$_2$R3 may be prepared according to Scheme 5.

Scheme 5

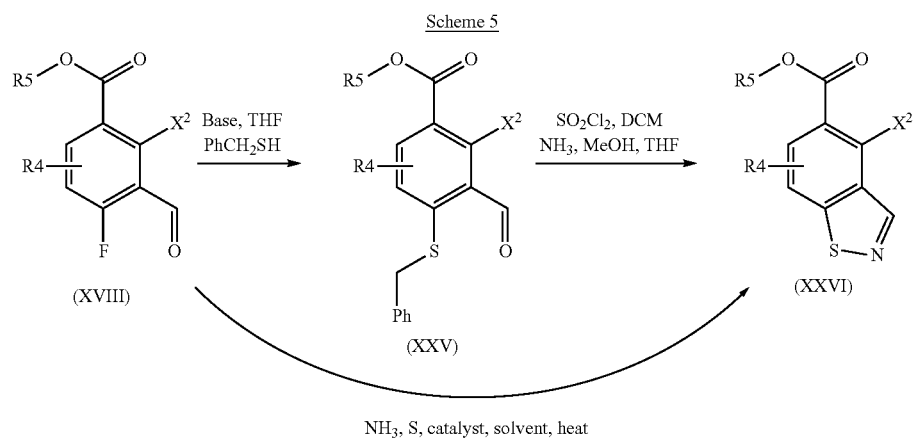

$X^2$ = Br, F, Cl, I
R3 = Me, Et, $^t$Bu or other appropriate group
R4 = appropriate substituent
R5 = H, tbutyl Compounds of formula (XVIII), prepared according to Scheme 3, may be converted to compounds of formula (XXVI) by a two-step process. Compounds of formula (XVIII) may be reacted with benzenemethane thiol in the presence of a base such as potassium tert-butoxide in a solvent such as THF at a temperature of from 0° C. to reflux. The intermediate thioethers of formula (XXV) may be converted to compounds of formula (XXVI) by treatment with sulfuryl chloride in a solvent such as dichloromethane followed by reaction with ammonia in a solvent such as ethanol/THF. Alternatively, compounds of formula (XXVI) may be prepared from compounds of formula (XVIII) directly by treatment with elemental sulfur, ammonia or ammonium hydroxide, in a solvent such as DMF or 2-methoxyethanol, in the presence of a catalyst such as methylamine at a temperature of from 100° C. to reflux, or a higher temperature than reflux (150 to 200° C.) with the use of a reaction autoclave at a pressure of from 1-20 bar.

Compounds of formula (XXIX) where $A^2$ is N may be prepared according to Scheme 6.

Scheme 6

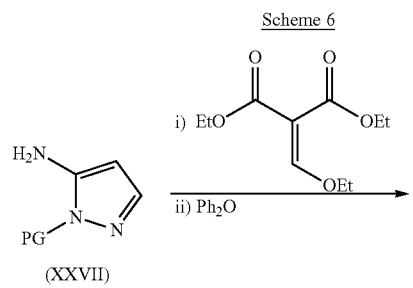

-continued

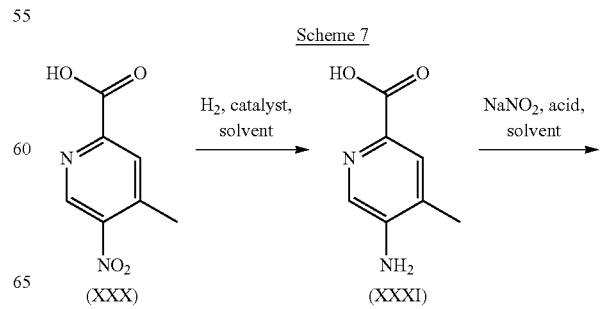

Protected aminopyrazoles of formula (XXVII) may be prepared using methods described in the literature. Compounds of formula (XXVII) may be reacted with a 2-alkoxy methylene malonic ester such as 2-ethoxymethylene-malonic acid diethyl ester, in the presence of a high-boiling solvent such as diphenyl ether at a temperature of from 150° C. to 300° C. to give compounds of formula (XXVIII). Compounds of formula (XXVIII) may be converted to compounds of formula (XXIX) by treatment with a halogenating agent such as phosphorous oxychloride, neat, or in the presence of a solvent such as toluene, with or without base such as triethylamine at a temperature of from 50° C. to reflux.

Compounds of formula XXXIVa and XXXIVb may be prepared according to Scheme 7.

Scheme 7

-continued

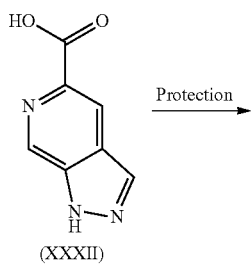

(XXXII)

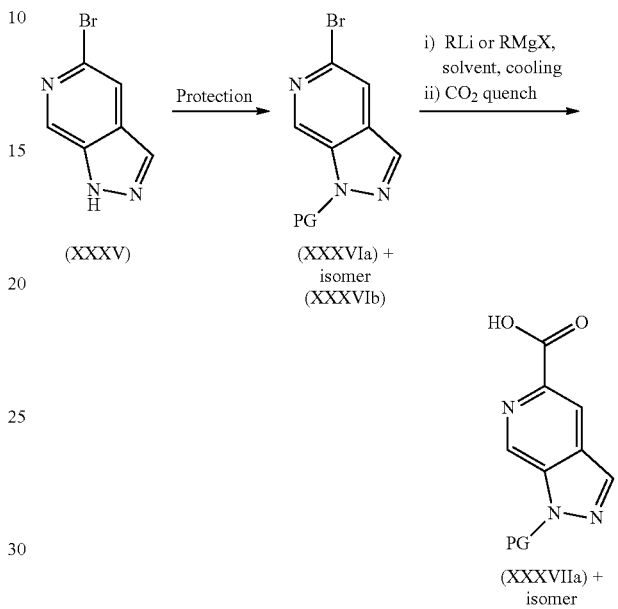

Indazoles of formula (XXXV) may be obtained commercially or prepared according to methods described in the literature. Compounds of formula (XXXVIa/XXXVIb) may be prepared from compounds of formula (XXXV) using the methods described for the conversion of compounds of formula (X) to compounds of formula (XIa/XIb) shown in Scheme 2. Compounds of formula (XXXVIa/XXXVIb) may be converted to acids of formula (XXXVIIa/XXXVIIb) by lithium-halogen exchange using a strong organometallic base such as n-butyl lithium in a solvent such as THF at a temperature of from −100° C. to −60° C., followed by quench with an electrophile such as carbon dioxide at a temperature of from −78° C. to 0° C. Alternatively compounds of formula (XXXVIa/XXXVIb) may be converted to compounds of formula (XXXVIIa/XXXVIIb) by formation of the intermediate ester prepared by reaction of heteroaryl halide with carbon monoxide (at a pressure of from 1-15 bar) in the presence of a catalyst such as palladium acetate or 1,1'-bis(diphenylphosphino)ferrocene and a ligand such as triphenyl phosphine and a base such as sodium acetate in the presence of an alcohol such as methanol in a solvent such as DMF or methanol at a temperature of from 80° C. to 200° C.

Compounds of formula II may be prepared according to Scheme 9.

Compounds of formula (XXX) may be obtained commercially or prepared using methods described in the literature. Compounds of formula (XXX) may be converted to compounds of formula (XXXI) by reduction of the nitro group using a catalyst such as Raney nickel under pressure of hydrogen (1-5 bar), in a solvent such as THF, at room temperature. Compounds of formula (XXXII) may be obtained from compounds of formula (XXXI) by treatment with a diazotizing agent such as sodium nitrite, in the presence of an acid such as acetic acid or tetrafluoroboric acid, and a solvent such as water, at a temperature of from −20° C. to 50° C. Compounds of formula (XXXII) may be converted to compounds of formula (XXXIII) where PG is SEM (SEM=2-(trimethylsilyl)ethoxymethyl) by treatment with SEM-Cl in the presence of a base such as sodium hydride, in a solvent such as THF at around room temperature. Compounds of formula (XXXIIIa/XXXIIIb) may be converted to compounds of formula (XXXIVa/XXXIVb) by ortho-lithiation with a strong base such as lithium tetramethyl piperidine, in a solvent such as THF, at a temperature of from −100° C. to −60° C., followed by quench with a halogenating agent such as iodine or hexachloroethane, at a temperature of from −100° C. to 0° C.

Intermediates of formula XXXVIIa/XXXVIIb may be prepared according to Scheme 8.

Scheme 9

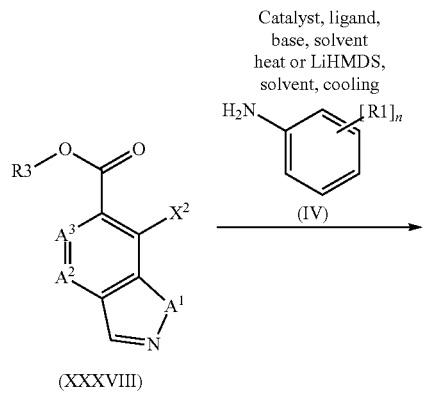

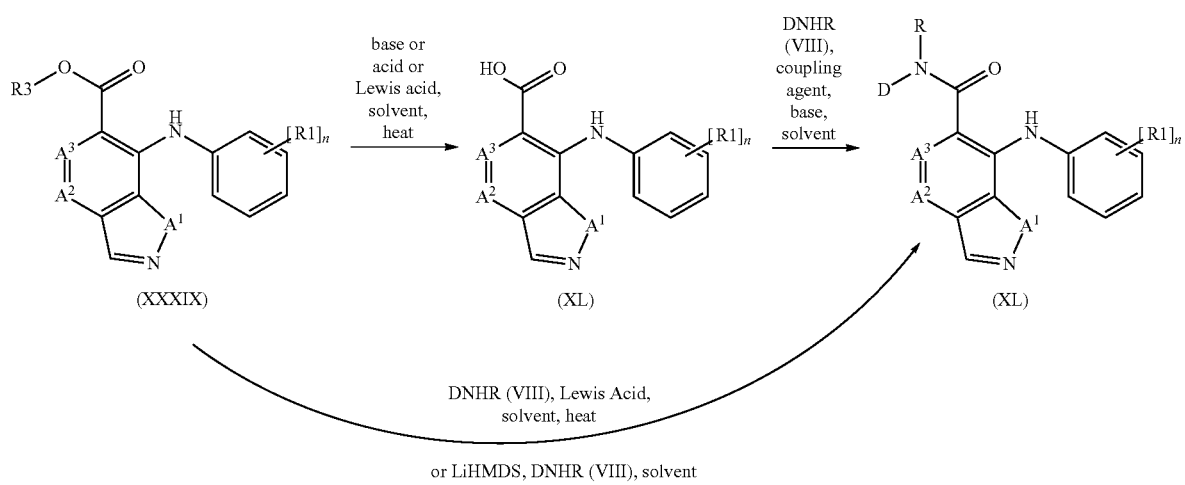

R3 = Me, Et, ᵗBu, lower alkyl)
X² = Cl, Br, I or other leaving group
A¹ = O, S, NH, NR5, NPG R5 = appropriate alkyl or substituted alkyl group
R1 = appropriate substituent, n = 1, 2, 3 or 4
PG = appropriate protecting group (e.g. BOC, p-methoxybenzyl, p-toluenesulfonyl) when A¹ = N
A²/A³ = CR4/N R4 = Appropriate substituent Compounds of formula (XXXIX) may be prepared from intermediates of formula (XXXVIII) (prepared according to Schemes 9 and 10 below). Compounds of formula (XXXIX) may be obtained from compounds of formula (XXXVIII) using the methods described for the conversion of compounds of formula (III) to compounds of formula (V) in Scheme 1. Compounds of formula (XLI) may be prepared from compounds of formula (XXXIX) and (XL) using the methods described for the conversion of compounds of formula (V) and (VI) to compounds of formula (VII) as shown in Scheme 1.

For compounds of formula (XLI) where A¹ is NH protecting groups (NPG) may be added and removed at any stage of the synthesis as required.

Intermediates of formula (XLVI) and (XLVII) may be prepared according to Scheme 10 below.

Scheme 10

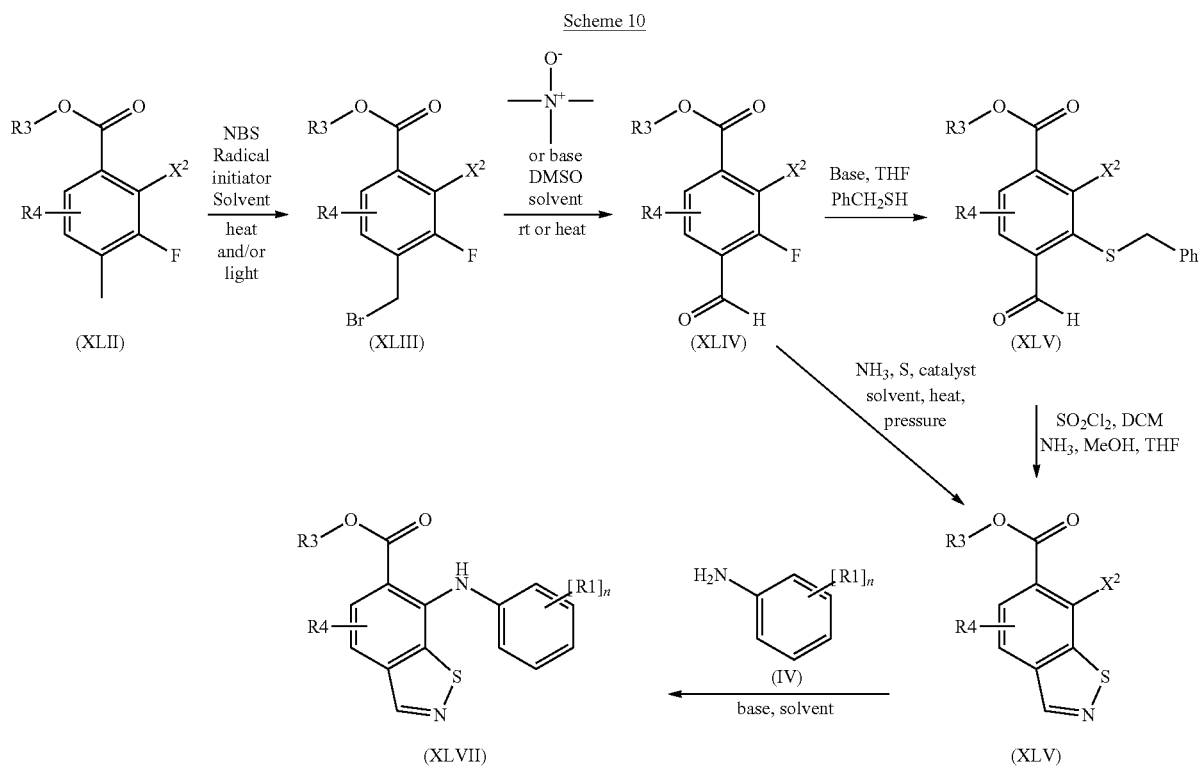

$X^2$ = halogen
R3 = Me, Et, $^t$Bu or lower alkyl
R4 = appropriate substituent
R1 = appropriate substituent, n = 1, 2, 3 or 4

Compounds of formula (XLII) may be reacted with a brominating agent such as NBS, in the presence of a radical initiator such as AIBN, in a solvent such as carbon tetrachloride, at reflux, with or without activation by light, to give compounds of formula (XLIII). Compounds of formula (XLIII) may be converted to compounds of formula (XLIV) by treatment with trimethylamine N-oxide, in the presence of DMSO, in a solvent such as DCM at a temperature of from room temperature to reflux. Alternatively, compounds of formula (XLIV) can be obtained by treatment of compounds of formula (XLIII) with a base such as sodium hydrogencarbonate, in DMSO, at a temperature of about 100° C. Compounds of formula (XLIV) may be reacted with benzenemethanethiol in the presence of a base such as potassium tert-butoxide, in a solvent such as THF at a temperature of from −78° C. to −30° C. to give compounds of formula (XLV). The intermediate thioethers of formula (XLV) may be converted to compounds of formula (XLVI) by treatment with sulfuryl chloride, in a solvent such as dichloromethane, followed by reaction with ammonia, in a solvent mixture such as methanol/THF. Alternatively, compounds of formula (XLVI) may be prepared from compounds of formula (XLIV) directly by treatment with elemental sulfur, ammonia or ammonium hydroxide, in a solvent such as DMF or 2-methoxyethanol, in the presence of a catalyst such as methylamine at a temperature of from 100° C. to reflux, or a higher temperature than reflux (150 to 200° C.) with the use of a reaction autoclave at a pressure of from 1-20 bar. Compounds of formula (XLVI) may be converted to compounds of formula (XLVII) using the methods described for the conversion of compounds of formula (III) to compounds of formula (V) in Scheme 1.

Compounds of formula (I) W'=NHSO$_2$R$^8$ or NHSO$_2$NR$^8$R$^{10}$ may be prepared according to Scheme 11.

Scheme 11

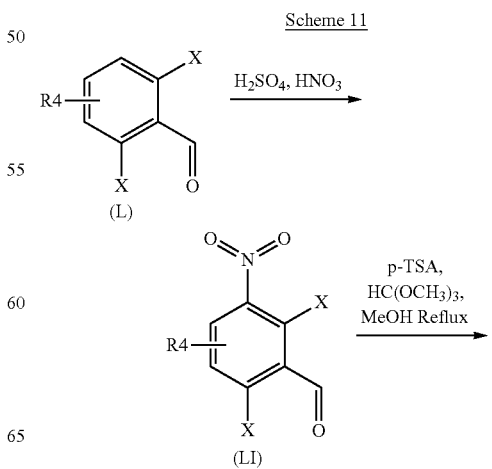

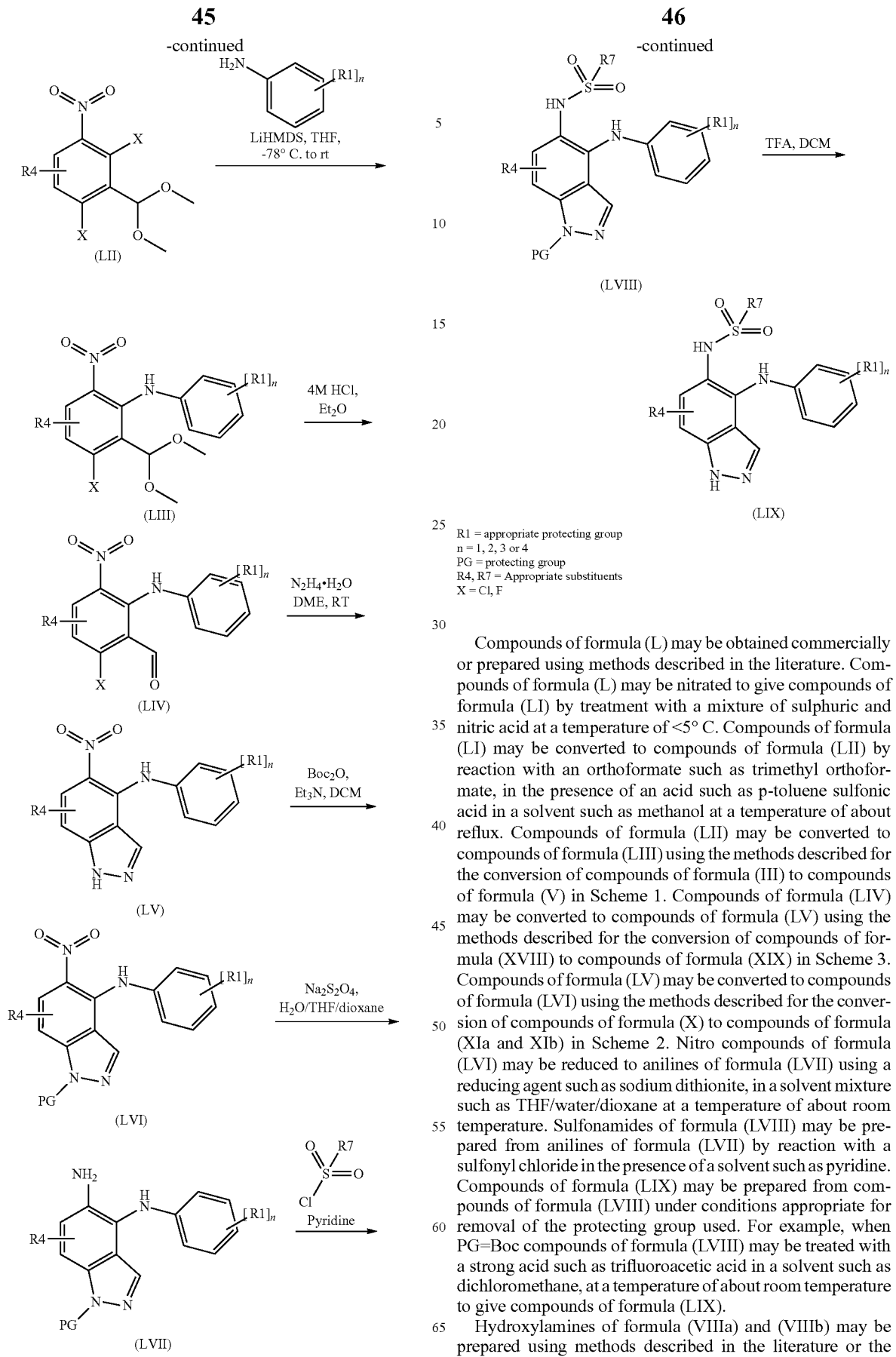

R1 = appropriate protecting group
n = 1, 2, 3 or 4
PG = protecting group
R4, R7 = Appropriate substituents
X = Cl, F Compounds of formula (L) may be obtained commercially or prepared using methods described in the literature. Compounds of formula (L) may be nitrated to give compounds of formula (LI) by treatment with a mixture of sulphuric and nitric acid at a temperature of <5° C. Compounds of formula (LI) may be converted to compounds of formula (LII) by reaction with an orthoformate such as trimethyl orthoformate, in the presence of an acid such as p-toluene sulfonic acid in a solvent such as methanol at a temperature of about reflux. Compounds of formula (LII) may be converted to compounds of formula (LIII) using the methods described for the conversion of compounds of formula (III) to compounds of formula (V) in Scheme 1. Compounds of formula (LIV) may be converted to compounds of formula (LV) using the methods described for the conversion of compounds of formula (XVIII) to compounds of formula (XIX) in Scheme 3. Compounds of formula (LV) may be converted to compounds of formula (LVI) using the methods described for the conversion of compounds of formula (X) to compounds of formula (XIa and XIb) in Scheme 2. Nitro compounds of formula (LVI) may be reduced to anilines of formula (LVII) using a reducing agent such as sodium dithionite, in a solvent mixture such as THF/water/dioxane at a temperature of about room temperature. Sulfonamides of formula (LVIII) may be prepared from anilines of formula (LVII) by reaction with a sulfonyl chloride in the presence of a solvent such as pyridine. Compounds of formula (LIX) may be prepared from compounds of formula (LVIII) under conditions appropriate for removal of the protecting group used. For example, when PG=Boc compounds of formula (LVIII) may be treated with a strong acid such as trifluoroacetic acid in a solvent such as dichloromethane, at a temperature of about room temperature to give compounds of formula (LIX).

Hydroxylamines of formula (VIIIa) and (VIIIb) may be prepared using methods described in the literature or the synthetic route outlined in Scheme 12.

Scheme 12

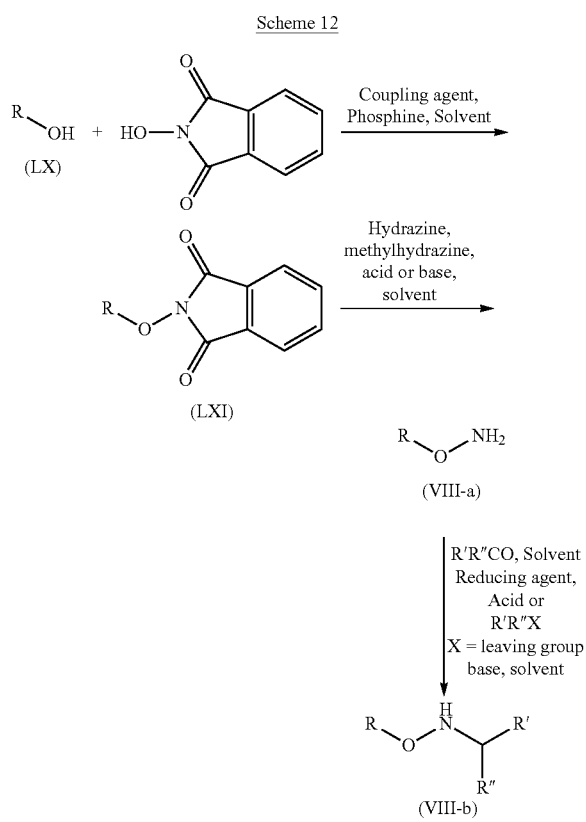

Primary or secondary alcohols of general formula (LX) may be prepared using methods described in the literature. The alcohols may be reacted with N-hydroxy phthalimide using a phosphine and coupling reagent such as diethyl azodicarboxylate to provide compounds of general formula (LXI). Compounds of general formula (LXI) may be deprotected using hydrazine, methyl hydrazine, an acid such as hydrochloric acid or a base such as aqueous ammonia to provide hydroxylamines of general formula (VIII-a).

Compounds of formula (VIII-a) may be further modified by reductive amination with aldehydes or ketones using a reducing agent such as sodium triacetoxy borohydride, sodium cyanoborohydride, or borane-pyridine in a solvent such as dichloroethane at a temperature of from ambient temperature to reflux to provide hydroxylamines of general formula (VIII-b). In addition, compounds of formula (XII-a) may be further modified by alkylation with an alkyl halide in the presence of a base such as triethylamine, in a solvent such as dichloromethane, to provide hydroxylamines of general formula (VIII-b).

Alternatively, hydroxylamines of formula (VIII-a) may be prepared according to Scheme 13.

Scheme 13

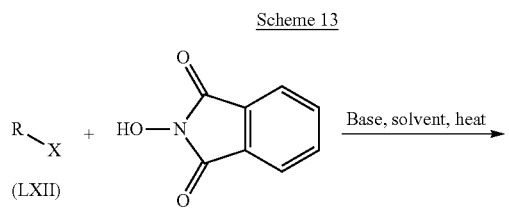

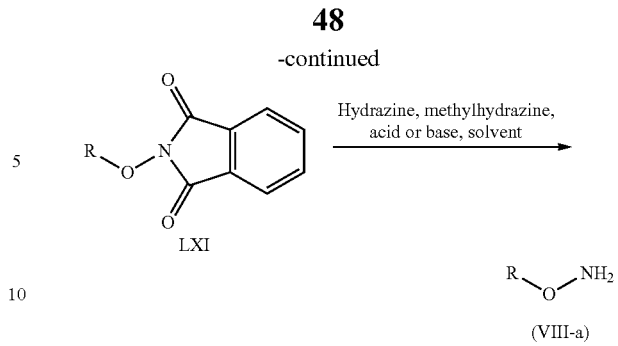

Alkyl halides of formula (LXII) may be reacted with N-hydroxy phthalimide in the presence of a base such as potassium carbonate in a solvent such as dimethyl sulfoxide at a temperature of from 10° C. to 50° C. Compounds of formula (LXI) may be converted to compounds of formula (VIII-a) using the methods described for the conversion of compounds of formula (LXI) to compounds of formula (VIII-a) in Scheme 12.

Alternatively, compounds of formula (VIII-a) may be prepared according to Scheme 14.

Scheme 14

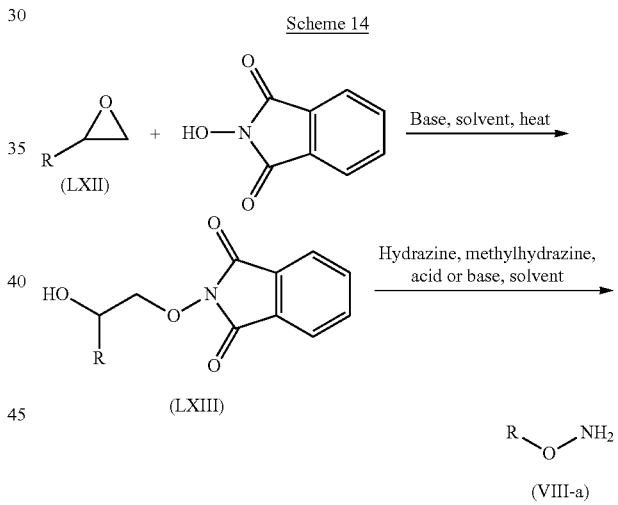

Compounds of formula (LXII) may be reacted with N-hydroxy phthalimide in the presence of a catalytic amount of a base such as DIPEA and a co-catalyst such as tetra-butyl ammonium bromide in a solvent such as toluene at a temperature of form 50° C. to reflux to give compounds of formula (LXIII). Compounds of formula (LXIII) may be converted to compounds of formula (VIII-a) using the methods described for the conversion of compounds of formula (LXI) to compounds of formula (VIII-a) in Scheme 12.

Anilines of general formula (LXV) used in condensations and cross-coupling reactions described above may be prepared by using methods described in the literature or according to Scheme 15.

Scheme 15

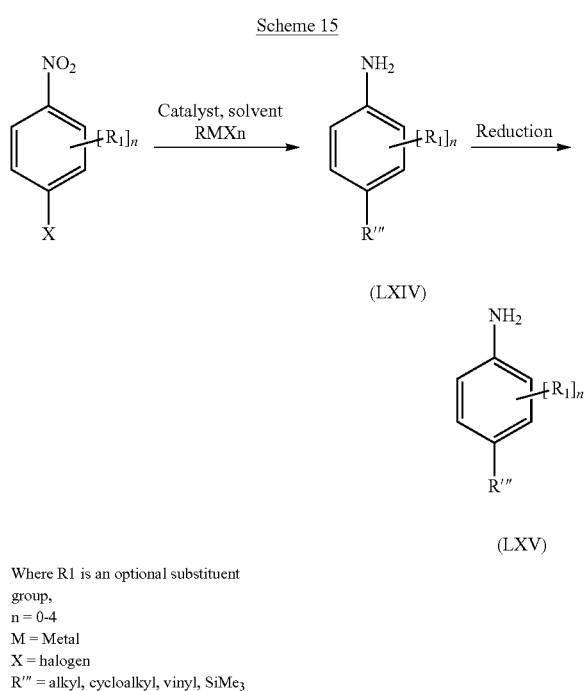

Where R1 is an optional substituent group,
n = 0-4
M = Metal
X = halogen
R'" = alkyl, cycloalkyl, vinyl, SiMe₃

Substituted 1-chloro-4-nitro benzene may be reacted with a metal R'"MXn, such as cyclopropyl boronic acid or hexamethyldisilazane, in a solvent such as xylene, using a catalyst such as tetrakis(triphenylphosphine)palladium, at a temperature of from room temperature to reflux to give compounds of formula (LXIV). The nitro group may be reduced using methods described in the literature such as reaction under an atmosphere of hydrogen, at a pressure of from 1 to 5 atmospheres, in the presence of a catalyst such as palladium on carbon, and in a solvent such as ethanol or ethyl acetate, at room temperature to give compounds of formula (LXV).

Alternatively, anilines of formula (LXVII) may be prepared according to Scheme 16.

Scheme 16

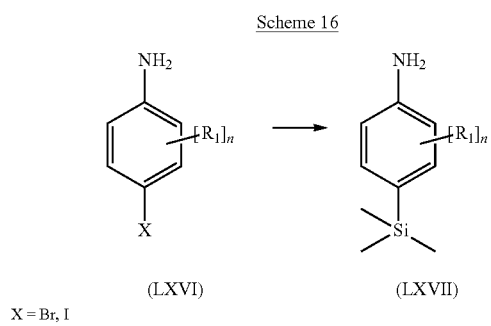

X = Br, I

4-Bromo or iodo anilines of formula (LXVI) may be reacted with at least 2 equivalents of a strong organometallic base such as n-butyllithium in a solvent such as THF at a temperature of from −100° C. to −20° C. followed by quench of the intermediate aryl lithium species with an electrophile such as trimethyl silyl chloride to give compounds of formula (LXVII).

It will be appreciated that where appropriate functional groups exist, compounds of formula (I) or any intermediates used in their preparation may be further derivatised by one or more standard synthetic methods employing substitution, oxidation, reduction, or cleavage reactions. Particular substitution approaches include conventional alkylation, arylation, heteroarylation, acylation, sulfonylation, halogenation, nitration, formylation and coupling procedures.

For example, aryl bromide or chloride groups may be converted to aryl iodides using a Finkelstein reaction employing an iodide source such as sodium iodide, a catalyst such as copper iodide and a ligand such as trans-N,N'-dimethyl-1,2-cyclohexane diamine in a solvent such as 1,4-dioxane and heating the reaction mixture at reflux temperature. Aryl trialkylsilanes may be converted to aryl iodides by treating the silane with an iodide source such as iodine monochloride in a solvent such as dichloromethane with or without Lewis acid such as silver tetrafluoroborate at a temperature from −40° C. to reflux.

In a further example primary amine (—NH₂) groups may be alkylated using a reductive alkylation process employing an aldehyde or a ketone and a borohydride, for example sodium triacetoxyborohydride or sodium cyanoborohydride, in a solvent such as a halogenated hydrocarbon, for example 1,2-dichloroethane, or an alcohol such as ethanol, where necessary in the presence of an acid such as acetic acid at around ambient temperature. Secondary amine (—NH—) groups may be similarly alkylated employing an aldehyde.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-yl)-N,N,N',N'-tetramethyluronium hexafluorophosphate) in a suitable solvent such as dichloromethane. Similarly, amine groups may be converted into sulfonamide groups (—NHSO₂R' or —NR"SO₂R') by reaction with an appropriate sulfonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (—NH₂) may be obtained by reduction of a nitro (—NO₂) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—CH₂NH₂) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at a temperature from −78° C. to the reflux temperature of the solvent.

In a further example, amine (—NH₂) groups may be obtained from carboxylic acid groups (—CO₂H) by conversion to the corresponding acyl azide (—CON₃), Curtius rearrangement and hydrolysis of the resultant isocyanate (—N═C═O).

Aldehyde groups (—CHO) may be converted to amine groups (—CH₂NR'R")) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH=CHR') by the use of a Wittig or Wadsworth-Emmons reaction using an appropriate phosphorane or phosphonate under standard conditions known to those skilled in the art.

Aldehyde groups may be obtained by reduction of ester groups (such as —$CO_2$Et) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—$CO_2$R') may be converted into the corresponding acid group (—$CO_2$H) by acid- or base-catalused hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—$CO_2$H) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e —$CO_2$H to —$CH_2CO_2$H) by conversion to the corresponding acid chloride (—COCl) followed by Arndt-Eistert synthesis.

In a further example, —OH groups may be generated from the corresponding ester (e.g. —$CO_2$R'), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—$CO_2$H), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thioyl chloride in a halogenated hydrocarbon (e.g. dichloromethane) to yield the corresponding chloride. A base (e.g. triethylamine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteroaryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

The compounds of the present invention are tested for their capacity to inhibit MEK activity and activation (primary assays) and for their biological effects on growing cells (secondary assays) as described below. The compounds of the present invention having $IC_{50}$ of less than 5 µM (more preferably less than 0.1 µM, most preferably less than 0.01 µM) in the MEK activity assay of Example 1, $IC_{50}$ of less than 5 µM (more preferably less than 1 µM, even more preferably less than 0.1 µM, most preferably less than 0.01 µM) in the MEK activation assay of Example 2, $EC_{50}$ of less than 10 µM (more preferably less than 1 µM, even more preferably less than 0.5 µM, most preferably less than 0.1 µM) in the cell proliferation assay of Example 3, and/or $EC_{50}$ of less than 10 µM (more preferably less than 1 µM, even more preferably less than 0.5 µM, most preferably less than 0.1 µM) in the ERK phosphorylation assay of Example 4, are useful as MEK inhibitors.

The present invention includes a composition (e.g., a pharmaceutical composition) comprising a compound of formula I or II (and/or solvates and/or salts thereof) and a carrier (a pharmaceutically acceptable carrier). The present invention also includes a composition (e.g., a pharmaceutical composition) comprising a compound of formula I or II (and/or solvates and/or salts thereof) and a carrier (a pharmaceutically acceptable carrier), further comprising a second chemotherapeutic and/or a second anti-inflammatory agent such as those described herein. The present compositions are useful for inhibiting abnormal cell growth or treating a hyperproliferative disorder in a mammal (e.g., human). The present compositions are also useful for treating inflammatory diseases in a mammal (e.g., human).

The present compounds and compositions are also useful for treating an autoimmune disease, destructive bone disorder, proliferative disorders, infectious disease, viral disease, fibrotic disease or neurodegenerative disease in a mammal (e.g., human). Examples of such diseases/disorders include, but are not limited to, diabetes and diabetic complications, diabetic retinopathy, retinopathy of prematurity, age-related macular degeneration, hemangioma, idiopathic pulmonary fibrosis, rhinitis and atopic dermatitis, renal disease and renal failure, polycystic kidney disease, congestive heart failure, neurofibromatosis, organ transplant rejection, cachexia, stroke, septic shock, heart failure, organ transplant rejection, Alzheimer's disease, chronic or neuropathic pain, and viral infections such as HIV, hepatitis (B) virus (HBV), human papilloma virus (HPV), cytomegalovirus (CMV), and Epstein-Barr virus (EBV). Chronic pain, for purposes of the present invention includes, but is not limited to, idiopathic pain, and pain associated with chronic alcoholism, vitamin deficiency, uremia, hypothyroidism, inflammation, arthritis, and post-operative pain. Neuropathic pain is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, arthritis pain, and nerve injury between the peripheral nervous system and the central nervous system.

The present compounds and compositions are also useful for treating pancreatitis or kidney disease (including proliferative glomerulonephritis and diabetes-induced renal disease) in a mammal (e.g., human).

The present compounds and compositions are also useful for the prevention of blastocyte implantation in a mammal (e.g., human).

The present invention includes a method of inhibiting abnormal cell growth or treating a hyperproliferative disorder in a mammal (e.g., human) comprising administering to said mammal a therapeutically effective amount of a compound of formula I or II (and/or solvates and/or salts thereof) or a composition thereof. Also included in the present invention is a method of treating an inflammatory disease in a mammal (e.g., human) comprising administering to said mammal a therapeutically effective amount of a compound of formula I or II (and/or solvates and/or salts thereof) or a composition thereof.

The present invention includes a method of inhibiting abnormal cell growth or treating a hyperproliferative disorder in a mammal (e.g., human) comprising administering to said mammal a therapeutically effective amount of a compound of formula I or II (and/or solvates and/or salts thereof) or a composition thereof, in combination with a second chemotherapeutic agent such as those described herein. The present invention also includes a method of treating an inflammatory disease in a mammal (e.g., human) comprising administering to said mammal a therapeutically effective amount of a compound of formula I or II (and/or solvates and/or salts thereof) or a composition thereof, in combination with a second anti-inflammatory agent such as those described herein.

The present invention includes a method of treating an autoimmune disease, destructive bone disorder, proliferative disorders, infectious disease, viral disease, fibrotic disease or neurodegenerative disease in a mammal (e.g., human) comprising administering to said mammal a therapeutically effective amount of a compound of formula I or II (and/or solvates and salts thereof) or a composition thereof, and optionally further comprising a second therapeutic agent. Examples of such diseases/disorders include, but are not limited to, diabetes and diabetic complications, diabetic retinopathy, retinopathy of prematurity, age-related macular degeneration, hemangioma, idiopathic pulmonary fibrosis, rhinitis and atopic dermatitis, renal disease and renal failure, polycystic kidney disease, congestive heart failure, neurofibromatosis, organ transplant rejection, cachexia, stroke, septic shock, heart failure, organ transplant rejection, Alzheimer's disease, chronic or neuropathic pain, and viral infections such as HIV, hepatitis (B) virus (HBV), human papilloma virus (HPV), cytomegalovirus (CMV), and Epstein-Barr virus (EBV).

The present invention includes a method of treating pancreatitis or kidney disease (including proliferative glomerulonephritis and diabetes-induced renal disease) in a mammal (e.g., human) comprising administering to said mammal a therapeutically effective amount of a compound of formula I or II (and/or solvates and salts thereof) or a composition thereof, and optionally further comprising a second therapeutic agent.

The present invention includes a method for preventing of blastocyte implantation in a mammal (e.g., human) comprising administering to said mammal a therapeutically effective amount of a compound of formula I or II (and/or solvates and salts thereof) or a composition thereof, and optionally further comprising a second therapeutic agent.

The present invention includes a method of using the present compounds for in vitro, in situ, and in vivo diagnosis or treatment of mammalian cells, organisms, or associated pathological conditions.

It is also believed that the compounds of the present invention can render abnormal cells more sensitive to treatment with radiation for purposes of killing and/or inhibiting the growth of such cells. Accordingly, this invention further relates to a method for sensitizing abnormal cells in a mammal (e.g., human) to treatment with radiation which comprises administering to said mammal an amount of a compound of formula I or II (and/or solvates and salts thereof) or a composition thereof, which amount is effective is sensitizing abnormal cells to treatment with radiation.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic or anti-inflammatory agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

EXAMPLES

| Abbreviations | |
| --- | --- |
| AIBN | Azobisisobutyronitrile |
| BOC | tert-butoxy carbonyl |
| nBuLi | n-Butyllithium |
| $CDCl_3$ | Deuterated chloroform |
| $CD_3OD$ | Deuterated methanol |
| DCM | Dichloromethane |
| DIAD | Diisopropyl azo-dicarboxylate |
| DIPEA | Diisopropylethylamine |
| DMAP | N,N'-dimethyl 4-amino pyridine |
| DME | Ethyleneglycol dimethyl ether |
| DMF | Dimethylformamide |
| DMSO | Dimethylsulfoxide |
| Dppf | 1,1'-Bis(diphenylphosphino)fenocene |
| EDCI | 1-Ethyl-3-(3'-dimethylaminopropyl)carbodiimide hydrochloride |
| $Et_3N$ | Triethylamine |
| $Et_2O$ | Diethyl ether |
| HATU | O-(7-Azabenzotriazol-1-yl)-N,N,N',N'-tetramethyluronium hexafluorophosphate |
| HCl | Hydrochloric acid |
| Hyflo ® | Diatomaceous earth |
| HM-N | Isolute ® diatomaceous earth absorbent |
| HOBt | 1-Hydroxybenzotriazole |
| HPLC | High pressure liquid chromatography |
| IMS | Industrial methylated spirits |
| $K_3PO_4$ | Potassium phosphate tribasic |
| LHMDS | Lithium bis(trimethylsilyl)amide |
| MeOH | Methanol |
| $NaHCO_3$ | Sodium hydrogen carbonate |
| $NH_4Cl$ | Ammonium chloride |
| NaOH | Sodium hydroxide |
| $Na_2SO_4$ | Sodium sulphate |
| $Pd(dppf)Cl_2$ | [1,1'-Bis(diphenylphosphino)ferrocene]dichloropalladium(II) |
| $Pd(PPh_3)_4$ | Tetrakis(triphenylphosphine)palladium(0) |
| $Pd_2dba_3$ | Tris-(dibenzylideneacetone)dipalladium(0) |
| Si-PPC | Pre-packed silica flash chromatography cartridge: Isolute ® SPE, Biotage SNAP ® or ISCO Redisep ® SCX-2 Isolute ® silica-based sorbent with a chemically bonded propylsulfonic acid functional group. |
| TBME | tert-Butyl methyl ether |
| TMEDA | Tetramethylethylene diamine |
| THF | Tetrahydrofuran |
| TFA | Trifluoroacetic acid |
| TMSCl | Trimethylsilyl chloride |
| Xantphos | 4,5-Bis(diphenylphosphino)-9,9-dimethylxanthene |

General Experimental Conditions $^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography—Mass Spectrometry (LCMS) experiments to determine retention times ($R_T$) and associated mass ions were performed using one of the following methods.

Method A: Experiments performed on a Waters Micromass ZQ quadrupole mass spectrometer linked to a Hewlett Packard HP1100 LC system with diode array detector. This system uses a Higgins Clipeus 5 micron C18 100×30 mm column and a 1 ml/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 5 minutes.

Method B: Experiments performed on a Waters Platform LC quadrupole mass spectrometer linked to a Hewlett Packard HP1100 LC system with diode array detector and 100 position autosampler using a Phenomenex Luna C18(2) 30×46 mm column and a 2 ml/minute flow rate. The solvent system was 95% water containing 0.1% formic acid (solvent A) and 5% acetonitrile containing 0.1% formic acid (solvent B) for the first 0.50 minutes followed by a gradient up to 5% solvent A and 95% solvent B over the next 4 minutes. The final solvent system was held constant for a further 0.50 minutes.

Method C: Experiments performed on a PE Sciex API 150 EX quadrupole mass spectrometer linked to a Shimadzu LC-10AD LC system with diode array detector and 225 position autosampler using a Kromasil C18 50 x 4.6 mm column and a 3 ml/minute flow rate. The solvent system was a gradient starting with 100% water with 0.05% TFA (solvent A) and 0% acetonitrile with 0.0375% TFA (solvent B), ramping up to 10% solvent A and 90% solvent B over 4 minutes. The final solvent system was held constant for a further 0.50 minutes.

Microwave experiments were carried out using a Personal Chemistry Emrys Iniatiator™ or Optimizer™, which uses a single-mode resonator and dynamic field tuning, both of which give reproducibility and control. Temperature from 40-250° C. can be achieved, and pressures of up to 20bar can be reached.

Example 1

MEK Assay (MEK Activity Assay)

Constitutively activated human mutant MEK1 expressed in insect cells is used as source of enzymatic activity at a final concentration in the kinase assay of 15 nM.

The assay is carried out for 30 minutes in the presence of 50 μM ATP using recombinant GST-ERK1 produced in *E. Coli* as substrate. Phosphorylation of the substrate is detected and quantified using HTRF reagents supplied by Cisbio. These consist of an anti-GST antibody conjugated to allophycocyanin (XL665) and an anti-phospho (Thr202/Tyr204) ERK antibody conjugated to europium-cryptate. These are used at a final concentration of 4 μg/ml and 0.84 μg/ml respectively. The anti-phospho antibody recognises ERK1 dually phosphorylated on Thr202 and Tyr204. When both antibodies are bound to ERK1 (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multiwell fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $IC_{50}$ values are calculated using the XLfit software package (version 2.0.5).

Title compounds of EXAMPLES 5-9, 12-13, 16, 20-23, and 25-27 exhibited an $IC_{50}$ of less than 0.1 μM in the assay described in EXAMPLE 1. Title compounds of EXAMPLES 10-11, 15, 17 and 24 exhibited an $IC_{50}$ of between 0.1 and 0.6 μM in the assay described in EXAMPLE 1.

Example 2 bRaf Assay (MEK Activation Assay)

Constitutively activated bRaf mutant expressed in insect cells is used as source of enzymatic activity.

The assay is carried out for 30 minutes in the presence of 200 μM ATP using recombinant GST-MEK1 produced in *E. Coli* as substrate. Phosphorylation of the substrate is detected and quantified using HTRF, and reagents are supplied by Cisbio. These consist of an anti-GST antibody conjugated to allophycocyanin (XL665) and an anti-phospho (Ser217/Ser221) MEK antibody conjugated to europium-cryptate. The anti-phospho antibody recognises MEK dually phosphorylated on Ser217 and Ser221 or singly phosphorylated on Ser217. When both antibodies are bound to MEK (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multi-well fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $IC_{50}$ values are calculated using the XLfit software package (version 2.0.5).

Example 3

Cell Proliferation Assay

Compounds are tested in a cell proliferation assay using the following cell lines:
HCT116 human colorectal carcinoma (ATCC)
A375 human malignant melanoma (ATCC)

Both cell lines are maintained in DMEM/F12 (1:1) media (Gibco) supplemented with 10% FCS at 37° C. in a 5% $CO_2$ humidified incubator.

Cells are seeded in 96-well plates at 2,000 cells/well and after 24 hours they are exposed to different concentrations of compounds in 0.83% DMSO. Cells are grown for a further 72h, and an equal volume of CellTiter-Glo reagent (Promega) is added to each well. This lyses the cells and generates a luminescent signal proportional to the amount of ATP released (and therefore proportional to the number of cells in the well) that can be detected using a multi-well luminometer.

The $EC_{50}$ is defined as the concentration at which a given compound achieves 50% inhibition of control. $IC_{50}$ values are calculated using the XLfit software package (version 2.0.5). In this assay, title compounds of EXAMPLE 5-7, 9-14, 16-17, 20-22 and 24-27 exhibited an $EC_{50}$ of less than 0.5 μM in the HCT116 cell line. The title compound of EXAMPLE 8 exhibited an $EC_{50}$ of less than 0.6 μM in the HCT116 cell line. Title compounds of EXAMPLES 5-12, 14, 16-17 and 20-27 exhibited an $EC_{50}$ of less than 0.1 μM in the A375 cell line.

Example 4

Phospho-ERK Cell-Based Assay

Compounds are tested in a cell-based phospho-ERK ELISA using the following cell lines:
HCT116 human colorectal carcinoma (ATCC)
A375 human malignant melanoma (ATCC)

Both cell lines are maintained in DMEM/F12 (1:1) media (Gibco) supplemented with 10% FCS at 37° C. in a 5% $CO_2$ humidified incubator.

Cells are seeded in 96-well plates at 2,000 cells/well and after 24 h they are exposed to different concentrations of compounds in 0.83% DMSO. Cells are grown for a further 2 h or 24 h, fixed with formaldehyde (2% final) and permeabilised with methanol. Following blocking with TBST-3% BSA, fixed cells are incubated with primary antibody (anti-phospho ERK from rabbit) over-night at 4° C. Cells are incubated with Propidium Iodide (DNA fluorescent dye) and detection of cellular p-ERK is performed using an anti-rabbit secondary antibody conjugated to the fluorescent Alexa Fluor 488 dye (Molecular probes). The fluorescence is analysed using the Acumen Explorer (TTP Labtech), a laser-scanning microplate cytometer, and the Alexa Fluor 488 signal is normalised to the PI signal (proportional to cell number).

The $EC_{50}$ is defined as the concentration at which a given compound achieves a signal half way between the baseline and the maximum response. $EC_{50}$ values are calculated using the XLfit software package (version 2.0.5).

In this assay, title compounds of EXAMPLES 5-14, 16-17, 20-22 and 24-27 exhibited an $EC_{50}$ of less than 0.1 μM in the HCT116 cell line. Title compounds of EXAMPLES 6-12, 14, 17 and 20-27 exhibited an $EC_{50}$ of less than 0.1 μM in the A375 cell line.

Synthesis of Hydroxylamines (S)-1-Aminooxy-propan-2-ol hydrochloride

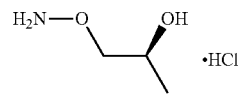

Step 1:
(S)-2-(tert-Butyl-dimethyl-silanyloxy)-propionic acid ethyl ester

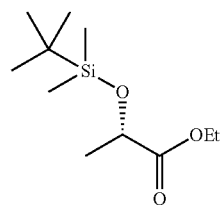

To a solution of (S)-(−)-ethyl lactate (37.4 g, 0.32 mol) in DCM (200 mL) was added imidazole (25.75 g, 0.38 mol) and TBSCl (50 g, 0.33 mol). The reaction mixture was stirred at room temperature for 2 hours. The reaction was diluted with water and extracted with DCM (2×50 mL), the combined organic extracts washed with brine dried (MgSO$_4$) and concentrated in vacuo to give the title product as a colourless oil (100%). $^1$H NMR (CDCl$_3$, 400 MHz) 4.21 (1 H, q, J=6.73 Hz), 4.14-4.01 (2H, m), 1.29 (3H, d, J=6.79 Hz), 1.18 (3H, t, J=7.09 Hz), 0.80 (9H, s), −0.01 (6H, s).

Step 2: (S)-2-(tert-Butyl-dimethyl-silanyloxy)-propan-1-ol

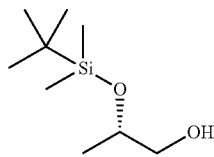

A 2M solution of LiBH$_4$ (2.77 g, 0.13 mol) in THF (60 mL) was added dropwise to a solution of (S)-2-(tert-butyl-dimethyl-silanyloxy)-propionic acid ethyl ester (22.75 g, 0.10 mol) and methanol (5.15 mL, 0.13 mol) in diethyl ether (500 mL) at 0° C. The reaction mixture was stirred at 0° C. for 1 hour and then at room temperature for 1.5 hours before cooling to 0° C. and carefully quenching with water. The reaction mixture was filtered and the filtrate extracted with diethyl ether (2×50 mL), the combined organic extracts were washed with brine, dried (MgSO$_4$) and concentrated in vacuo to give the title product as a colourless oil (18.2 g, 97%). $^1$H NMR (CDCl$_3$, 400 MHz) 3.86-3.77 (1H, m), 3.45-3.37 (1H, m), 3.31-3.22 (1H, m), 1.96-1.85 (1H, m), 1.03 (3H, d, J=6.23 Hz), 0.81 (9H, s), 0.00 (6H, s).

Step 3: 2-[(S)-2-(tert-Butyl-dimethyl-silanyloxy)-propoxy]isoindole-1,3-dione

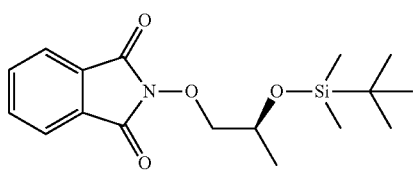 [SMILES: C[C@@H](CON1C(=O)c2ccccc2C1=O)O[Si](C)(C)C(C)(C)C]

To a suspension of (S)-2-(tert-butyl-dimethyl-silanyloxy)-propan-1-ol (53.0 g, 0.28 mol), N-hydroxyphthalimide (47.0 g, 0.29 mol) and triphenylphosphine (77.9 g, 0.30 mol) in THF (200 ml) at 0° C. was added dropwise DIAD (56.8 ml, 0.29 mol). During the addition the reagents dissolved and the solution turned a dark red colour before fading to pale yellow colour on completion of the addition. The reaction mixture was stirred and allowed to warm to room temperature overnight. The reaction mixture was concentrated in vacuo and the resultant residue re-dissolved in diethyl ether. The suspension was filtered and the filtrate was concentrated in vacuo to yield the crude title compound as a pale yellow oil. The material was used without further purification in the subsequent step.

Step 4: O—[(S)-2-(tert-Butyl-dimethyl-silanyloxy)-propyl]hydroxylamine

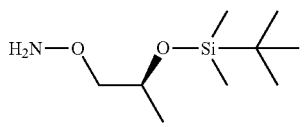

To a cold solution of crude 2-[(S)-2-(tert-butyl-dimethyl-silanyloxy)-propoxy]-isoindole-1,3-dione (0.28 mol) in DCM (200 ml) at 0° C. was added methyl hydrazine (14.74 mol, 0.28 mol). The reaction mixture was stirred at 0° C. for 30 minutes then filtered and the filtrate concentrated in vacuo. The resultant residue was subjected to distillation (b.p. 108-112° C. at 2-10 mbar) to yield the title compound as a colourless oil. (42.63 g, 74% from ethyl lactate). $^1$H NMR (CDCl$_3$, 400 MHz) 5.36 (2H, s), 3.95 (1H, m), 3.55-3.41 (2H, m), 1.04 (3H, d, J=6.28 Hz), 0.81 (9H, s), 0.02 (6H, m).

Step 5: (S)-1-Aminooxy-propan-2-ol hydrochloride

O—[(S)-2-(tert-Butyl-dimethyl-silanyloxy)-propyl]-hydroxylamine (6.56 g, 31.9 mmol) was dissolved in IMS (20 mL) and 12N HCl added (2.79 mL, 33 5 mmol), the reaction mixture stirred at room temperature for 1.5 hours. The reaction mixture was concentrated in vacuo and the resultant residue crystallised from IPA/diethyl ether (1:1) to give the title compound as fine white needles (3.2 g, 79%). $^1$H NMR (DMSO-d$_6$, 400 MHz) 10.93 (3H, s), 3.94-3.80 (2H, m), 2.51-2.48 (1H, m), 1.07-1.02 (3H, d, J=6.01 Hz).

(S)-1-aminooxypropan-2-ol hydrochloride

Alternate Method

Step 1: 2-((S)-2-hydroxy-propoxy)-isoindole-1,3-dione

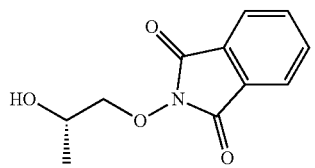 [SMILES: C[C@H](O)CON1C(=O)c2ccccc2C1=O]

To a suspension of N-hydroxyphthalimide (250 g, 1.53 mol), toluene (450 mL), tetrabutylammonium bromide (24.7 g, 76.6 mmol) and (S)-(−)-propylene oxide (214.7 mL, 3.07 mol) was added DIPEA (13.3 mL, 76.6 mmol). The reaction mixture was heated under nitrogen at reflux for 3 hours. The reaction mixture was concentrated in vacuo to obtain a yellow solid. The solid was dissolved in hot ethyl acetate and loaded onto a plug of flash silica (600 g) and the product eluted with diethyl ether (4 L). The ether solution was concentrated in vacuo to yield a pale yellow solid. The solid was dissolved in ethyl acetate (150 mL) at 75° C. and cyclohexane (300 mL) added. The solution was allowed to cool down to room temperature with stirring, causing a white solid to crystallise from the solution. The crystals were collected by filtration, wash-

Step 2: (S)-1-aminooxypropan-2-ol hydrochloride

A solution of 2-((S)-2-hydroxypropoxy)-isoindole-1,3-dione (20 g, 90.4 mmol) and aqueous hydrochloric acid (150 mL, 6N, 0.9 mol) was stirred at room temperature for 16 hours giving a white suspension. The reaction mixture was filtered and the filtrate concentrated in vacuo to give a white solid. The resultant residue was crystallised from hot IPA/cyclohexane (10 mL/20 mL) to give the product (S)-1-aminooxypropan-2-ol hydrochloride as a white crystalline solid (7.78 g, 67%). $^1$H NMR (DMSO-d$_6$, 400 MHz) 10.82 (2H, bs), 3.92-3.78 (3H, m), 1.06 (3H, d, J=6.2 Hz).

2-Aminooxy-2-methyl-propan-1-ol hydrochloride

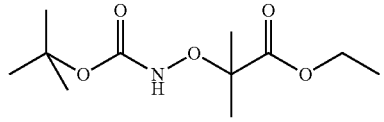

Step 1: 2-(N-Boc-aminooxy)isobutyric acid ethyl ester

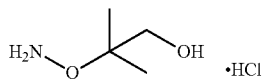

To a solution of N-Boc-hydroxylamine (5.2 g, 39.05 mmol) in ethanol (100 mL) was added potassium hydroxide (2.63 g, 46.86 mmol), the mixture stirred at room temperature until a solution was formed. 2-Bromoisobutyric acid ethyl ester (6.87 mL, 46.9 mmol) was added and the reaction mixture heated at reflux for 18 hours. The reaction mixture was cooled to room temperature then filtered, and the filtrate was concentrated in vacuo. The resultant oily residue was partitioned between water (75 mL) and diethyl ether and the aqueous fraction was extracted with diethyl ether (2×100 mL). The combined organic extracts were dried (Na$_2$SO$_4$), filtered and concentrated in vacuo to give the title compound as a clear oil (9.5 g, 99%). LCMS (method C): R$_f$=2.55 min, [M+H]$^+$=248. $^1$H NMR (CDCl$_3$, 400 MHz) 4.20 (q, 2H), 1.50 (s, 6H), 1.49 (s, 9H), 1.30 (t, 3H).

Step 2: 2-(N-Boc-aminooxy)-2-methylpropan-1-ol

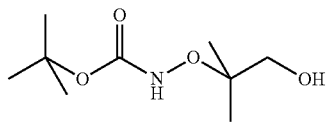

To a solution of 2-(N-Boc-aminooxy)isobutyric acid ethyl ester (2.35 g, 9.5 mmol) in anhydrous ethyl ether (100 mL) at 0° C. under nitrogen was added 1.0 M lithiumtetrahydroaluminate in tetrahydrofuran (17.1 mL, 17 mmol), and the reaction mixture stirred at 0° C. for 5 hours. The reaction mixture was quenched with water (25 mL) and allowed to warm to room temperature. The suspension was filtered and the residue washed with diethyl ether and layers separated. The organic extract was dried (Na$_2$SO$_4$), filtered and concentrated in vacuo to give the title compound as a white solid (1.94 g, 99%). $^1$H NMR (CDCl$_3$, 400 MHz) 3.40 (s, 2H), 1.50 (s, 9H), 1.20 (s, 6H).

Step 3: 2-Aminooxy-2-methyl-propan-1-ol hydrochloride

To a solution of 2-(N-Boc-aminooxy)-2-methylpropan-1-ol (1.94 g, 9.45 mmol) in anhydrous dichloromethane (10 mL) was added 4 M HCl in dioxane (47.3 mL, 200 mmol) and the mixture stirred at room temperature for 1 hour. The reaction mixture was concentrated in vacuo and the residue triturated with ether (3×30 mL) to give the title compound as an white solid (1.10 g, 82%). $^1$H NMR (DMSO-d$_6$, 400 MHz) 3.58 (s, 2H), 3.48 (s, 2H), 1.34 (s, 6H).

Synthesis of Anilines

2-Fluoro-4-trimethylsilanyl-phenylamine

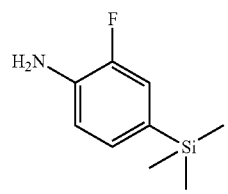

Method A, Step 1:
(3-Fluoro-4-nitro-phenyl)-trimethylsilane

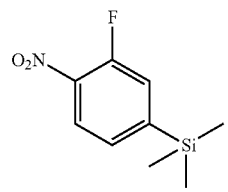

4-Chloro-2-fluoro-1-nitro-benzene (97.2 g, 0.55 mol) was dissolved in xylenes (208 ml) and hexamethyldisilane (306 g, 2.78 mol) was added. Argon was bubbled through the mixture for 20 minutes, then Pd(PPh₃)₄ (16.2 g, 14 mmol) was added and the mixture was heated under continuous flow of argon at 150° C. for 1 hour. A balloon filled with argon was then fitted and the mixture was heated at 150° C. for a further 60 hours. After cooling the mixture was diluted with Et₂O and filtered through a 4 cm silica pad. The filter cake was washed with further Et₂O, and the combined organic residues were concentrated in vacuo. Purification of the resultant residue by flash chromatography (SiO₂, eluent 98:1:1 pentane:CH₂Cl₂: Et₂O) gave 76.7 g of the title compound as an orange oil and also mixed fractions. The mixed fractions were combined and concentrated, then distilled (110° C., 6 mbar) to give a further 7.2 g of the title compound (overall 83.9 g, 71%). ¹H NMR (DMSO-d₆) 0.30 (9H, s), 7.56 (1H, d, J=8.02 Hz), 7.67 (1H, dd, J=11.49, 1.14 Hz), 8.10 (1H, t, J=7.66 Hz).

Method A, Step 2:
2-Fluoro-4-trimethylsilanyl-phenylamine

A slurry of 10% wt. palladium on carbon (4.0 g) in IMS (25 mL) was added to a solution of (3-fluoro-4-nitro-phenyl)-trimethylsilane (62.0 g, 0.29 mol) in IMS (250 mL) and the reaction mixture flushed with nitrogen five times then hydrogen three times. The reaction mixture was then stirred under 3 bar pressure of hydrogen at room temperature for 4 hours. The reaction mixture was then purged with nitrogen again before filtering through a pad of Celite® with ethyl acetate washings. The filtrate was concentrated under reduced pressure to give the title compound as a light brown oil (53.0 g, quantitative). 1H NMR (CDCl₃, 400 MHz) 7.16-7.09 (1H, m), 7.10 (1H, d, J=7.75 Hz), 6.81 (1H, t, J=8.16 Hz), 3.78 (2H, s), 0.26 (9H, s).

Method B, 2-Fluoro-4-trimethylsilanyl-phenylamine

To a solution of 4-bromo-2-fluoro-phenylamine (114 g, 0.6 mol) in anhydrous THF (750 mL) under inert atmosphere at −78° C. was added a 1.6M solution of nBuLi in hexanes (1500 mL, 2.4 mol) dropwise keeping the internal temperature below −60° C. The reaction mixture was treated dropwise with TMSCl (256 mL, 2.0 mol), keeping the internal temperature below −60° C. The reaction mixture was allowed to warm to 0° C. over a 1 hour period and poured into ice-cold 2M HCl (ca 1 L). The mixture was vigorously stirred for 10 min, then the organic layer was separated, washed with water followed by a saturated solution of potassium carbonate, dried (Na₂SO₄), filtered and concentrated to give the title compound as a light brown oil (89 g, 81%).

4-Cyclopropyl-2-fluoro-phenylamine

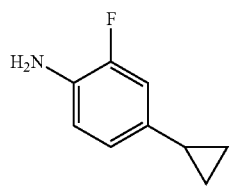

Step 1: Trifluoro-methanesulfonic acid
3-fluoro-4-nitro-phenyl ester

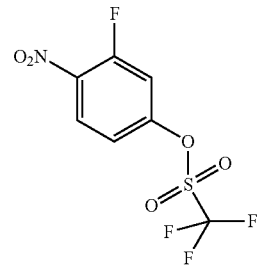 [SMILES: O=[N+]([O-])c1ccc(OS(=O)(=O)C(F)(F)F)cc1F]

To a solution of 3-fluoro-4-nitrophenol (12.5 g, 80 mmol) and trifluoromethane sulfonic anhydride (26.8 mL, 160 mmol) in DCM (300 mL) at 0° C. was added triethylamine (44.6 mL, 320 mmol) dropwise. The reaction mixture was stirred at 0° C. for 2 hours then allowed to warm to room temperature and stirred for 18 hours. The reaction was quenched by the addition of water and the mixture extracted with DCM. The organic layer was separated, washed with water and then dried (MgSO₄), filtered and concentrated in vacuo. The resultant residue was subjected to flash chromatography (Si—PPC, gradient 0 to 40% ethyl acetate in cyclohexane) to give the title compound as a yellow oil (12.8 g, 56% yield). ¹H NMR (DMSO-d₆, 400 MHz) 8.39 (1 H, t, J=8.83 Hz), 8.12 (1 H, dd, J=11.09, 2.65 Hz), 7.67 (1 H, ddd, J=9.20, 2.62, 1.52 Hz).

Step 2: 4-Cyclopropyl-2-fluoro-1-nitro-benzene

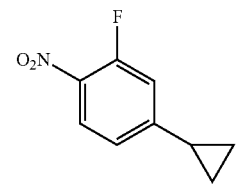 [SMILES: O=[N+]([O-])c1ccc(C2CC2)cc1F]

A stirred suspension of trifluoro-methanesulfonic acid 3-fluoro-4-nitro-phenyl ester (5.6 g, 19 mmol), cyclopropyl boronic acid (2.09 g, 23.3 mmol) Pd(dppf)Cl₂ (1.24 g, 1.5 mmol) and 2M aqueous cesium carbonate (30 mL, 60 mmol) in toluene (20 mL) was degassed before being heated at 90° C. under an argon atmosphere for 2.5 hours. The reaction mixture was allowed to cool to room temperature before filtering through a pad of Celite®, washing with ethyl acetate. The filtrate was washed (water, brine), and then dried (MgSO₄), filtered and concentrated in vacuo. The resultant residue was subjected to flash chromatography (Si—PPC, gradient 0-30% ethyl acetate in pentane) to give the title compound as a yellow solid (2.79 g, 81%). ¹H NMR (DMSO-d₆, 400 MHz) 8.03 (1 H, t, J=8.39 Hz), 7.28 (1 H, dd, J=13.19, 1.91 Hz), 7.16 (1 H, dd, J=8.61, 1.90 Hz), 2.14-2.05 (1 H, m), 1.21-1.05 (2 H, m), 0.92-0.82 (2 H, m).

Step 3: 4-Cyclopropyl-2-fluoro-phenylamine

A slurry of palladium on carbon (200 mg, 10% wt.) in IMS was added to a degassed solution of 4-cyclopropyl-2-fluoro-1-nitro-benzene (1.45 g, 8 mmol) in IMS (50 mL), the atmosphere was evacuated and back-filled with nitrogen then re-evacuated and back-filled with hydrogen. The reaction mixture was stirred under 1 atmosphere pressure of hydrogen at room temperature for 24 hours before filtering through a pad of Celite® then washing with ethyl acetate. The filtrate was concentrated in vacuo to give the title compound as a pale purple residue (1.19 g, 98%). $^1$H NMR (CDCl$_3$, 400 MHz) 6.72-6.63 (3 H, m), 3.56 (2 H, s), 1.83-1.75 (1 H, m), 0.93-0.82 (2 H, m), 0.59-0.54 (2 H, m).

Synthesis of Intermediate Heterocyclic Cores

4-Chloro-1-(toluene-4-sulfonyl)-1H-indazole-5-carboxylic acid methyl ester and 4-chloro-2-(toluene-4-sulfonyl)-1H-indazole-5-carboxylic acid methyl ester

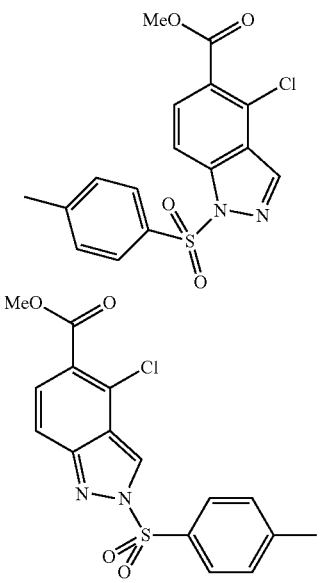

Step 1: 4-Amino-2-chloro-3-methyl-benzoic acid methyl ester

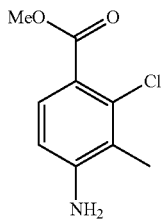

To a suspension of 4-amino-2-chloro-3-methyl-benzoic acid (0.64 g, 3.45 mmol) in toluene (10 mL) and methanol (10 mL) at 0° C. was added drop-wise trimethylsilyldiazomethane (3.45 mL, 2 M in hexane, 6.90 mmol). The reaction mixture was stirred at 0° C. for 30 min during which the reagents dissolved. The reaction mixture was quenched by the addition of acetic acid (1 mL) then washed with aqueous saturated sodium bicarbonate solution (10 mL) and the aqueous fraction extracted twice with ethyl acetate (2×10 mL). The combined organic extracts were washed with brine (20 mL), dried (MgSO$_4$) and concentrated in vacuo to give the title compound as a beige solid (0.66 g, 96%). $^1$H NMR (CDCl$_3$, 400 MHz) 2.26 (3H, s), 3.86 (3H, s), 6.55 (1H, d, J=8.8 Hz), 7.60 (1H, d, J=8.8 Hz).

Step 2: 4-Chloro-1H-indazole-5-carboxylic acid methyl ester

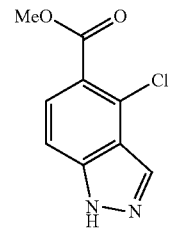 [SMILES: COC(=O)c1ccc2[nH]ncc2c1Cl]

To a solution of 4-amino-2-chloro-3-methyl-benzoic acid methyl ester (5.29 g, 26.5 mmol) in acetic acid (100 mL) was added isoamylnitrite (3.9 mL, 29.2 mmol). The reaction mixture was stirred at room temperature for 30 minutes then heated at reflux for 3 hours. The reaction mixture was concentrated in vacuo and the resultant residue subjected to flash chromatography (SiO$_2$, gradient 0-100% ethyl acetate in cyclohexane) to yield the title compound as an off-white solid (2.26 g, 40%). $^1$H NMR (CDCl$_3$, 400 MHz) 3.97 (3H, s), 7.42 (1H, d, J=8.8 Hz), 7.95 (1H, d, J=8.8 Hz), 8.29 (1H, s).

Step 3: 4-Chloro-1-(toluene-4-sulfonyl)-1H-indazole-5-carboxylic acid methyl ester and 4-chloro-2-(toluene-4-sulfonyl)-1H-indazole-5-carboxylic acid methyl ester To a solution of 4-chloro-1H-indazole-5-carboxylic acid methyl ester (1 g, 4.74 mmol) in THF (20 mL) was added p-toluenesulfonyl chloride (1.0 g, 5 2 mmol), triethylamine (0.8 mL, 5.7 mmol) and DMAP (catalytic). The reaction mixture was stirred at room temperature for 16 hours during which a white precipitate formed. The reaction mixture was diluted with water and extracted with ethyl acetate (3×20 mL). The combined organic fractions were washed with brine (20 mL), dried (MgSO$_4$) and concentrated in vacuo. The resultant residue was subjected to flash chromatography (SiO$_2$, gradient 0-80% ethyl acetate in cyclohexane) to yield the title compounds as an off-white solid (1.51 g, 82%). $^1$H NMR showed the product to be a 1:1 mixture of isomers. LCMS (Method B): R$_T$=4.02 min, [M–H]$^-$=363.

4-Bromo-indazole-1,5-dicarboxylic acid di-tert-butyl ester

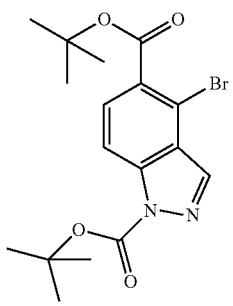 [SMILES: CC(C)(C)OC(=O)c1ccc2c(cnn2C(=O)OC(C)(C)C)c1Br]

Step 1: 2-Bromo-4-fluoro-benzoic acid tert-butyl ester

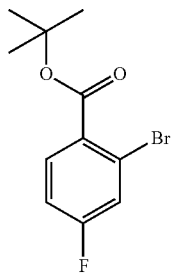

To a suspension of 2-bromo-4-fluoro-benzoic acid (28.5 g, 0.13 mol) in dichloromethane (500 mL) at room temperature was added oxalyl chloride (11.35 mL, 0.26 mmol) followed by DMF (0.05 mL, catalytic, CARE vigorous gas evolution) and the reaction mixture stirred for 3 hours. The reaction mixture was concentrated in vacuo and the residue dissolved in DCM (500 mL) before treatment with a solution of tert-butanol (28.5 g, 0.26 mol) and pyridine (20.5 g, 0.26 mol). The resultant mixture was stirred at room temperature for 3 days before it was diluted with DCM and washed (1M aqueous sodium hydroxide, water, 0.1M aqueous HCl, water) dried (Na$_2$SO$_4$) filtered and concentrated in vacuo to give a yellow oil. The crude oil was subjected to flash chromatography (Si—PPC, gradient 0 to 20% ethyl acetate in cyclohexane) to give the title compound as a colourless oil (15.2 g, 42%). $^1$H NMR (CDCl$_3$, 400 MHz) 7.76-7.73 (1H, m), 7.37 (1H, dd, J=8.36, 2.53 Hz), 7.05 (1H, ddd, J=8.70, 7.73, 2.53 Hz), 1.60 (9 H, s).

Step 2: 2-Bromo-4-fluoro-3-formyl-benzoic acid tert-butyl ester

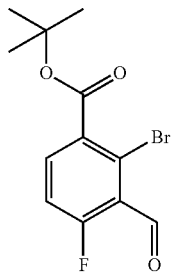 [SMILES: CC(C)(C)OC(=O)c1ccc(F)c(C=O)c1Br]

To a solution of 2-bromo-4-fluoro-benzoic acid tert-butyl ester (10.0 g, 36 mmol) in THF (100 mL) at −78° C. under an atmosphere of nitrogen was added lithium diisopropylamide (1.8M solution, 20 mL, 36 mmol) dropwise. The reaction mixture was stirred for 1.25 hours before adding DMF (10 mL) then stirred for a further 10 minutes before quenching with acetic acid (3 mL). The products were partitioned between ethyl acetate and water, the organic layer was separated, washed with brine, dried (Na$_2$SO$_4$), filtered and concentrated in vacuo to give a yellow oil which crystallized on standing. The crude product was triturated in cyclohexane to give the title compound as a yellow solid (6.8 g, 62%). $^1$H NMR (CDCl$_3$, 400 MHz) 10.38 (1H, s), 7.80-7.73 (1H, m), 7.17 (1H, t, J=9.09 Hz), 1.62 (9H, s).

Step 3: 4-Bromo-1H-indazole-5-carboxylic acid tert-butyl ester

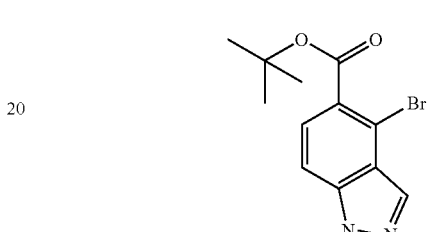

A bi-phasic solution of 2-bromo-4-fluoro-3-formyl-benzoic acid tert-butyl ester (4.25 g, 14 mmol), DME (25 mL) and hydrazine hydrate (15 mL) was heated at 90° C. for 1 hour. After cooling, the products were partitioned between ethyl acetate and water, the aqueous layer extracted with ethyl acetate and the combined organic extracts dried (Na$_2$SO$_4$), filtered and concentrated in vacuo to give the title compound as a tan solid (4.1 g, 100%). LCMS (method B) R$_T$=3.63 min, [M+CH$_3$CN+H]$^+$=338/340, [M−H]$^-$=295/297.

Step 4: 4-Bromo-indazole-1,5-dicarboxylic acid di-tert-butyl ester

To a solution of 4-bromo-1H-indazole-5-carboxylic acid tert-butyl ester (3.0 g, 10 mmol), and triethylamine (1.53 mL, 11 mmol) in DCM (30 mL) was added di-tert-butyl-dicarbonate (2.4 g, 11 mmol) and the reaction mixture stirred at room temperature for 4 hours. The reaction mixture was diluted with DCM, washed (saturated aqueous NaHCO$_3$, water), dried (Na$_2$SO$_4$), filtered and concentrated in vacuo to give a yellow/orange oil which crystallized on standing. The crude product was triturated in pentane to give the title compound as an off-white/yellow solid (1.8 g, 45%). $^1$H NMR (CDCl$_3$, 400 MHz) 8.29 (1H, s), 8.18-8.10 (1H, m), 7.92 (1H, d, J=8.74 Hz), 1.70 (9H, s), 1.63 (9H, s).

4-Bromo-benzo[d]isothiazole-5-carboxylic acid tert-butyl ester

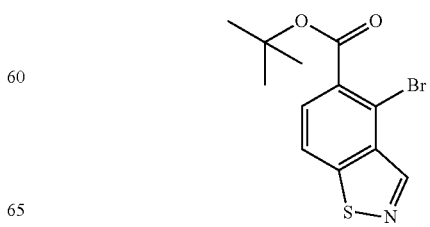

Step 1: 4-Benzylsulfanyl-2-bromo-3-formyl-benzoic acid tert-butyl ester

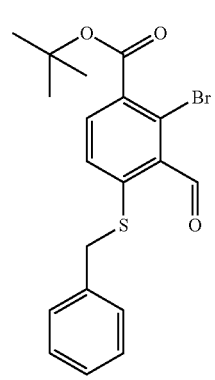 [SMILES: CC(C)(C)OC(=O)c1ccc(SCc2ccccc2)c(C=O)c1Br]

To a solution of potassium tert-butoxide (318 mg, 2.84 mmol) in THF (20 mL) under an atmosphere of nitrogen was added benzene methane thiol (332 µL, 2.84 mmol) and the mixture stirred at room temperature for 10 minutes. 2-Bromo-4-fluoro-3-formyl-benzoic acid tert-butyl (860 mg, 2.84 mmol) was added and stirring continued for 30 minutes before quenching with a saturated aqueous solution of NH$_4$Cl. The products were partitioned between ethyl acetate and water, the organic layer separated, washed with brine, dried (Na$_2$SO$_4$), filtered and concentrated in vacuo to give the title compound as a yellow solid (1.15 g, 100%). $^1$H NMR (CDCl$_3$) 10.57 (1H, s), 7.61 (1H, d, J=8.44 Hz), 7.40-7.25 (6H, m), 4.17 (2H, s), 1.61 (9 H, s).

Step 2: 4-Bromo-benzo[d]isothiazole-5-carboxylic acid tert-butyl ester

To a cold (0° C.) solution of 4-benzylsulfanyl-2-bromo-3-formyl-benzoic acid tert-butyl ester (1.15 g, 2.82 mmol) in DCM (15 mL) was added sulfuryl chloride (453 µL, 5.64 mmol) and the reaction mixture stirred at room temperature for 18 hours. The reaction mixture was concentrated under reduced pressure and the residue azeotroped with THF (×2) and then dissolved in THF (7 mL). The resultant solution was cooled to 0-5° C. and a solution of ammonia in methanol (2M, 15 mL) was added dropwise. The reaction mixture was stirred cold for 30 minutes then at room temperature for 18 hours. The reaction mixture was concentrated under reduced pressure and the residue partially dissolved in diethyl ether. The ethereal solution was concentrated in vacuo and the residue subjected to flash chromatography (Si—PPC, gradient 0-10% diethyl ether in pentane) to give the title compound as a colourless oil (523 mg, 59%). $^1$H NMR (CDCl$_3$) 9.13 (1H, d, J=0.88 Hz), 7.89 (1H, dd, J=8.36, 0.97 Hz), 7.83 (1H, d, J=8.37 Hz), 1.61 (9 H, s).

7-Fluoro-benzo[d]isothiazole-6-carboxylic acid

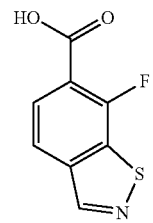 [SMILES: O=C(O)c1ccc2cnsc2c1F]

Step 1: 2,3-Difluoro-4-methyl-benzoic acid tert-butyl ester

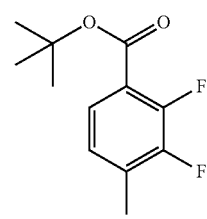 [SMILES: Cc1ccc(C(=O)OC(C)(C)C)c(F)c1F]

A mixture of 2,3-difluoro-4-methyl-benzoic acid (20.0 g, 116 mmol), di-tert-butyl dicarbonate (25.0 g, 116 mmol) and DMAP (2.0 g, 16.4 mmol) in tert-butanol (500 mL) was stirred at 45° C. for 5 hours before being concentrated in vacuo. The resultant residue was triturated in Et$_2$O and filtered. The filtrate was concentrated in vacuo to give a residue which was partitioned between ethyl acetate and a 1M aqueous solution of hydrochloric acid. The organic layer was separated and washed with a saturated aqueous solution of sodium hydrogen carbonate followed by brine, dried (Na$_2$SO$_4$), filtered and evaporated in vacuo to give the title compound as a colourless oil (17.3 g, 65%). $^1$H NMR (CDCl$_3$, 400 MHz) 7.51 (1 H, ddd, J=8.3, 6.6, 1.9 Hz), 6.95 (1 H, m), 2.33 (3 H, d, J=2.3 Hz), 1.59 (9 H, s).

Step 2: 4-Bromomethyl-2,3-difluoro-benzoic acid tert-butyl ester

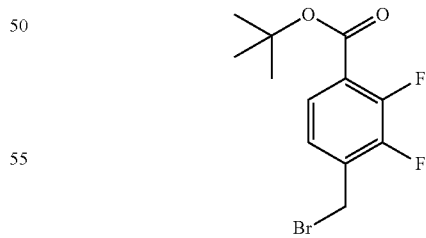

A solution of 2,3-difluoro-4-methyl-benzoic acid tert-butyl ester (17.3 g, 75.9 mmol) and N-bromosuccinimide (13.5 g, 75.9 mmol) in carbon tetrachloride (250 mL) was degassed for 10 minutes. AIBN (1.2 g, 7.32 mmol) was added and the reaction mixture was stirred at reflux for 18 hours before being cooled to room temperature and filtered. The filtrate was concentrated in vacuo to give a residue which was subjected to flash chromatography (Si—PPC, gradient 0% to 10%, TBME in cyclohexane) to afford the title compound as a colourless oil (16.7 g, contaminated by 25% of starting material). ¹H NMR (CDCl₃, 400 MHz) 7.61 (1 H, ddd, J=8.3, 6.4, 2.1 Hz), 7.18 (1 H, ddd, J=8.1, 6.4, 1.8 Hz), 4.49 (2 H, d, J=1.3 Hz), 1.59 (9 H, s).

Step 3: 2,3-Difluoro-4-formyl-benzoic acid tert-butyl ester

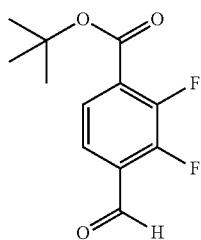 [SMILES: CC(C)(C)OC(=O)c1ccc(C=O)c(F)c1F]

To a solution of 4-bromomethyl-2,3-difluoro-benzoic acid tert-butyl ester (12.9 g, 42.1 mmol) in DMSO (80 mL) and DCM (40 mL) at 0° C. was added trimethylamine N-oxide (3.4 g, 45.3 mmol). The reaction mixture was stirred at room temperature for 18 hours before being concentrated in vacuo. The resultant residue was partitioned between iced water and ethyl acetate. The organic layer was separated and washed with brine twice, dried (Na₂SO₄), filtered and evaporated in vacuo. The resultant residue which was subjected to flash chromatography (Si—PPC, gradient 0% to 10%, TBME in cyclohexane) to afford the title compound as a white solid (4.34 g, 43%). ¹H NMR (CDCl₃, 400 MHz) 10.38 (1 H, d, J=0.8 Hz), 7.71 (1 H, dddd, J=7.4, 5.6, 1.7, 0.8 Hz), 7.63 (1 H, ddd, J=7.4, 5.6, 1.5 Hz), 1.61 (9 H, s).

Step 4: 3-Benzylsulfanyl-2-fluoro-4-formyl-benzoic acid tert-butyl ester

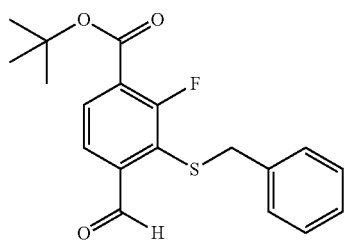 [SMILES: CC(C)(C)OC(=O)c1ccc(C=O)c(SCc2ccccc2)c1F]

To a solution of potassium tert-butoxide (2.0 g, 17.9 mmol) in anhydrous THF (80 mL) was added benzyl mercaptan (2.1 mL, 17.9 mmol). The reaction mixture was stirred at room temperature for 5 minutes before being cooled to −30° C. A solution of 2,3-difluoro-4-formyl-benzoic acid tert-butyl ester (4.34 g, 17.9 mmol) in anhydrous THF (20 mL) was added dropwise over 15 minutes and the resultant mixture was stirred at −30° C. for 30 minutes before being quenched by addition of water and extracted with ethyl acetate. The organic layer was separated, washed with water followed by brine, dried (Na₂SO₄), filtered and evaporated in vacuo to give the title compound as a yellow oil (6.2 g, 100%). ¹H NMR (CDCl₃, 400 MHz) 10.20 (1 H, d, J=0.6 Hz), 7.84 (1 H, ddd, J=8.0, 6.8, 0.7 Hz), 7.59 (1 H, dd, J=8.0, 0.9 Hz), 7.19 (3 H, m), 7.05 (2 H, m), 4.07 (2 H, s), 1.63 (9 H, s).

Step 5: 7-Fluoro-benzo[d]isothiazole-6-carboxylic acid tert-butyl ester

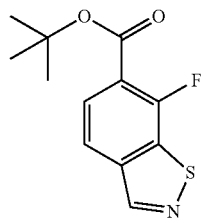 [SMILES: CC(C)(C)OC(=O)c1ccc2cnsc2c1F]

To a solution of 3-benzylsulfanyl-2-fluoro-4-formyl-benzoic acid tert-butyl ester (6.20 g, 17.9 mmol) in DCM (100 mL) was added sulfuryl chloride (2.9 mL, 35.8 mmol). The reaction mixture was stirred at room temperature for 1 hour before being concentrated in vacuo. The resultant residue was azeotroped with toluene twice and then taken up in THF (50 mL). The resultant solution was cooled to 0° C. and a 2M solution of ammonia in methanol (100 mL) was added. The reaction mixture was stirred at room temperature for 1 hour and then concentrated in vacuo. The resultant residue was partitioned between ethyl acetate and a saturated aqueous solution of sodium hydrogen carbonate. The organic layer was separated and washed with water followed by brine, dried (Na₂SO₄), filtered and evaporated in vacuo. The residue was subjected to flash chromatography (Si—PPC, gradient 0% to 10%, Et₂O in pentane) to afford the title compound as a yellow solid (2.96 g, 65%). ¹H NMR (CDCl₃, 400 MHz) 8.93 (1 H, dd, J=4.1, 0.5 Hz), 7.91 (1 H, ddd, J=8.3, 5.8, 0.5 Hz), 7.84 (1 H, d, J=8.3 Hz), 1.64 (9 H, s).

Step 6: 7-Fluoro-benzo[d]isothiazole-6-carboxylic acid

To a solution of 7-fluoro-benzo[d]isothiazole-6-carboxylic acid tert-butyl ester (1.0 g, 4.0 mmol) in DCM (10 mL) was added water (0.2 mL) and TFA (10 mL). There reaction mixture was stirred at room temperature for 1 hour and concentrated in vacuo. The residue was azeotroped with toluene to give the title compound as a yellow solid (788 mg, 100%). LCMS (method B): R$_T$=2.86 min, [M−H]⁻=196.

Synthesis of Phenylamino Acids 4-(2-Fluoro-4-iodo-phenylamino)-1-(toluene-4-sulfonyl)-1H-indazole-5-carboxylic acid

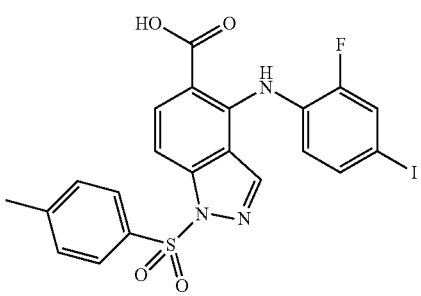 [SMILES: Cc1ccc(S(=O)(=O)n2ncc3c(Nc4ccc(I)cc4F)c(C(=O)O)ccc32)cc1]

Step 1: 4-(2-Fluoro-4-trimethylsilanylphenylamino)-1-(toluene-4-sulfonyl)-1H-indazole-5-carboxylic acid methyl ester

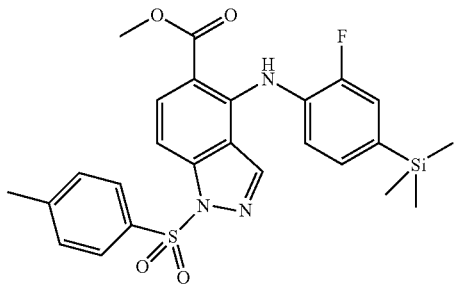

4-Chloro-1-(toluene-4-sulfonyl)-1H-indazole-5-carboxylic acid methyl ester and 2-[1-chloro-1-[3-methyl-1-(toluene-4-sulfonyl)-1H-pyrazol-4-yl]-meth-(Z)-ylidene]-but-3-enoic acid methyl ester (1.1 g, 3.0 mmol), 2-fluoro-4-trimethylsilanylphenylamine (0.61 g, 3.3 mmol), 2-dicyclohexylphosphino-2'-6'-diisopropyl biphenyl (0.28 g, 0.60 mmol), potassium phosphate (0.70 g, 3.3 mmol) and tris(dibenzylideneacetone)dipalladium (0) (87 mg, 0.15 mmol) were suspended in toluene (5 mL) and the resultant mixture degassed. The reaction mixture was heated at 105° C. for 3 hours. The reaction was quenched by the addition of hydrochloric acid (1M, 5 mL) and the resultant mixture extracted with ethyl acetate (3×20 mL). The combined organic extracts were washed with brine (20 mL), dried (MgSO$_4$) and concentrated in vacuo. The resultant residue was subjected to flash chromatography (Si—SPE, gradient 0-100% DCM in cyclohexane) to yield the title compound as a pale brown solid (0.78 g, 50%). $^1$H NMR showed the product to be a single isomer. LCMS (Method B): R$_T$=5.22 min, [M+H]$^+$=512.

Step 2: 4-(2-Fluoro-4-iodophenylamino)-1-(toluene-4-sulfonyl)-1H-indazole-5-carboxylic acid methyl ester

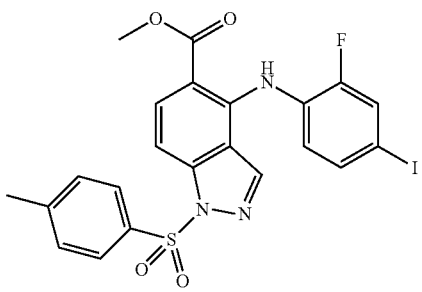 [SMILES: COC(=O)c1ccc2c(cnn2S(=O)(=O)c2ccc(C)cc2)c1Nc1ccc(I)cc1F]

To a solution of 4-(2-fluoro-4-trimethylsilanylphenylamino)-1-(toluene-4-sulfonyl)-1H-indazole-5-carboxylic acid methyl ester (0.56 g, 1.1 mmol) in DCM (3 mL) at 0° C. was added a solution of iodine monochloride in DCM (2.2 mL, 1M, 2.2 mmol). The reaction mixture was stirred at 0° C. for 30 minutes. The reaction was quenched by the addition of water (10 mL) then diluted with saturated aqueous sodium thiosulfate solution (10 mL). The resultant mixture was extracted with ethyl acetate (3×20 mL) and the combined organic fractions washed with brine (20 mL), dried (MgSO$_4$) then concentrated in vacuo. The resultant residue was subjected to flash chromatography (SiO$_2$, gradient 0-100% DCM in cyclohexane) to yield the title compound as a light brown solid (0.51 g, 83%). LCMS (Method B): R$_T$=4.87 min, [M+H]$^+$=566.

Step 3: 4-(2-Fluoro-4-iodo-phenylamino)-1-(toluene-4-sulfonyl)-1H-indazole-5-carboxylic acid To a solution of 4-(2-fluoro-4-iodophenylamino)-1-(toluene-4-sulfonyl)-1H-indazole-5-carboxylic acid methyl ester (0.51 g, 0.91 mmol) in toluene (5 mL) was added bis(tributyltin) oxide (0.92 mL, 1.8 mmol) and the reaction mixture heated at reflux for 48 hours. The reaction mixture was concentrated in vacuo and the resultant residue subjected to flash chromatography (Si—PPC, gradient 0-10% methanol in DCM) to yield the title compound as a light brown solid (0.46 g, 92%). LCMS (Method B): R$_T$=4.27 min, [M+H]$^+$=552.

4-(2-Fluoro-4-iodophenylamino)-1-(4-methoxybenzyl)-1H-pyrazolo[3,4-b]pyridine-5-carboxylic acid

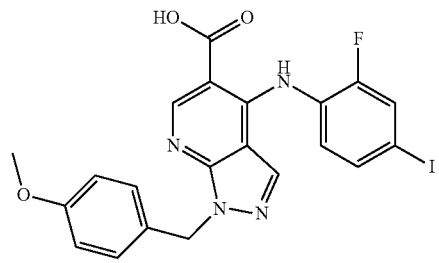 [SMILES: COc1ccc(Cn2ncc3c(Nc4ccc(I)cc4F)c(C(=O)O)cnc32)cc1]

Step 1: 4-(2-Fluoro-4-iodophenylamino)-1-(4-methoxybenzyl)1H-pyrazolo[3,4-b]pyridine-5-carboxylic acid ethyl ester

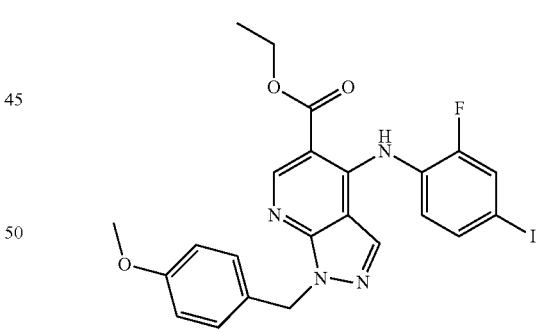

4-Chloro-1-(4-methoxy-benzyl)-1H-pyrazolo[3,4-b]pyridine-5-carboxylic acid ethyl ester (1.8 g, 5.2 mmol) and 2-fluoro-4-iodoaniline (1.5 g, 6.3 mmol) were dissolved in dioxane (20 mL) and the resultant mixture stirred at reflux for 16 hours. The reaction mixture was diluted with water (50 mL) and the aqueous layer extracted with dichloromethane (3×20 mL). The combined organic fractions were filtered through a hydrophobic frit and concentrated in vacuo. The resultant residue was subjected to flash chromatography (Si—PPC, gradient 0-30% ethyl acetate in cyclohexane) to yield the title compound as a white solid (1.56 g, 56%). LCMS (Method B): R$_T$=4.78 min, [M+H]$^+$=547.

Step 2: 4-(2-Fluoro-4-iodophenylamino)-1-(4-methoxybenzyl)-1H-pyrazolo[3,4-b]pyridine-5-carboxylic acid To a suspension of 4-(2-fluoro-4-iodophenylamino)-1-(4-methoxybenzyl)-1H-pyrazolo[3,4-b]pyridine-5-carboxylic acid ethyl ester (380 mg, 0.71 mmol) in IMS (10 mL) was added aqueous sodium hydroxide solution (1.78 mL, 1M, 1.78 mmol). The reaction mixture was heated at 65° C. for 2 hours, during which time all solids dissolved. Volatile solvents were removed in vacuo and the resultant solution was acidified to pH ~3 by careful addition of aqueous hydrochloric acid (1M) causing a precipitate to form. The precipitate was collected by filtration and dried under vacuum at 45° C. to yield the title compound as a brown solid (360 mg, 100%). LCMS (Method B): $R_T$=3.84 min, $[M+H]^+$=519.

4-(4-Bromo-2-fluoro-phenylamino)-1H-indazole-5-carboxylic acid

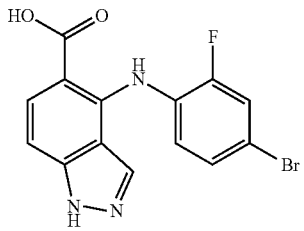 [SMILES: O=C(O)c1ccc2[nH]ncc2c1Nc1ccc(Br)cc1F]

Step 1: 4-(2-Fluoro-4-trimethylsilanyl-phenylamino)-indazole 1,5-dicarboxylic acid di-tert-butyl ester

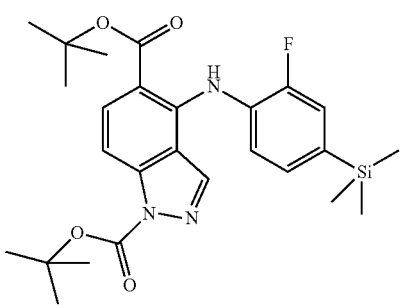 [SMILES: CC(C)(C)OC(=O)c1ccc2c(cnn2C(=O)OC(C)(C)C)c1Nc1ccc([Si](C)(C)C)cc1F]

A solution of 2-fluoro-4-trimethylsilanyl-phenylamine (1.2 g, 6.5 mmol) in toluene (20 mL) was added to a mixture of 4-bromo-indazole-1,5-dicarboxylic acid di-tert-butyl ester (2.0 g, 5.0 mmol), $Pd_2 dba_3$ (114 mg, 2.5 mol %), Xantphos (144 mg, 5 mol %) and potassium phosphate tribasic (1.49 g, 7 mmol) under nitrogen. The atmosphere was evacuated and back-filled with nitrogen and then the reaction mixture heated at 90° C. for 18 hours. The cooled reaction mixture was diluted with ethyl acetate, filtered through Celite®, and the filtrate concentrated in vacuo. The resultant residue was subjected to flash chromatography (Si—PPC, dry loading on HM-N, gradient 0 to 10% ethyl acetate in cyclohexane) to give the title compound as an orange gum (1.9 g, 76%). $^1$H NMR (CDCl$_3$, 400 MHz) 10.03 (1H, s), 8.05 (1H, d, J=9.03 Hz), 7.57 (1H, dd, J=9.00, 0.83 Hz), 7.28-7.18 (4H, m), 1.68 (9H, s), 1.63 (9H, s), 0.28 (9H, s).

Step 2: 4-(4-Bromo-2-fluoro-phenylamino)-indazole-1,5-dicarboxylic acid di-tert-butyl ester

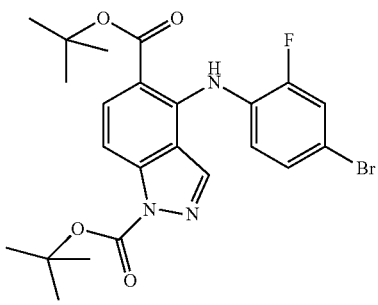 [SMILES: CC(C)(C)OC(=O)c1ccc2c(cnn2C(=O)OC(C)(C)C)c1Nc1ccc(Br)cc1F]

To a solution of 4-(2-fluoro-4-trimethylsilanyl-phenylamino)-indazole-1,5-dicarboxylic acid di-tert-butyl ester (850 mg, 1.7 mmol) in DCM (10 mL) at −15° C. was added N-bromosuccinimide (303 mg, 1.7 mmol) as a solution in DCM (3 mL) dropwise. The reaction mixture was stirred at −15° C. for 1.25 hours before DCM was added and the solution washed (saturated aqueous NaHCO$_3$ then water), dried (Na$_2$SO$_4$), filtered and concentrated in vacuo. The resultant residue was subjected to flash chromatography (Si—PPC, gradient 0 to 10% ethyl acetate in cyclohexane) to give the title compound as an orange gum (790 mg, 92%). LCMS (method B) $R_T$=5.41 min, $[M+CH_3CN+Na]^+$=569/571.

Step 3: 4-(4-Bromo-2-fluoro-phenylamino)-1H-indazole-5-carboxylic acid

To a solution of 4-(4-bromo-2-fluorophenylamino)-indazole-1,5-dicarboxylic acid di-tert-butyl ester (420 mg, 0.83 mmol) in DCM (5 ml) was added TFA (1.2 mL, 16.2 mmol). The reaction mixture was stirred at room temperature for 16 hours before being concentrated in vacuo. The resultant residue was dissolved in ethyl acetate (10 mL), washed with aqueous saturated sodium bicarbonate solution (10 mL) and the aqueous fraction extracted with ethyl acetate (2×10 mL). The combined organic extracts were washed with brine (20 mL), dried with MgSO$_4$ and concentrated in vacuo. The resultant residue was subjected to flash chromatography (Si—PPC, gradient 0-100% ethyl acetate in cyclohexane) to yield the title compound as an off-white solid (232 mg, 80%). LCMS (Method B): $R_T$=3.22 min, $[M+H]^+$=350/352.

4-(2-Fluoro-4-iodophenylamino)-1H-indazole-5-carboxylic acid

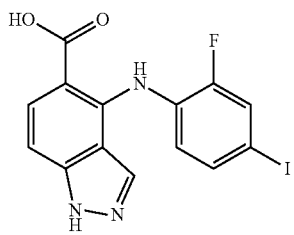 [SMILES: O=C(O)c1ccc2[nH]ncc2c1Nc1ccc(I)cc1F]

Step 1: 4-(2-Fluoro-4-iodophenylamino)-indazole-1,5-dicarboxylic acid di-tert-butyl ester

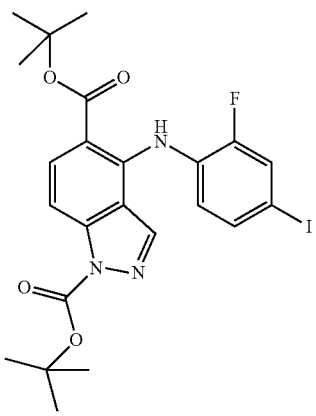 [SMILES: CC(C)(C)OC(=O)c1ccc2c(cnn2C(=O)OC(C)(C)C)c1Nc1ccc(I)cc1F]

To a solution of 4-(2-fluoro-4-trimethylsilanylphenylamino)-indazole-1,5-dicarboxylic acid di-tert-butyl ester (1.07 g, 2.14 mmol) in DCM (10 mL) at 0° C. was added iodine monochloride as a solution in DCM (4.2 mL, 1N, 4.2 mmol). The reaction mixture was stirred at 0° C. for 20 minutes then diluted with saturated aqueous sodium thiosulfate solution (10 mL) and extracted with DCM (2×10 mL). The combined organic extracts were washed with brine (20 mL), dried (MgSO$_4$) and concentrated in vacuo. The resultant residue was subjected to flash chromatography (Si—PPC, gradient 0-100% DCM in cyclohexane) to yield the title compound as a pale brown solid (611 mg, 52%). LCMS (Method B): R$_T$=5.48 min, [M+H]$^+$=554.

Step 2: 4-(2-Fluoro-4-iodophenylamino)-1H-indazole-5-carboxylic acid

To a solution of 4-(2-fluoro-4-iodophenylamino)-indazole-1,5-dicarboxylic acid di-tert-butyl ester (611 mg, 1.10 mmol) in DCM (5 ml) was added TFA (1.2 mL, 16.2 mmol). The reaction mixture was stirred at room temperature for 16 hours before being concentrated in vacuo. The resultant residue was dissolved in ethyl acetate (10 mL), washed with aqueous saturated sodium bicarbonate solution (10 mL) and the aqueous fraction extracted with ethyl acetate (2×10 mL). The combined organic fractions were washed with brine (20 mL), dried (MgSO$_4$) and concentrated in vacuo. The resultant residue was subjected to flash chromatography (Si—PPC, gradient 0-100% ethyl acetate in cyclohexane) to yield the title compound as an off-white solid (367 mg, 84%). LCMS (Method B): R$_T$=3.23 min, [M+H]$^+$=398.

4-(2-Fluoro-4-methylsulfanyl-phenylamino)-1H-indazole-5-carboxylic acid

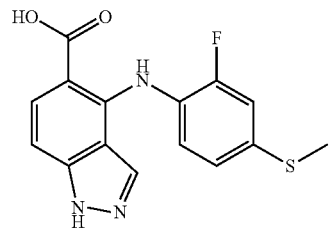 [SMILES: CSc1ccc(Nc2c(C(=O)O)ccc3[nH]ncc23)c(F)c1]

Step 1: 2,4-Difluoro-3-formyl-benzoic acid

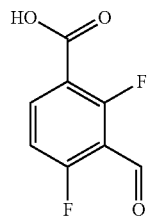

A solution of TMEDA (10.5 mL, 70 mmol) in THF (50 mL) was cooled to <−80° C. and treated with sec-butyllithium (50 mL, 70 mmol). A solution of 2,4-difluorobenzoic acid (5.0 g, 31.6 mmol) in THF was added dropwise maintaining the temperature below −80° C. The reaction mixture was allowed to warm to −75° C. and treated with DMF (15 mL), the mixture then allowed to warm to 0° C. before quenching the reaction with water. The aqueous layer was separated, acidified to pH ~2 (concentrated HCl) and extracted twice with diethyl ether. The combined organic extracts were dried (Na$_2$SO$_4$), filtered and concentrated in vacuo to give a yellow oil. The crude product was crystallized from cyclohexane/diethyl ether to give the title compound as a yellow solid (670 mg, 11%). $^1$H NMR (CDCl$_3$, 400 MHz) 10.40 (1 H, s), 8.31 (1 H, ddd, J=8.96, 8.02, 6.08 Hz), 7.12 (1 H, td, J=9.09, 1.42 Hz).

Step 2: 3-Dimethoxymethyl-2,4-difluoro-benzoic acid

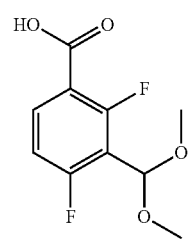

A mixture of 2,4-difluoro-3-formyl-benzoic acid (670 mg, 3.6 mmol) and ammonium chloride (1.15 g, 21.6 mmol) in methanol (20 mL) was heated at reflux for 18 hours. The reaction mixture was concentrated in vacuo and the residue partially dissolved in ethyl acetate and then filtered. The filtrate was concentrated in vacuo to give the title compound

Step 3: 4-Fluoro-2-(2-fluoro-4-methylsulfanyl-phenylamino)-3-formyl-benzoic acid

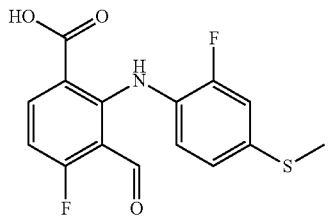 [SMILES: CSc1ccc(Nc2c(C(=O)O)ccc(F)c2C=O)c(F)c1]

To a cold (−78° C.) solution of 2-fluoro-4-methylsulfanyl-phenyl amine (1.55 g, 9.9 mmol) in THF (15 mL) was added LHMDS (9.9 mL, 1.0 M solution in hexanes 9.9 mmol) dropwise so as to maintain the temperature below −65° C. After stirring for 30 minutes a solution of 3-dimethoxymethyl-2,4-difluoro-benzoic acid (700 mg, 3.0 mmol) in THF (15 mL) was added dropwise, the resultant mixture stirred cold for 3 hours then allowed to warm to room temperature and stirred for 18 hours. The reaction was quenched by the addition of aqueous ammonium chloride and the products partitioned between ethyl acetate and water. The aqueous layer was separated and acidified to pH 1 (concentrated HCl) and then extracted twice with ethyl acetate. The combined organic extracts were dried (Na$_2$SO$_4$), filtered and concentrated in vacuo. The resultant residue was triturated with diethyl ether to give the title compound as a yellow solid (105 mg, 10% yield). $^1$H NMR (CDCl$_3$, 400 MHz) 10.26-10.23 (2 H, m), 8.04 (1 H, dd, J=8.76, 6.31 Hz), 7.03-6.96 (2H, m), 6.91 (1 H, d, J=1.96 Hz), 6.65 (1 H, dd, J=10.02, 8.77 Hz), 2.42 (3 H, s).

Step 4: 4-(2-Fluoro-4-methylsulfanyl-phenylamino)-1H-indazole-5-carboxylic acid To a suspension of 4-fluoro-2-(2-fluoro-4-methylsulfanyl-phenylamino)-3-formyl-benzoic acid (105 mg, 0.32 mmol) in DME (5 mL) was added hydrazine hydrate (5 mL) and the reaction mixture heated at 90° C. for 18 hours. The volatile solvent was removed in vacuo and the residue acidified with concentrated HCl whilst applying cooling. The resultant precipitate was collected by filtration and washed with water to give the title compound as a tan solid (85 mg, 82%). LCMS (Method B) R$_T$ 3.12 [M+H]$^+$ 318.

4-(2-Fluoro-4-iodo-phenylamino)-benzo[d]isothiazole-5-carboxylic acid

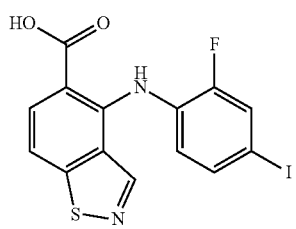 [SMILES: O=C(O)c1ccc2sncc2c1Nc1ccc(I)cc1F]

Step 1: 4-(2-Fluoro-4-trimethylsilanyl-phenylamino)benzo[d]isothiazole-5-carboxylic acid tert-butyl ester

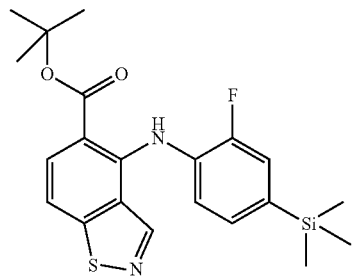 [SMILES: CC(C)(C)OC(=O)c1ccc2sncc2c1Nc1ccc([Si](C)(C)C)cc1F]

A solution of 2-fluoro-4-trimethylsilanyl-phenylamine (340 mg, 1.43 mmol), 4-bromo-benzo[d]isothiazole-5-carboxylic acid tert-butyl ester (449 mg, 1.43 mmol), Pd$_2$ dba$_3$ (65 mg, 0.07 mmol), Xantphos (83 mg, 0.14 mmol) and potassium phosphate tribasic (455 mg, 2.14 mmol) in toluene (5 mL) was degassed and then the reaction mixture heated at 90° C. for 18 hours. The cooled reaction mixture was diluted with ethyl acetate, filtered through Celite®, and the filtrate concentrated in vacuo. The resultant residue was subjected to flash chromatography (Si—PPC, gradient 2.5 to 5% diethyl ether in pentane) to give the title compound as a dark oil (465 mg, 78%). LCMS (Method B): R$_T$=5.76 min, [M+H]$^+$=417.

Step 2: 4-(2-Fluoro-4-iodo-phenylamino)-benzo[d]isothiazole 5-carboxylic acid tert-butyl ester

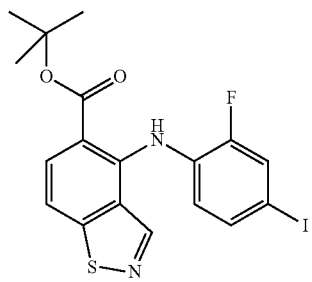 [SMILES: CC(C)(C)OC(=O)c1ccc2sncc2c1Nc1ccc(I)cc1F]

To a solution 4-(2-fluoro-4-trimethylsilanyl-phenylamino)-benzo[d]isothiazole-5-carboxylic acid tert-butyl ester (416 mg, 1.0 mmol) in DCM (10 mL) at −78° C. was added iodine monochloride as a solution in DCM (2.0 mL, 1M, 2.0 mmol). The reaction mixture was stirred at −78° C. for 1 hour then diluted with saturated aqueous sodium thiosulfate solution and extracted with DCM. The combined organic extracts were washed with brine, dried (Na$_2$SO$_4$) and concentrated in vacuo to yield the title compound as a yellow foam (459 mg, 98%). LCMS (Method B): R$_T$=5.32 min, [M+H]$^+$=471.

Step 3: 4-(2-Fluoro-4-iodo-phenylamino)-benzo[d]isothiazole 5-carboxylic acid To a solution of 4-(2-fluoro-4-iodo-phenylamino)-benzo[d]isothiazole-5-carboxylic acid tert-butyl ester (445 mg, 0.95 mmoL) in DCM (20 mL) was added water (0.1 mL), the mixture cooled to 0° C. and TFA (20 mL) added. The reaction mixture was stirred at room temperature for 2 hours then concentrated in vacuo and the residue azeotroped with tolu- 7-(2-Fluoro-4-iodo-phenylamino)-benzo[d]isothiazole-6-carboxylic acid

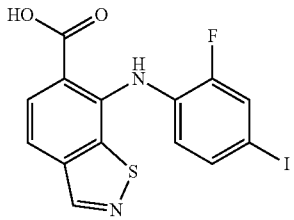 [SMILES: O=C(O)c1ccc2cnsc2c1Nc1ccc(I)cc1F]

Step 1: 7-(2-Fluoro-4-iodo-phenylamino)-benzo[d]isothiazole-6-carboxylic acid tert-butyl ester

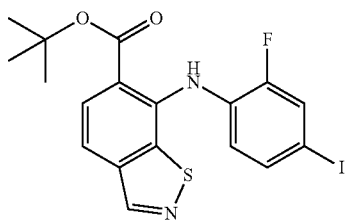 [SMILES: CC(C)(C)OC(=O)c1ccc2cnsc2c1Nc1ccc(I)cc1F]

To a solution of 7-fluoro-benzo[d]isothiazole-6-carboxylic acid tert-butyl ester (1.26 g, 5.0 mmol) and 2-fluoro-4-iodo-phenylamine (1.18 g, 5.0 mmol) in anhydrous THF (25 mL) at −78° C. was added a 1.0M solution of LHMDS in hexanes (10.0 mL, 10.0 mmol) under a nitrogen atmosphere. The reaction mixture was allowed to warm to room temperature and then stirred for 30 minutes before being quenched by the addition of a saturated aqueous solution of ammonium chloride and extracted with ethyl acetate. The organic layer was separated and washed with water followed by brine, dried (Na$_2$SO$_4$), filtered and evaporated in vacuo. The residue was subjected to flash chromatography (Si—PPC, gradient 0% to 10%, TBME in cyclohexane) to give the title compound as a yellow solid (717 mg, 30%). LCMS (method B): R$_T$=5.14 min, [M+H]$^+$=471.

Step 2: 7-(2-Fluoro-4-iodo-phenylamino)-benzo[d]isothiazole-6-carboxylic acid To a solution of 7-(2-fluoro-4-iodo-phenylamino)-benzo[d]isothiazole-6-carboxylic acid tert-butyl ester (710 mg, 1.51 mmol) in DCM (5 mL) were added water (0.15 mL) and TFA (5 mL). The reaction mixture was stirred at room temperature for 1 hour before being concentrated in vacuo. The resultant residue was azeotroped with toluene to give the title compound as a yellow solid (571 mg, 91%). LCMS (method B): R$_T$=3.95 min, [M+H]$^+$=415.

7-(4-Bromo-2-fluoro-phenylamino)-benzo[d]isothiazole-6-carboxylic acid

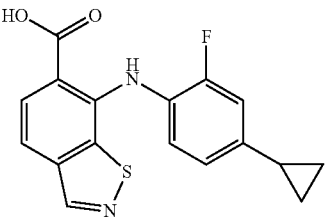 [SMILES: O=C(O)c1ccc2cnsc2c1Nc1ccc(C2CC2)cc1F]

To a solution of 4-bromo-2-fluoro-phenylamine (1.05 g, 5.55 mmol) in anhydrous THF (20 mL) at −78° C. was added a 1.0 M solution of LHMDS in hexanes (8.3 mL, 8.3 mmol) under a nitrogen atmosphere. The reaction mixture was stirred for 10 minutes and a suspension of 7-fluoro-benzo[d]isothiazole-6-carboxylic acid (547 mg, 2.78 mmol) in anhydrous THF (20 mL) was added dropwise. The resultant mixture was stirred at −78° C. for 30 min, then allowed to reach room temperature and stirred for 18 hours before being quenched by addition of a 1M aqueous HCl (ca. 50 mL) and extracted with ethyl acetate. The organic layer was separated and washed with water followed by brine, dried (Na$_2$SO$_4$), filtered and evaporated in vacuo. The resultant residue was subjected to flash chromatography (Si—PPC, gradient 0% to 10%, MeOH in DCM) to give the title compound as a brown solid (584 mg, 58%). LCMS (method B): R$_T$=3.76 min, [M−H]$^-$=365/367.

7-(4-Cyclopropyl-2-fluoro-phenylamino)-benzo[d]isothiazole-6-carboxylic acid

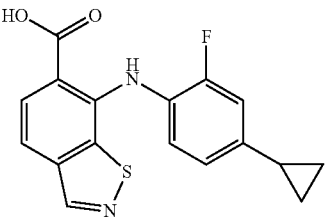 [SMILES: O=C(O)c1ccc2cnsc2c1Nc1ccc(C2CC2)cc1F]

To a solution of 4-cyclopropyl-2-fluoro-phenylamine (445 mg, 2.94 mmol) in anhydrous THF (10 mL) at −78° C. was added a 1.0 M solution of LHMDS in hexanes (4.4 mL, 4.4 mmol) under a nitrogen atmosphere. The reaction mixture was stirred for 10 minutes and a suspension of 7-fluoro-benzo[d]isothiazole-6-carboxylic acid (290 mg, 1.47 mmol) in anhydrous THF (10 mL) was added dropwise. The resultant mixture was stirred at −78° C. for 30 minutes, then allowed to reach room temperature and stirred for 18 hours before being quenched by addition of a 1M aqueous and extracted with ethyl acetate. The organic layer was separated and washed with water followed by brine, dried (Na$_2$SO$_4$), filtered and evaporated in vacuo. The resultant residue was triturated with diethyl ether to give the title compound as a brown solid (155 mg, 32%). LCMS (method B): R$_T$=3.79 min, [M+H]$^+$=329.

7-(2-Fluoro-4-methylsulfanyl-phenylamino)-benzo[d]isothiazole-6-carboxylic acid

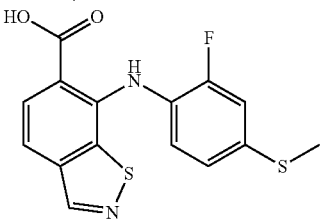

To a solution of 2-fluoro-4-methylsulfanyl-phenylamine (628 mg, 4.0 mmol) in anhydrous THF (15 mL) at −78° C. was added a 1.0M solution of LHMDS in hexanes (6.0 mL, 6.0 mmol) under a nitrogen atmosphere. The reaction mixture was stirred for 5 minutes and a suspension of 7-fluoro-benzo[d]isothiazole-6-carboxylic acid (394 mg, 2.0 mmol) in anhydrous THF (15 mL) was added dropwise. The resultant mixture was stirred at −78° C. for 30 minutes, then allowed to reach room temperature and stirred for 18 hours before being quenched by addition of a 1M aqueous HCl (ca. 50 mL) and extracted with ethyl acetate. The organic layer was separated and washed with water followed by brine, dried (Na$_2$SO$_4$), filtered and evaporated in vacuo. The resultant residue was subjected to flash chromatography (Si—PPC, gradient 0% to 10%, MeOH in DCM) to give the title compound as a brown solid (200 mg, 30%). LCMS (method B): R$_T$=3.67 min, [M+H]$^+$=335

Synthesis of 5-Amino-4-Anilino Indazole Intermediates

5-Amino-4-(2-fluoro-4-iodo-phenylamino)-indazole-1-carboxylic acid tert-butyl ester

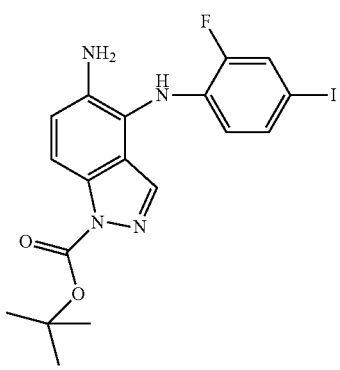 [SMILES: CC(C)(C)OC(=O)n1ncc2c(Nc3ccc(I)cc3F)c(N)ccc21]

Step 1: 2,6-Difluoro-3-nitro-benzaldehyde

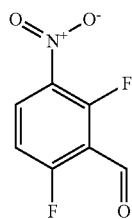

To stirring 69% nitric acid (6.48 ml, 93.59 mmol) cooled to 5° C. was added concentrated sulfuric acid (4.16 ml, 78.11 mmol) dropwise, keeping the internal temperature below 8° C. After complete addition stirring was continued for 15 minutes. This mixture was added to a solution of 2,6-difluorobenzaldehyde (10 g, 70.37 mmol) in concentrated sulfuric acid (50 ml) dropwise keeping the internal temperature below 10° C. After complete addition the mixture was stirred at 5° C. for 15 minutes then allowed to warm to room temperature over 90 minutes. The reaction mixture was poured onto ice-water (400 ml) and the resulting solid stirred for 1 hour. The solid was collected by filtration, washed with water and dried under vacuum to yield the title compound (9.27 g, 70%). $^1$H NMR (DMSO-d$_6$, 300 MHz): 10.21 (1 H, t, J=1.02 Hz), 8.52 (1 H, ddd, J=9.38, 8.60, 5.51 Hz), 7.51 (1 H, td, J=9.53, 1.76 Hz).

Step 2:
2-Dimethoxymethyl-1,3-difluoro-4-nitro-benzene

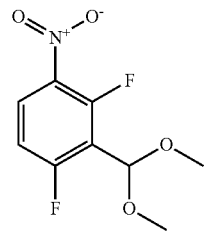 [SMILES: COC(OC)c1c(F)ccc([N+](=O)[O-])c1F]

A solution of 2,6-difluoro-3-nitro-benzaldehyde (9.0 g, 48.1 mmol), p-toluenesulfonic acid monohydrate (183 mg, 0.962 mmol), trimethylorthoformate (3.5 ml, 32.4 mmol) and methanol (200 ml) was heated at reflux for 4 hours. The reaction mixture was allowed to cool to room temperature and then concentrated in vacuo. The resultant residue was dissolved in DCM (250 mL) and washed with a mixture of water (200 mL) and saturated NaHCO$_3$ solution (50 mL). The organic layer was dried (Na$_2$SO$_4$) and concentrated in vacuo to yield the title compound (10.83 g, 97%). $^1$H NMR (DMSO-d$_6$, 300 MHz): 8.28 (1 H, ddd, J=9.34, 8.48, 5.51 Hz), 7.39 (1 H, td, J=9.34, 1.81 Hz), 5.66 (1 H, s), 3.40 (6 H, s).

Step 3: (2-Dimethoxymethyl-3-fluoro-6-nitro-phenyl)-(2-fluoro-4-iodo-phenyl)-amine

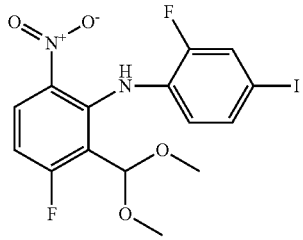 [SMILES: COC(OC)c1c(F)ccc([N+](=O)[O-])c1Nc1ccc(I)cc1F]

To a solution of 2-fluoro-4-iodo-aniline (2.24 g, 9.43 mmol) in anhydrous THF (30 ml) under an atmosphere of nitrogen was added 1M LHMDS in hexanes (18 ml, 1M, 18.0 mmol) keeping the internal temperature below −65° C. After complete addition the reaction mixture was stirred for 30 minutes at −70° C. A solution of 2-dimethoxymethyl-1,3-difluoro-4-nitro-benzene (2.0 g, 8.58 mmol) in anhydrous THF (20 ml) was added to the reaction mixture keeping the internal temperature below −68° C. After complete addition

Step 4: 6-Fluoro-2-(2-fluoro-4-iodo-phenylamino)-3-nitro-benzaldehyde

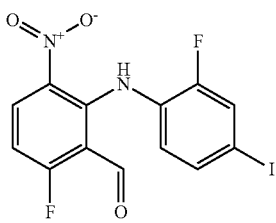 [SMILES: O=Cc1c(F)ccc([N+](=O)[O-])c1Nc1ccc(I)cc1F]

the reaction mixture was stirred for 30 minutes at −70° C. then allowed to warm to room temperature and stirred for 22 hours. The reaction was quenched with saturated aqueous NH$_4$Cl solution and extracted with ethyl acetate (200 ml). The organic layer was washed with brine, dried (Na$_2$SO$_4$), concentrated in vacuo to a minimum volume and triturated with cyclohexane to yield the title compound (2.18 g, 56%). LCMS (Method B): R$_T$=4.26 min, [M−H]$^-$=449.

To a stirred solution of (2-dimethoxymethyl-3-fluoro-6-nitro-phenyl)-(2-fluoro-4-iodo-phenyl)-amine (1.0 g, 2.22 mmol) in THF (10 ml) was added a solution of 4M HCl at room temperature. After 2 hours the THF was removed in vacuo and the residue diluted with water (20 ml) providing a precipitate. The solid precipitate was collected by filtration, washed with water and dried under vacuum to yield the title compound (864 mg, 96%). LCMS (Method B): R$_T$=4.06 min, [M−H]$^-$=403.

Step 5: (2-Fluoro-4-iodo-phenyl)-(5-nitro-1H-indazol-4-yl)-amine

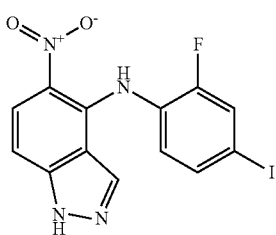 [SMILES: O=[N+]([O-])c1ccc2[nH]ncc2c1Nc1ccc(I)cc1F]

To a stirred solution of 6-fluoro-2-(2-fluoro-4-iodo-phenylamino)-3-nitro-benzaldehyde (864 mg, 2.14 mmol) in DME (15 ml) was slowly added hydrazine hydrate (10 mL) at room temperature and the reaction mixture stirred for 18 hours. The organic solvent was removed in vacuo and the mixture diluted with water (50 mL). The resulting solid was collected by filtration, washed with water and dried under vacuum to yield the title compound (839 mg, 98%). LCMS (Method B): R$_T$=3.61 min, [M+H]$^+$=399.

Step 6: 4-(2-Fluoro-4-iodo-phenylamino)-5-nitro-indazole-1-carboxylic acid tert-butyl ester

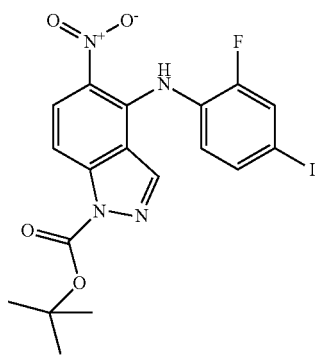 [SMILES: CC(C)(C)OC(=O)n1ncc2c(Nc3ccc(I)cc3F)c([N+](=O)[O-])ccc21]

To a suspension of (2-fluoro-4-iodo-phenyl)-(5-nitro-1H-indazol-4-yl)-amine (839 mg, 2.11 mmol) and triethylamine (0.323 mL, 2.32 mmol) in dichloromethane was added di-tert-butyl di-carbonate (552 mg, 2.53 mmoL) and DMF (1 mL), the resultant solution stirred at room temperature for 2 hours. Further di-tert-butyl di-carbonate (275 mg, 1.26 mmoL) and DMAP (25 mg, 10 mol %) were added and the mixture stirred for 10 minutes. The reaction mixture was diluted with ethyl acetate (150 mL) and washed with saturated aqueous NaHCO$_3$ (100 mL) then water (100 mL) and then brine (100 mL) before drying (Na$_2$SO$_4$) and concentrating in vacuo. The resultant residue was subjected to flash chromatography (Si—PPC gradient 0-35% ethyl acetate in cyclohexane) to give the title compound (739 mg, 70%). LCMS (Method B): R$_T$=4.57 min, [M-Boc+H]$^+$=399.

Step 7: 5-Amino-4-(2-fluoro-4-iodo-phenylamino)-indazole-1-carboxylic acid tert-butyl ester A suspension of sodium dithionite (978 mg, 4.21 mmol) and 4-(2-fluoro-4-iodo-phenylamino)-5-nitro-indazole-1-carboxylic acid tert-butyl ester (700 mg, 1.4 mmol) in water (35 mL) was treated with a 1:1 mixture of THF:dioxane (34 mL), the homogeneous reaction mixture stirred at room temperature for 4 hours. Further sodium dithionite (978 mg, 4.21 mmol) was added and stirring continued for 20 hours. The reaction mixture was basified by the addition of saturated aqueous sodium hydrogen carbonate and then extracted with ethyl acetate (150 mL). The organic extract was washed with water, dried (Na$_2$SO$_4$), filtered and concentrated in vacuo to give the title compound as a yellow solid (758 mg, quant.). LCMS (Method B) R$_T$=4.09 min, [M+H]$^+$=469.

5-Amino-4-(2-fluoro-4-iodo-phenylamino)-6-methoxy-indazole-1-carboxylic acid tert-butyl ester

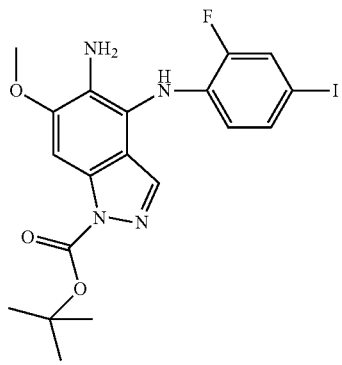

Step 1: 2,6-Difluoro-4-methoxy-3-nitro-benzaldehyde

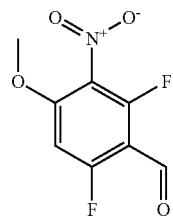

To a solution of cold (−5° C.) nitric acid (2.7 mL) was added concentrated sulfuric acid (1.75 mL, 32 mmoL) dropwise keeping the temperature below 5° C. The solution was added to a cooled solution of 2,6-difluoro-4-methoxy benzaldehyde (5.0 g, 29 mmoL) in sulfuric acid (20 mL) over 15 minutes keeping the temperature below 5° C. After stirring at 0° C. for 2 hours the orange solution was poured on to ice, the white precipitate which formed was collected by filtration to give the title compound as a white solid (6.33 g, 100%). $^1$H NMR (CDCl$_3$) 10.20 (1 H, t, J=1.17 Hz), 6.69 (1 H, dd, J=11.68, 1.93 Hz), 4.03 (3 H, s).

Step 2: 2-Dimethoxymethyl-1,3-difluoro-5-methoxy-4-nitro-benzene

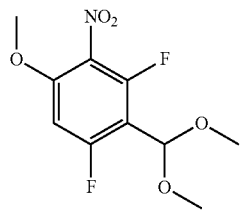 [SMILES: COc1cc(F)c(C(OC)OC)c(F)c1[N+](=O)[O-]]

A mixture of 2,6-difluoro-4-methoxy-3-nitro-benzaldehyde (6.3 g, 29 mmol) in methanol (30 mL) with p-toluenesulfonic acid (110 mg, 0.58 mmol) was heated at reflux for 18 hours. The reaction mixture was concentrated in vacuo and the residue partitioned between saturated aqueous sodium hydrogen carbonate and ethyl acetate. The aqueous layer extracted with ethyl acetate and the combined organic extracts dried (Na$_2$SO$_4$), filtered and concentrated in vacuo to give the title compound as a pale yellow solid (6.52 g, 85%). $^1$H NMR (CDCl$_3$) 6.59 (1 H, dd, J=11.48, 2.08 Hz), 5.52 (1 H, s), 3.93 (3 H, s), 3.45 (6 H, s).

Step 3: (2-Dimethoxymethyl-3-fluoro-5-methoxy-6-nitro-phenyl)-(2-fluoro-4-iodo-phenyl)-amine

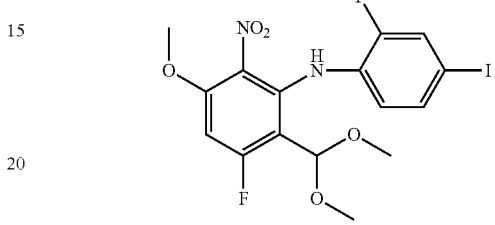

To a cold (−78° C.) solution of 2-fluoro-4-iodo-phenyl amine (2.97 g, 12.5 mmol) in THF (20 mL) was added LHMDS (24 mL, 1.0 M solution in hexanes 24 mmol) dropwise maintaining the temperature below −65° C. After stirring for 30 minutes a solution of 2-dimethoxymethyl-1,3-difluoro-5-methoxy-4-nitro-benzene (3.0 g, 11.4 mmol) in THF (20 mL) was added dropwise, the resultant mixture stirred cold (−78° C.) for 1 hour then allowed to warm to room temperature and stirred for 18 hours. The reaction was quenched by the addition of aqueous ammonium chloride and extracted twice with diethyl ether. The combined organic extracts were washed with water, dried (Na$_2$SO$_4$), filtered and concentrated in vacuo to give an orange solid. The crude orange solid was triturated in diethyl ether to give the title compound as a yellow solid (4.2 g, 77%). $^1$H NMR (CDCl$_3$) 7.36 (1 H, dd, J=10.09, 1.93 Hz), 7.28-7.17 (2 H, m), 6.59 (1 H, t, J=8.62 Hz), 6.44 (1H, d, J=11.47 Hz), 5.49 (1 H, s), 3.88 (3 H, s), 3.39 (6 H, s).

Step 4: 6-Fluoro-2-(2-fluoro-4-iodo-phenylamino)-4-methoxy-3-nitro-benzaldehyde

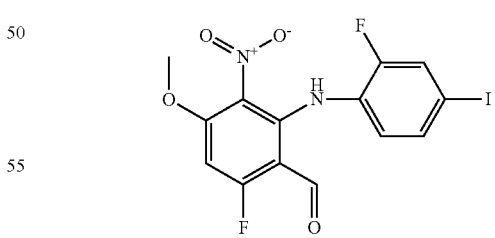

A mixture of (2-dimethoxymethyl-3-fluoro-5-methoxy-6-nitro-phenyl)-(2-fluoro-4-iodo-phenyl)-amine (4.2 g, 8.7 mmol) in diethyl ether (70 mL) and 4M HCl (50 mL) was stirred at room temperature for 8 hours. The mixture was extracted with ethyl acetate, the organic extract washed with water, dried (Na$_2$SO$_4$), filtered and concentrated in vacuo to give the title compound as a yellow solid (3.1 g, 82%). LCMS (Method B) R$_T$=4.00 no molecular ion.

Step 5: (2-Fluoro-4-iodo-phenyl)-(6-methoxy-5-nitro-1H-indazol-4-yl)-amine

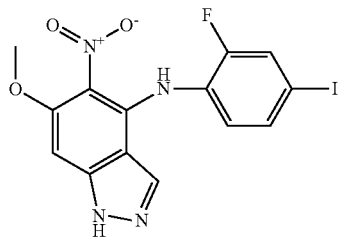 [SMILES: COc1cc2[nH]ncc2c(Nc2ccc(I)cc2F)c1[N+](=O)[O-]]

A biphasic mixture of 6-fluoro-2-(2-fluoro-4-iodo-phenylamino)-4-methoxy-3-nitro-benzaldehyde (1.5 g, 3.46 mmol) in hydrazine hydrate (10 mL) and DME (10 mL) was stirred at room temperature for 4 hours, then heated at 50° C. for 3 hours. The reaction mixture was concentrated in vacuo, the residue treated with water and the resultant solid precipitate collected by filtration to give a red/orange solid. The solid was recrystallised from IMS to give the title compound as a yellow solid (956 mg, 64%). LCMS (Method B) $R_T$=3.62 min, $[M+H]^+$=429 $[M-H]^-$=427.

Step 6: 4-(2-Fluoro-4-iodo-phenylamino)-6-methoxy-5-nitro-indazole-1-carboxylic acid tert-butyl ester

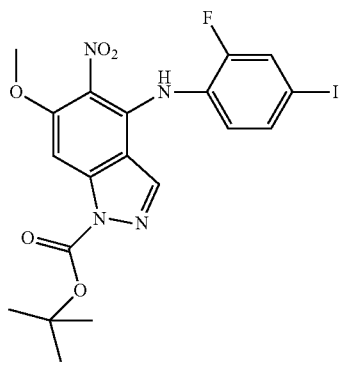 [SMILES: COc1cc2c(cnn2C(=O)OC(C)(C)C)c(Nc2ccc(I)cc2F)c1[N+](=O)[O-]]

A suspension of (2-fluoro-4-iodo-phenyl)-(6-methoxy-5-nitro-1H-indazol-4-yl)-amine (900 mg, 2.1 mmol) in DCM (10 mL) was treated with di-tert-butyl-dicarbonate (550 mg, 2.5 mmol) and triethylamine (0.321 mL, 4.6 mmol) and DMF (2 mL). The reaction mixture was stirred for 5 hours at room temperature before being concentrated in vacuo and the residue partitioned between ethyl acetate and saturated aqueous sodium hydrogen carbonate. The organic layer was separated, washed with water, dried ($Na_2SO_4$), filtered and concentrated in vacuo. The resultant residue was subjected to flash chromatography (Si—PPC gradient 0 to 15% ethyl acetate in cyclohexane) to give the title compound as a yellow solid (534 mg, 48%). $^1$H NMR ($CDCl_3$) 7.84 (1H, s), 7.52 (1 H, dd, J=9.63, 1.90 Hz), 7.47 (1 H, s), 7.43-7.38 (1 H, m), 7.29 (1 H, d, J=0.78 Hz), 6.91 (1 H, t, J=8.40 Hz), 4.02 (3 H, s), 1.70 (9 H, s).

Step 7: 5-Amino-4-(2-fluoro-4-iodo-phenylamino)-6-methoxy-indazole-1-carboxylic acid tert-butyl ester A suspension of sodium dithionite (524 mg, 3.48 mmol) and 4-(2-fluoro-4-iodo-phenylamino)-6-methoxy-5-nitro-indazole-1-carboxylic acid tert-butyl ester (434 mg, 0.87 mmol) in water (10 mL) was treated with a 1:1 mixture of THF:dioxane (10 mL). The homogeneous reaction mixture stirred at room temperature for 18 hours. The reaction mixture was basified by the addition of saturated aqueous sodium hydrogen carbonate and then extracted twice with ethyl acetate. The combined organic extracts were washed with water, dried ($Na_2SO_4$), filtered and concentrated in vacuo to give the title compound as a yellow solid (300 mg, 73%). LCMS (Method B) $R_T$ 4.16 min, $[M+H]^+$=499 $[M-H]^-$=497.

Example 5

4-(2-Fluoro-4-iodo-phenylamino)-1H-indazole-5-carboxylic acid (2-hydroxy-ethoxy)-amide

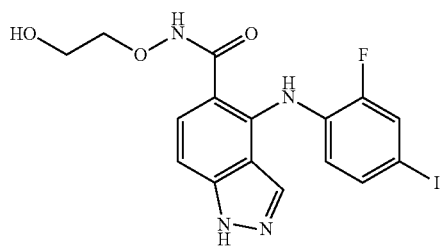 [SMILES: O=C(NOCCO)c1ccc2[nH]ncc2c1Nc1ccc(I)cc1F]

Method A, Step 1: 4-(2-Fluoro-4-iodophenylamino)-1-(toluene-4-sulfonyl)-1H-indazole-5-carboxylic acid (2-vinyloxy-ethoxy)-amide

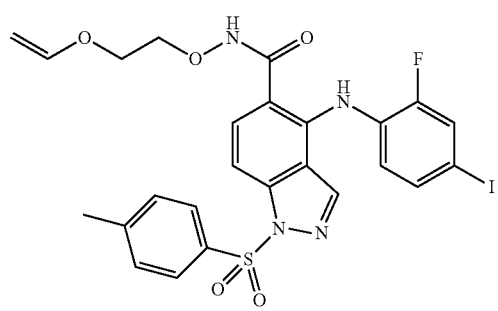 [SMILES: C=COCCONC(=O)c1ccc2c(cnn2S(=O)(=O)c2ccc(C)cc2)c1Nc1ccc(I)cc1F]

To a solution of 4-(2-fluoro-4-iodo-phenylamino)-1-(toluene-4-sulfonyl)-1H-indazole-5-carboxylic acid (0.58 g, 1.05 mmol) in DMF (10 mL) was added EDCI (0.22 g, 1.1 mmol) followed by HOBt (0.16 g, 1.1 mmol) and the reaction mixture stirred at room temperature for 10 minutes. O-(2-vinyloxy-ethyl)-hydroxylamine (0.12 g, 1.1 mmol) and DIPEA (0.2 mL, 1.1 mmol) were added and the reaction stirred for 16 hours before being concentrated in vacuo. The resultant residue was dissolved in ethyl acetate (10 mL), washed with an aqueous saturated sodium bicarbonate solution (10 mL) before the aqueous fraction was extracted twice with ethyl acetate (2×10 mL). The combined organic extracts were washed with brine (20 mL), dried ($MgSO_4$) and concentrated in vacuo. The resultant residue was subjected to flash chromatography (Si—PPC, gradient 0-100% ethyl acetate in cyclohexane) to yield the title compound as a pale brown solid (439 mg, 66%). LCMS (Method B): $R_T$=4.40 min, [M+H]$^+$=637.

Method A, Step 2: 4-(2-Fluoro-4-iodo-phenylamino)-1H-indazole-5-carboxylic acid (2-hydroxyethoxy)-amide To a solution of 4-(2-fluoro-4-iodophenylamino)-1-(toluene-4-sulfonyl)-1H-indazole-5-carboxylic acid (2-vinyloxyethoxy)-amide (200 mg, 0.31 mmol) in methanol (3 mL) was added hydrochloric acid (1 mL, 1 N) and the reaction mixture stirred at room temperature for 1 hour. The reaction mixture was concentrated in vacuo and the resultant residue dissolved in TFA (2 mL). The reaction mixture was heated at 65° C. for 3 hours then at 50° C. for 16 hours before being concentrated in vacuo. The resultant residue was dissolved in ethyl acetate (10 mL), washed with aqueous saturated sodium bicarbonate solution (10 mL) and the aqueous fraction extracted twice with ethyl acetate (2×10 mL). The combined organic fractions were washed with brine (20 mL), dried (MgSO$_4$) and concentrated in vacuo. The resultant residue was subjected to reverse phase preparative HPLC (gradient 10-95% acetonitrile/water+0.1% formic acid, Phenominex gemini PhC6, 5 micron, 250×20 mm). The resultant product was dissolved in ethyl acetate (5 mL) and washed with aqueous saturated sodium bicarbonate solution (10 mL). The aqueous fraction was extracted twice with ethyl acetate (2×10 mL) and the combined organics washed with brine (20 mL), dried with MgSO$_4$ and concentrated in vacuo to yield the title compound as a white solid (14 mg, 10%). LCMS (Method A): $R_T$=8.31 min, [M+H]$^+$=457. $^1$H NMR (DMSO-d$_6$, 400 MHz): 13.19 (1 H, s), 11.60 (1H, s), 9.93 (1H, s), 7.66 (1 H, dd, J=10.31, 1.93 Hz), 7.46 (1H, d, J=8.70 Hz), 7.42 (1H, d, J=8.56 Hz), 7.23 (1H, s), 7.01 (1H, d, J=8.77 Hz), 6.91 (1H, t, J=8.64 Hz), 4.68 (1H, s), 3.85 (2H, t, J=4.92 Hz), 3.60-3.52 (2H, m).

Method B, Step 1: 4-(2-Fluoro-4-iodophenylamino)-1H-indazole-5-carboxylic acid (2-vinyloxyethoxy)-amide

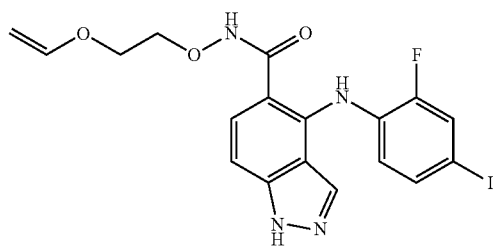 [SMILES: C=COCCONC(=O)c1ccc2[nH]ncc2c1Nc1ccc(I)cc1F]

To a solution of 4-(2-fluoro-4-iodophenylamino)-1H-indazole-5-carboxylic acid (2.14 g, 5.39 mmol) and O-(2-vinyloxy-ethyl)-hydroxylamine (668 mg, 6.50 mmol) in DMF (50 mL) was added EDCI (1.14 g, 5.93 mmol), HOBt (0.80 g, 5.93 mmol) and DIPEA (1 mL, 5.93 mmol). The reaction mixture was stirred at room temperature for 2 hours before being concentrated in vacuo. The resultant residue was dissolved in ethyl acetate (30 mL), washed with aqueous saturated sodium hydrogen carbonate solution (300 mL) and the aqueous fraction extracted with ethyl acetate (2×20 mL). The combined organic extracts were washed with brine (30 mL), dried (MgSO$_4$) and concentrated in vacuo. The resultant residue was subjected to flash chromatography (SiO$_2$, gradient 0-100% ethyl acetate in cyclohexane) to yield the title compound as a pale yellow solid (1.85 g, 71%). LCMS (Method B): $R_T$=3.52 min, [M−H]$^-$=481.

Method B, Step 2: 4-(2-Fluoro-4-iodophenylamino)-1H-indazole-5-carboxylic acid (2-hydroxyethoxy)-amide To a solution of 4-(2-fluoro-4-iodophenylamino)-1H-indazole-5-carboxylic acid (2-vinyloxyethoxy)-amide (1.85 g, 3.84 mmol) in methanol (40 mL) was added hydrochloric acid (3 mL, 1N, 3 mmol). The reaction mixture was stirred at room temperature for 1 hour, during which an off-white solid precipitated. The reaction mixture was concentrated in vacuo and the residue triturated with hot methanol/water (10 mL, 1:1). The product was collected by filtration and dried in vacuo to yield the title compound as an off white solid (1.26 g, 72%). LCMS (Method A): $R_T$=8.28 min, [M+H]$^+$=457. $^1$H NMR (DMSO-d$_6$): 13.20 (1 H, s), 11.61 (1 H, s), 9.93 (1 H, s), 7.66 (1 H, dd, J=10.32, 1.95 Hz), 7.46 (1 H, d, J=8.81 Hz), 7.42 (1 H, dd, J=8.49, 1.84 Hz), 7.24 (1 H, s), 7.01 (1 H, d, J=8.78 Hz), 6.91 (1 H, t, J=8.65 Hz), 4.68 (1 H, s), 3.85 (2 H, dd, J=5.41, 4.48 Hz), 3.56 (2 H, t, J=4.85 Hz).

Example 6

4-(2-Fluoro-4-iodophenylamino)-1H-pyrazolo[3,4-b]pyridine 5-carboxylic acid (2-hydroxyethoxy)-amide

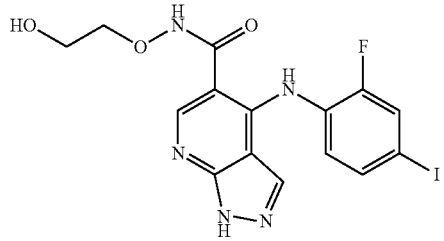 [SMILES: O=C(NOCCO)c1cnc2[nH]ncc2c1Nc1ccc(I)cc1F]

Step 1: 4-(2-Fluoro-4-iodophenylamino)-1-(4-methoxybenzyl)-1H-pyrazolo[3,4-b]pyridine-5-carboxylic acid (2-vinyloxyethoxy)-amide

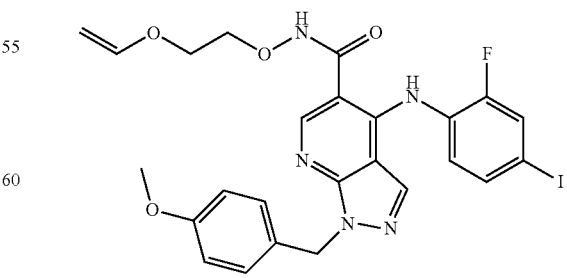

4-(2-Fluoro-4-iodophenylamino)-1-(4-methoxybenzyl)-1H-pyrazolo[3,4-b]pyridine-5-carboxylic acid (360 mg, 0.71 mmol), O-(2-vinyloxyethyl)-hydroxylamine (79 mg, 0.77 mmol), HOBt (103 mg, 0.77 mmol), EDCI (147 mg, 0.77 mmol) and DIPEA (130 µL, 0.77 mmol) were dissolved in DMF (10 mL). The reaction mixture was stirred at room temperature for 16 hours then concentrated in vacuo. The resultant residue was dissolved in ethyl acetate (10 mL), washed with aqueous saturated sodium bicarbonate solution (10 mL) and the aqueous fraction extracted twice with ethyl acetate (2×10 mL). The combined organic fractions were washed with brine (20 mL), dried (MgSO$_4$) and concentrated in vacuo. The resultant residue was subjected to flash chromatography (Si—SPE, gradient 0-100% ethyl acetate in cyclohexane) to yield the title compound as a yellow solid (346 mg, 81%). LCMS (Method B): R$_T$=4.08 min, [M+H]$^+$=604.

Step 2: 4-(2-Fluoro-4-iodophenylamino)-1H-pyrazolo[3,4-b]pyridine 5-carboxylic acid (2-hydroxyethoxy)-amide 4-(2-Fluoro-4-iodophenylamino)-1-(4-methoxybenzyl)-1H-pyrazolo[3,4-b]pyridine-5-carboxylic acid (2-vinyloxyethoxy)-amide (346 mg, 0.57 mmol) was dissolved in TFA (5 mL) and the reaction mixture heated at 65° C. for 3 hours. The reaction mixture was concentrated in vacuo and the residue was dissolved in ethyl acetate (10 mL), washed with aqueous saturated sodium bicarbonate solution (10 mL) and the aqueous fraction extracted twice with ethyl acetate (2×10 mL). The combined organic extracts were washed with brine (20 mL), dried (MgSO$_4$) and concentrated in vacuo. The resultant residue was subjected to flash chromatography (Si—SPE, gradient 0-10% methanol in DCM) to yield the title compound as a yellow solid (75 mg, 30%). LCMS (Method A): R$_T$=6.67 min, [M+H]$^+$=458. $^1$H NMR (DMSO-d$_6$, 400 MHz) 13.51 (1H, s), 11.75 (1H, s), 10.38 (1H, s), 8.45 (1H, s), 7.80 (1H, dd, J=9.67, 1.86 Hz), 7.64-7.60 (1H, m), 7.30-7.21 (1H, m), 6.74 (1H, s), 4.71 (1H, s), 3.90 (2H, t, J=4.95 Hz), 3.61-3.56 (3H, m).

Example 7

4-(2-Fluoro-4-iodophenylamino)-1H-pyrazolo[3,4-b]pyridine 5-carboxylic acid ((S)-2-hydroxypropoxy)-amide

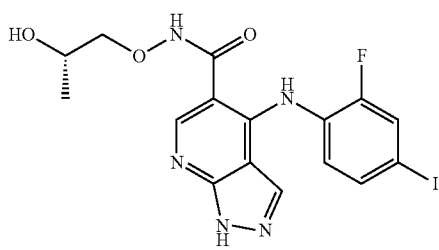 [SMILES: C[C@H](O)CONC(=O)c1cnc2[nH]ncc2c1Nc1ccc(I)cc1F]

Step 1: 4-(2-Fluoro-4-iodophenylamino)-1-(4-methoxybenzyl)-1H-pyrazolo[3,4-b]pyridine-5-carboxylic acid ((S)-2-hydroxypropoxy)-amide

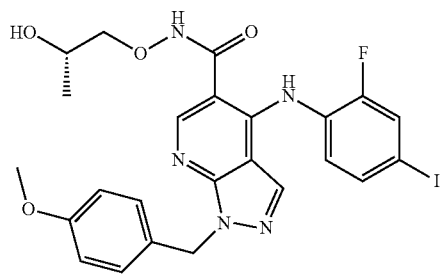 [SMILES: COc1ccc(Cn2ncc3c(Nc4ccc(I)cc4F)c(C(=O)NOC[C@H](C)O)cnc32)cc1]

To a solution of 4-(2-fluoro-4-iodophenylamino)-1-(4-methoxybenzyl)-1H-pyrazolo[3,4-b]pyridine-5-carboxylic acid (728 mg, 1.4 mmol), HOBt (228 mg, 1.7 mmol) and EDCI (323 mg, 1.7 mmol) in DMF (15 mL) was added a solution of (S)-1-aminooxypropan-2-ol hydrochloride (200 mg, 1.5 mmol), and DIPEA (596 µL, 3.5 mmol) in DMF (5 mL). The reaction mixture was stirred at room temperature for 3 hours then diluted with water (30 mL) and the aqueous layer extracted with dichloromethane (3×20 mL). The combined organic extracts were filtered through a hydrophobic frit and concentrated in vacuo. The resultant residue was subjected to flash chromatography (Si—SPE, gradient 0-100% ethyl acetate in cyclohexane) to yield the title compound as a cream solid (500 mg, 60%). LCMS (Method B): R$_T$=3.23 min, [M+H]$^+$=592.

Step 2: 4-(2-Fluoro-4-iodophenylamino)-1H-pyrazolo[3,4-b]pyridine-5-carboxylic acid ((S)-2-hydroxypropoxy)-amide 4-(2-Fluoro-4-iodophenylamino)-1-(4-methoxybenzyl)-1H-pyrazolo[3,4-b]pyridine-5-carboxylic acid ((S)-2-hydroxypropoxy)-amide (500 mg, 0.85 mmol) was dissolved in TFA (5 mL) and the resulting mixture heated at 65° C. for 3 hours before being concentrated in vacuo. The resultant residue was dissolved in dichloromethane (10 mL) and methanol (2 mL) then stirred vigorously with aqueous saturated sodium bicarbonate solution (20 mL) for 2 hours. The aqueous layer was extracted with dichloromethane (2×10 mL) and the combined organic fractions filtered through a hydrophobic frit then concentrated in vacuo. The resultant residue was purified by reverse-phase HPLC (gradient 10-95% methanol/water+ 0.1% formic acid, Phenominex gemini PhC6, 5 micron, 250× 20 mm) to yield the title compound as a white solid (106 mg, 27%). LCMS (Method A): R$_T$=7.19 min, [M+H]$^+$=472. $^1$H NMR (DMSO-d$_6$, 400 MHz) 13.51 (1H, s), 10.37 (1H, s), 8.45 (1H, s), 7.80 (1H, dd, J=9.68, 1.89 Hz), 7.63-7.60 (1H, m), 7.25 (1H, t, J=8.42 Hz), 6.74 (1H, s), 3.88-3.81 (1H, m), 3.73-3.69 (2H, m), 1.05 (3H, d, J=6.34 Hz).

Example 8

4-(2-Fluoro-4-iodophenylamino)-1H-pyrazolo[3,4-b]pyridine-5-carboxylic acid (2-hydroxy-1,1-dimethylethoxy)-amide

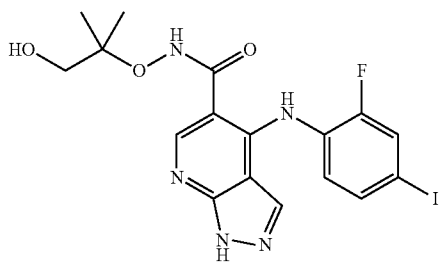 [SMILES: CC(C)(CO)ONC(=O)c1cnc2[nH]ncc2c1Nc1ccc(I)cc1F]

Step 1: 4-(2-Fluoro-4-iodophenylamino)-1-(4-methoxybenzyl)-1H-pyrazolo[3,4-b]pyridine-5-carboxylic acid (2-hydroxy-1,1-dimethylethoxy)-amide

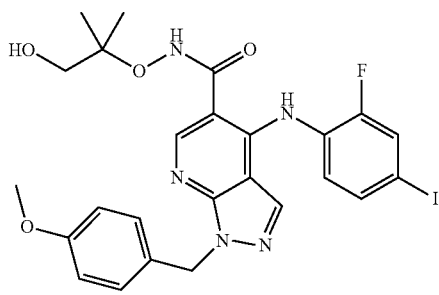 [SMILES: COc1ccc(Cn2ncc3c(Nc4ccc(I)cc4F)c(C(=O)NOC(C)(C)CO)cnc32)cc1]

To a solution of 4-(2-fluoro-4-iodophenylamino)-1-(4-methoxybenzyl)-1H-pyrazolo[3,4-b]pyridine-5-carboxylic acid (737 mg, 1.4 mmol), HOBt (231 mg, 1.7 mmol), and EDCI (327 mg, 1.7 mmol) in DMF (15 mL) was added a solution of 2-aminooxy-2-methyl-propan-1-ol hydrochloride (280 mg, 2.0 mmol), and DIPEA (603 µL, 3.6 mmol) in DMF (5 mL). The reaction mixture was stirred at room temperature for 3 days then diluted with water (30 mL) and the aqueous layer extracted with dichloromethane (3×20 mL). The combined organic fractions were filtered through a hydrophobic frit and concentrated in vacuo. The resultant residue was subjected to flash chromatography (Si—SPE, gradient 0-100% ethyl acetate in cyclohexane) to yield the title compound as a yellow solid (420 mg, 49%). LCMS (Method B): $R_T$=3.47 min, $[M+H]^+$=606.

Step 2: 4-(2-Fluoro-4-iodophenylamino)-1H-pyrazolo[3,4-b]pyridine-5-carboxylic acid (2-hydroxy-1,1-dimethylethoxy)amide 4-(2-Fluoro-4-iodophenylamino)-1-(4-methoxybenzyl)-1H-pyrazolo[3,4-b]pyridine-5-carboxylic acid (2-hydroxy-1,1-dimethylethoxy)-amide (420 mg, 0.69 mmol) was dissolved in TFA (5 mL) and the reaction mixture heated at 65° C. for 3 hours. The reaction mixture was concentrated in vacuo and the resultant residue was dissolved in dichloromethane (10 mL) and methanol (2 mL) before being washed with aqueous saturated sodium bicarbonate solution (3×10 mL). The aqueous layer was extracted with dichloromethane (2×10 mL) and the combined organic extracts filtered through a hydrophobic frit then concentrated in vacuo. The resultant residue was purified by reverse-phase HPLC (gradient 10-95% methanol/water+0.1% formic acid, Phenominex gemini PhC6, 5 micron, 250×20 mm) to yield the title compound as a white solid (21 mg, 11%). LCMS (Method A): $R_T$=7.71 min, $[M+H]^+$=486. $^1$H NMR (DMSO-$d_6$, 400 MHz) 13.53 (1H, s), 11.20 (1H, s), 10.15 (1H, s), 8.49 (1H, s), 7.80 (1H, d, J=9.68 Hz), 7.63 (1H, d, J=8.38 Hz), 7.25 (1H, t, J=8.38 Hz), 6.70 (1H, s), 4.65 (1H, s), 1.17 (6H, s).

Example 9

4-(2-Fluoro-4-iodophenylamino)-1H-indazole-5-carboxylic acid ((R)-2,3-dihydroxy-propoxy)-amide

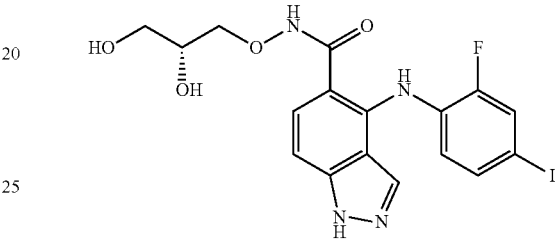

Step 1: 4-(2-Fluoro-4-iodophenylamino)-1H-indazole-5-carboxylic acid ((R)-2,2-dimethyl-[1,3]-dioxolan-4-ylmethoxy)amide

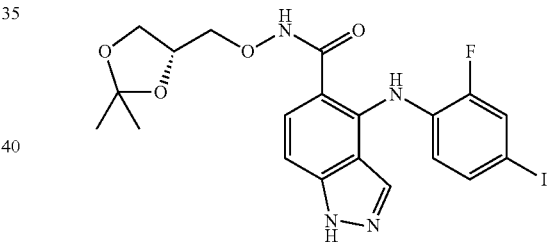

To a solution of 4-(2-fluoro-4-iodophenylamino)-1H-indazole-5-carboxylic acid (150 mg, 0.38 mmol) and O—((R)-2,2-dimethyl-[1,3]dioxolan-4-ylmethyl)-hydroxylamine (83 mg, 0.57 mmol) in DMF (4 mL) was added EDCI (80 mg, 0.42 mmol), HOBt (56 mg, 0.42 mmol) and DIPEA (70 µL, 0.42 mmol). The reaction mixture was stirred at room temperature for 3.5 hours before being concentrated in vacuo. The resultant residue was dissolved in ethyl acetate (10 mL), washed with aqueous saturated sodium bicarbonate solution (10 mL) and the aqueous fraction extracted twice with ethyl acetate (2×10 mL). The combined organic extracts were washed with brine (20 mL), dried (MgSO$_4$) and concentrated in vacuo. The resultant residue was subjected to flash chromatography (Si—SPE, gradient 0-10% methanol in DCM) to yield the title compound as a pale yellow solid (135 mg, 68%). LCMS (Method B): $R_T$=3.45 min, $[M+H]^+$=527.

Step 2: 4-(2-Fluoro-4-iodophenylamino)-1H-indazole-5-carboxylic acid ((R)-2,3-dihydroxy-propoxy)-amide To a solution of 4-(2-fluoro-4-iodophenylamino)-1H-indazole-5-carboxylic acid ((R)-2,2-dimethyl-[1,3]dioxolan-4- ylmethoxy)-amide (135 mg, 0.26 mmol) in methanol (4 mL) was added hydrochloric acid in dioxane (2 mL, 4N, 8 mmol). The reaction mixture was stirred at room temperature for 1 hour before being concentrated in vacuo. The resultant residue was subjected to flash chromatography (Si—SPE, gradient 0-10% methanol in DCM) to yield the title compound as an off white solid (94 mg, 75%). LCMS (Method A): $R_T$=7.67 min, [M+H]$^+$=487. $^1$H NMR (DMSO-d$_6$, 400 MHz) 13.20 (1H, s), 11.67 (1H, s), 9.94 (1H, s), 7.66 (1H, dd, J=10.30, 1.92 Hz), 7.47 (1H, d, J=8.79 Hz), 7.45-7.41 (1H, m), 7.22 (1H, s), 7.01 (1H, d, J=8.78 Hz), 6.92 (1H, t, J=8.64 Hz), 3.92-3.85 (1H, m), 3.76-3.58 (2H, m), 3.41-3.31 (2H, m).

Example 10

4-(4-Bromo-2-fluoro-phenylamino)-1H-indazole-5-carboxylic acid (2-hydroxy-ethoxy)-amide

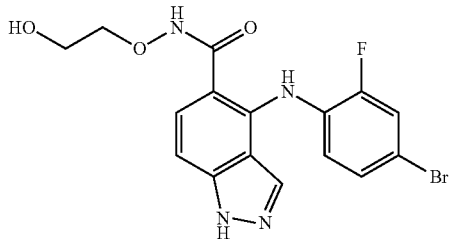 [SMILES: O=C(NOCCO)c1ccc2[nH]ncc2c1Nc1ccc(Br)cc1F]

Step 1: 4-(4-Bromo-2-fluorophenylamino)-1H-indazole-5-carboxylic acid (2-vinyloxy-ethoxy)-amide

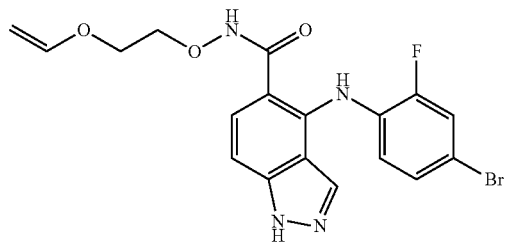 [SMILES: C=COCCONC(=O)c1ccc2[nH]ncc2c1Nc1ccc(Br)cc1F]

To a solution of 4-(4-bromo-2-fluorophenylamino)-1H-indazole-5-carboxylic acid (115 mg, 0.33 mmol) and O-(2-vinyloxy-ethyl)-hydroxylamine (51 mg, 0.49 mmol) in DMF (3 mL) was added EDCI (69 mg, 0.36 mmol), HOBt (49 mg, 0.36 mmol) and DIPEA (61 µL, 0.36 mmol). The reaction mixture was stirred at room temperature for 4 hours before being concentrated in vacuo. The resultant residue was dissolved in ethyl acetate (10 mL), washed with aqueous saturated sodium bicarbonate solution (10 mL) and the aqueous fraction extracted twice with ethyl acetate (2×10 mL). The combined organic extracts were washed with brine (20 mL), dried (MgSO$_4$) and concentrated in vacuo. The resultant residue was subjected to flash chromatography (Si—SPE, gradient 0-10% methanol in DCM) to yield the title compound as a pale yellow solid (96 mg, 67%). LCMS (Method B): $R_T$=3.43 min, [M–H]$^-$=433/435.

Step 2: 4-(4-Bromo-2-fluoro-phenylamino)-1H-indazole-5-carboxylic acid (2-hydroxy-ethoxy)-amide To a solution of 4-(4-bromo-2-fluorophenylamino)-1H-indazole-5-carboxylic acid (2-vinyloxy-ethoxy)-amide (96 mg, 0.22 mmol) in methanol (5 mL) was added hydrochloric acid (1 mL, 1N, 1 mmol). The reaction was stirred at room temperature for 30 minutes before being concentrated in vacuo. The resultant residue was dissolved in methanol (2 mL) and a few drops of water added causing the product to precipitate. The product was collected by filtration and dried in vacuo to yield the title compound as an off white solid (50 mg, 55%). LCMS (Method A): $R_T$=7.99 min, [M+H]$^+$=409/411. $^1$H NMR (DMSO-d$_6$, 400 MHz) 13.20 (1H, s), 11.61 (1H, s), 9.95 (1H, s), 7.58 (1H, dd, J=10.48, 2.24 Hz), 7.47 (1H, d, J=8.77 Hz), 7.29 (1H, ddd, J=8.60, 2.21, 1.05 Hz), 7.23 (1H, s), 7.08 (1H, t, J=8.81 Hz), 7.01 (1H, d, J=8.81 Hz), 4.68 (1H, s), 3.86 (2H, t, J=4.95 Hz), 3.56 (3H, s).

Example 11

4-(4-Bromo-2-fluoro-phenylamino)-1H-indazole-5-carboxylic acid ((S)-2-hydroxy-propoxy)-amide

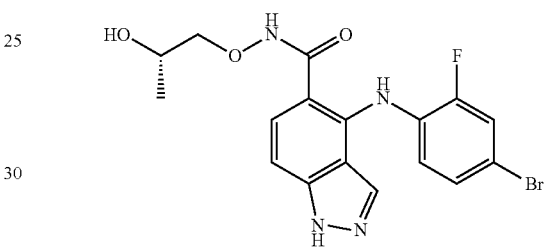

To a solution of 4-(4-bromo-2-fluorophenylamino)-1H-indazole-5-carboxylic acid (115 mg, 0.33 mmol) and (S)-1-aminooxy-propan-2-ol hydrochloride (63 mg, 0.49 mmol) in DMF (3 mL) was added EDCI (69 mg, 0.36 mmol), HOBt (49 mg, 0.36 mmol) and DIPEA (150 µL, 0.85 mmol). The reaction mixture was stirred at room temperature for 16 hours before being concentrated in vacuo. The resultant residue was dissolved in ethyl acetate (10 mL), washed with aqueous saturated sodium bicarbonate solution (10 mL) and the aqueous fraction extracted twice with ethyl acetate (2×10 mL). The combined organic fractions were washed with brine (20 mL), dried (MgSO$_4$) and concentrated in vacuo. The resultant residue was subjected to reverse phase preparative HPLC (10-90% acetonitrile/water 0.1% formic acid, Phenominex gemini PhC6, 5 micron, 250×20 mm). The resultant product was dissolved in ethyl acetate (5 mL) and washed with aqueous saturated sodium bicarbonate solution (10 mL). The aqueous fraction was extracted twice with ethyl acetate (2×10 mL) and the combined organic layers washed with brine (20 mL), dried (MgSO$_4$) and concentrated in vacuo to yield the title compound as a white solid (61 mg, 44%). LCMS (Method A): $R_T$=8.45 min, [M+H]$^+$=423/425. $^1$H NMR (DMSO-d$_6$, 400 MHz) 13.21 (1H, s), 11.63 (1H, s), 9.90 (1H, s), 7.58 (1H, dd, J=10.47, 2.24 Hz), 7.46 (1H, d, J=8.75 Hz), 7.29 (1H, ddd, J=8.59, 2.19, 1.06 Hz), 7.23 (1H, s), 7.08 (1H, t, J=8.80 Hz), 7.02 (1H, d, J=8.78 Hz), 4.77 (1H, d, J=4.15 Hz), 3.84-3.78 (1H, m), 3.70-3.61 (2H, m), 1.03 (3H, d, J=6.33 Hz).

Example 12

4-(2-Fluoro-4-iodo-phenylamino)-benzo[d]isothiazole-5-carboxylic acid (2-hydroxy-ethoxy)-amide

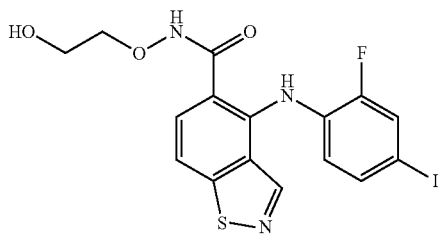 [SMILES: O=C(NOCCO)c1ccc2sncc2c1Nc1ccc(I)cc1F]

Step 1: 4-(2-Fluoro-4-iodo-phenylamino)-benzo[d]isothiazole 5-carboxylic acid (2-vinyloxy-ethoxy)-amide

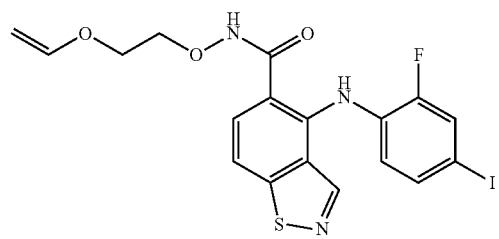 [SMILES: C=COCCONC(=O)c1ccc2sncc2c1Nc1ccc(I)cc1F]

To a solution of 4-(2-fluoro-4-iodo-phenylamino)-benzo[d]isothiazole-5-carboxylic acid (240 mg, 0.58 mmol) in THF (6 mL) was added DIPEA (396 µL, 2.34 mmol), O-(2-vinyloxy-ethyl)-hydroxylamine (119 mg, 1.15 mmol), HOBt (156 mg, 1.15 mmol) and EDCI (221 mg, 1.15 mmol) before the reaction mixture was stirred at room temperature for 18 hours. The reaction mixture was concentrated in vacuo and the resultant residue was partitioned between ethyl acetate and water. The organic extract was washed with aqueous saturated sodium bicarbonate solution then water, dried (Na$_2$SO$_4$) and concentrated in vacuo. The resultant residue was subjected to flash chromatography (Si—SPE, gradient 0-10% methanol in DCM) to yield the title compound (258 mg, 89%). LCMS (Method B): R$_T$=3.83 min, [M+H]$^+$=500.

Step 2: 4-(2-Fluoro-4-iodo-phenylamino)-benzo[d]isothiazole-5-carboxylic acid (2-hydroxy-ethoxy)-amide To a suspension of 4-(2-fluoro-4-iodo-phenylamino)-benzo[d]isothiazole-5-carboxylic acid (2-vinyloxy-ethoxy)-amide (258 mg, 0.52 mmol) in methanol (10 mL) was added hydrochloric acid (1.0 mL, 1M solution, 1.0 mmol) and the reaction mixture stirred at room temperature for 1 hour. The reaction mixture was concentrated in vacuo and the residue partitioned between ethyl acetate and saturated aqueous NaHCO$_3$. The organic layer was separated and washed with water then brine, dried (Na$_2$SO$_4$), filtered and concentrated in vacuo. The resultant residue was subjected to flash chromatography (Si—SPE, gradient 0-100% ethyl acetate in cyclohexane) to give the title compound as a white solid (140 mg, 57%). LCMS (Method A): R$_T$=9.72 min, [M+H]$^+$=474. $^1$H NMR (CD$_3$OD, 400 MHz) 8.57 (1H, s), 7.71 (1H, d, J=8.53 Hz), 7.69-7.61 (1H, m), 7.51 (1H, dd, J=10.43, 1.94 Hz), 7.33 (1H, d, J=8.54 Hz), 6.67 (1H, t, J=8.63 Hz), 3.92 (2H, t, J=4.60 Hz), 3.70 (2H, t, J=4.60 Hz).

Example 13

4-(2-Fluoro-4-methylsulfanyl-phenylamino)-1H-indazole-5-carboxylic acid (2-hydroxy-ethoxy)-amide

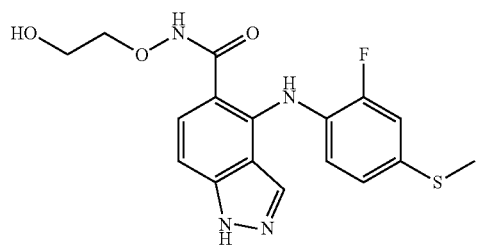 [SMILES: CSc1ccc(Nc2c(C(=O)NOCCO)ccc3[nH]ncc23)c(F)c1]

Step 1: 4-(2-Fluoro-4-methylsulfanyl-phenylamino)-1H-indazole-5-carboxylic acid (2-vinyloxy-ethoxy)-amide

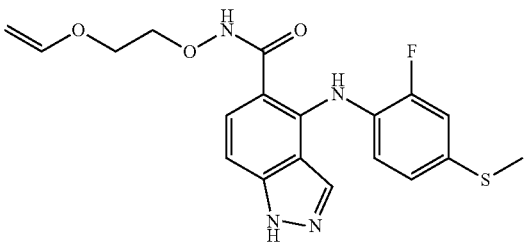 [SMILES: C=COCCONC(=O)c1ccc2[nH]ncc2c1Nc1ccc(SC)cc1F]

To a solution of 4-(2-fluoro-4-methylsulfanyl)-1H-indazole-5-carboxylic acid (85 mg, 0.268 mmol) and O-(2-vinyloxyethyl)-hydroxylamine (33 mg, 0.32 mmol) in DMF (10 mL) was added EDCI (66 mg, 0.32 mmol), HOBt (47 mg, 0.32 mmol) and DIPEA (68 µL, 0.40 mmol). The reaction mixture was stirred at room temperature for 18 hours. The reaction mixture was diluted with ethyl acetate and washed with saturated aqueous sodium hydrogen carbonate then water, dried (Na$_2$SO$_4$), filtered and concentrated in vacuo. The resultant solid was subjected to flash chromatography (Si—PPC, gradient 0 to 75% ethyl acetate in DCM) to give the title compound as a tan solid (45 mg, 42%). LCMS (Method A): R$_T$=3.40 min, [M+H]$^+$=403.

Step 2: 4-(2-Fluoro-4-methylsulfanyl-phenylamino)-1H-indazole-5-carboxylic acid (2-hydroxy-ethoxy)-amide A solution of 4-(2-fluoro-4-methylsulfanyl-phenylamino)-1H-indazole-5-carboxylic acid (2-vinyloxy-ethoxy)-amide (45 mg, 0.112 mmol) in methanol (5 mL) was treated with hydrochloric acid (1M, 0.225 mL, 0.22 mmol) and the reaction mixture stirred at room temperature for 2 hours. The reaction mixture was then concentrated in vacuo and the residue dissolved in methanol and to this solution was added water causing a precipitate to form which was filtered off. The filtrate was extracted twice with ethyl acetate, the combined extracts dried (Na$_2$SO$_4$), filtered and concentrated in vacuo. The crude product was combined with the earlier solid precipitate and subjected to flash chromatography (Si—

PPC, gradient 0 to 10% methanol in DCM) to give a solid. The solid was triturated in diethyl ether to give a pale tan solid (23 mg, 55%). LCMS (Method A) $R_T$ 7.79 [M+H]$^+$ 377. $^1$H NMR (MeOD, 400 MHz): 7.52-7.44 (1 H, m), 7.21-7.09 (3 H, m), 7.06 (1 H, dd, J=8.41, 2.08 Hz), 6.93 (1 H, d, J=8.88 Hz), 4.54 (1 H, s), 4.02-3.98 (2 H, m), 3.75 (2 H, dd, J=5.28, 4.05 Hz), 2.48 (3 H, s).

Example 14

4-(2-Fluoro-4-iodo-phenylamino)-1H-indazole-5-carboxylic acid ethoxy-amide

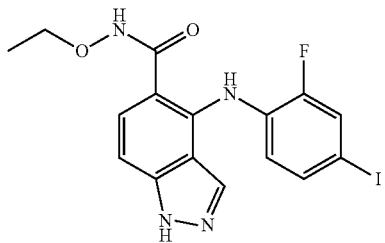 [SMILES: CCONC(=O)c1ccc2[nH]ncc2c1Nc1ccc(I)cc1F]

To a solution of 4-(2-fluoro-4-iodophenylamino)-1H-indazole-5-carboxylic acid (100 mg, 0.252 mmol) in DMF (3 mL) was added O-ethyl hydroxylamine hydrochloride (37 mg, 0.378 mmol), HOBt (37 mg, 0.277 mmol) and EDCI (53 mg, 0.277 mmol). The reaction mixture was stirred at room temperature for 1 hour then DIPEA (91 µl, 0.529 mmol) was added and the reaction stirred at room temperature for 18 hours. Additional quantities, as at the start of the reaction, of O-ethyl hydroxylamine hydrochloride, HOBt, EDCI and DIPEA were added to the reaction and stirring was continued for 4 hours. The reaction mixture was diluted with ethyl acetate and washed with saturated aqueous sodium hydrogen carbonate, the solid precipitate in the mixture was filtered off, washed with water to give the title compound (41 mg, 37%). LCMS (Method A): $R_T$=9.65 min, [M+H]$^+$=441. $^1$H NMR (DMSO-d$_6$, 400 MHz): 13.19 (1 H, s), 11.51 (1 H, s), 9.97 (1 H, s), 7.66 (1 H, dd, J=10.35, 1.95 Hz), 7.46 (1 H, d, J=8.78 Hz), 7.42 (1 H, dd, J=8.47, 1.84 Hz), 7.25 (1 H, s), 7.02 (1 H, d, J=8.76 Hz), 6.91 (1 H, t, J=8.66 Hz), 3.86 (2 H, q, J=7.04 Hz), 1.15 (3 H, t, J=7.03 Hz).

Example 15

4-(2-Fluoro-4-iodo-phenylamino)-1H-indazole-5-carboxylic acid (tetrahydro-pyran-4-yloxy)-amide

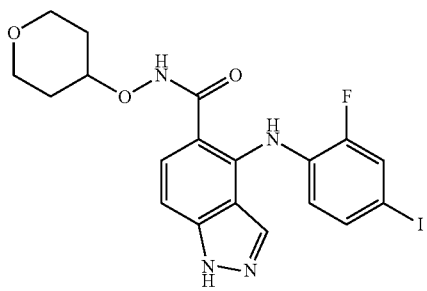 [SMILES: O=C(NOC1CCOCC1)c1ccc2[nH]ncc2c1Nc1ccc(I)cc1F]

To a solution of 4-(2-fluoro-4-iodophenylamino)-1H-indazole-5-carboxylic acid (100 mg, 0.252 mmol) in DMF (3 mL) was added 0-(tetrahydro-pyran-4-yl)-hydroxylamine (44 mg, 0.378 mmol), HOBt (37 mg, 0.277 mmol), EDCI (53 mg, 0.277 mmol) and DIPEA (92 µl, 0.529 mmol). The reaction was stirred at room temperature for 70 hours. The reaction mixture was diluted with ethyl acetate and washed with saturated aqueous sodium hydrogen carbonate then water, dried (Na$_2$SO$_4$), filtered and concentrated in vacuo. The resultant residue was subjected to flash chromatography (Si—PPC, gradient 30-100% ethyl acetate in cyclohexane). The resultant solid was triturated in methanol, the solid filtered off, washed with methanol to yield the title compound (33 mg, 26%). LCMS (Method A): $R_T$=9.27 min, [M+H]$^+$=497. $^1$H NMR (DMSO-d$_6$, 400 MHz): 13.19 (1 H, s), 11.44 (1 H, s), 9.87 (1 H, s), 7.65 (1 H, dd, J=10.36, 1.95 Hz), 7.48 (1H, d, J=8.77 Hz), 7.44-7.38 (1H, m), 7.28 (1 H, s), 7.03 (1 H, d, J=8.75 Hz), 6.89 (1 H, t, J=8.66 Hz), 4.02-3.93 (1 H, m), 3.84-3.76 (2 H, m), 3.36-3.28 (2 H, m), 1.88-1.81 (2 H, m), 1.51 (2 H, dddd, J=12.96, 9.42, 8.75, 4.11 Hz).

Example 16

4-(2-Fluoro-4-iodo-phenylamino)-1H-indazole-5-carboxylic acid cyclopropylmethoxy-amide

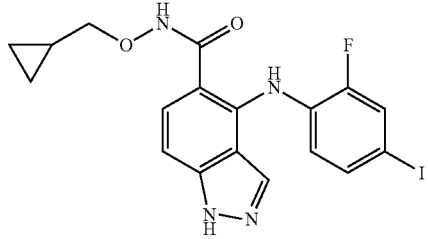 [SMILES: O=C(NOCC1CC1)c1ccc2[nH]ncc2c1Nc1ccc(I)cc1F]

To a solution of 4-(2-fluoro-4-iodophenylamino)-1H-indazole-5-carboxylic acid (70 mg, 0.176 mmol) and O-cyclopropylmethyl-hydroxylamine (23 mg, 0.21 mmol) in DMF (3 mL) was added EDCI (40 mg, 0.21 mmol), HOBt (28 mg, 0.21 mmol) and DIPEA (70 µL, 0.42 mmol). The reaction mixture was stirred at room temperature for 18 hours. The reaction mixture was diluted with ethyl acetate and washed with saturated aqueous sodium hydrogen carbonate then water, dried (Na$_2$SO$_4$), filtered and concentrated in vacuo. The resultant solid was triturated with a solution of hot methanol/water/NaHCO$_3$, the solid filtered off, washed with water to give the title compound as a pale pink solid (24 mg, 29%). LCMS (Method A): $R_T$=10.42 min, [M+H]$^+$=467. $^1$H NMR (DMSO-d$_6$, 400 MHz) 13.17 (1 H, s), 7.64 (1 H, dd, J=10.37, 1.95 Hz), 7.48 (1 H, d, J=8.76 Hz), 7.42-7.37 (1 H, m), 7.26 (1 H, d, J=0.95 Hz), 7.01 (1 H, dd, J=8.76, 0.99 Hz), 6.87 (1 H, t, J=8.66 Hz), 3.62 (2 H, d, J=7.13 Hz), 1.08-1.00 (1 H, m), 0.50-0.44 (2 H, m), 0.23-0.17 (2 H, m).

Example 17

4-(2-Fluoro-4-iodo-phenylamino)-1H-indazole-5-carboxylic acid methoxy-amide

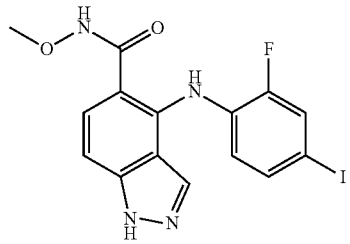 [SMILES: CONC(=O)c1ccc2[nH]ncc2c1Nc1ccc(I)cc1F]

To a solution of 4-(2-fluoro-4-iodophenylamino)-1H-indazole-5-carboxylic acid (70 mg, 0.176 mmol) and O-methylhydroxylamine (19 mg, 0.21 mmol) in DMF (2 mL) was added EDCI (40 mg, 0.21 mmol), HOBt (28 mg, 0.21 mmol) and DIPEA (70 μL, 0.42 mmol). The reaction mixture was stirred at room temperature for 18 hours. The reaction mixture was diluted with ethyl acetate and washed with saturated aqueous sodium hydrogen carbonate then water, dried (Na$_2$SO$_4$), filtered and concentrated in vacuo. The resultant solid was triturated with a solution of hot methanol/water/NaHCO$_3$, the solid filtered off, washed with water to give the title compound as a pale pink solid (33 mg, 44%). LCMS (Method A): R$_T$=9.09 min, [M+H]$^+$=427. $^1$H NMR (DMSO-d$_6$, 400 MHz) 13.20 (1 H, s), 11.62 (1 H, s), 9.99 (1 H, s), 7.66 (1 H, dd, J=10.33, 1.94 Hz), 7.46-7.40 (2 H, m), 7.23 (1 H, s), 7.01 (1 H, d, J=8.78 Hz), 6.92 (1 H, t, J=8.66 Hz), 3.64 (3 H, s).

Example 18

4-(2-Fluoro-4-iodo-phenylamino)-1H-indazole-5-carboxylic acid methoxy-methyl-amide

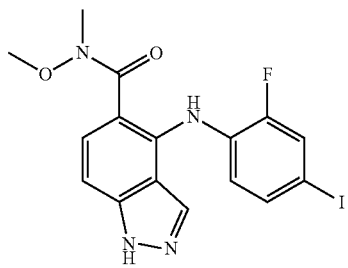 [SMILES: CON(C)C(=O)c1ccc2[nH]ncc2c1Nc1ccc(I)cc1F]

To a solution of 4-(2-fluoro-4-iodophenylamino)-1H-indazole-5-carboxylic acid (70 mg, 0.176 mmol) and N—O-dimethyl-hydroxylamine (21 mg, 0.21 mmol) in DMF (3 mL) was added EDCI (40 mg, 0.21 mmol), HOBt (28 mg, 0.21 mmol) and DIPEA (70 μL, 0.42 mmol). The reaction mixture was stirred at room temperature for 18 hours. The reaction mixture was diluted with ethyl acetate and washed with saturated aqueous sodium hydrogen carbonate then water, dried (Na$_2$SO$_4$), filtered and concentrated in vacuo then azeotroped with diethyl ether to give a pale tan foam (35 mg, 45%). LCMS (Method A): R$_T$=9.63 min, [M+H]$^+$=441. $^1$H NMR (DMSO-d$_6$, 400 MHz) 13.16 (1 H, s), 8.25 (1 H, s), 7.59-7.51 (2 H, m), 7.34-7.28 (2 H, m), 7.14 (1 H, d, J=8.55 Hz), 6.71 (1 H, t, J=8.73 Hz), 3.38 (3 H, s), 3.10 (3 H, s).

Example 19

[4-(2-Fluoro-4-iodo-phenylamino)-1H-indazol-5-yl]-(3-hydroxy-azetidin-1-yl)-methanone

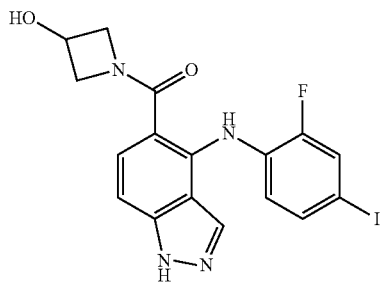 [SMILES: O=C(c1ccc2[nH]ncc2c1Nc1ccc(I)cc1F)N1CC(O)C1]

To a solution of 4-(2-fluoro-4-iodophenylamino)-1H-indazole-5-carboxylic acid (70 mg, 0.176 mmol) and 3-hydroxyazetidine hydrochloride (23 mg, 0.21 mmol) in DMF (1 mL) was added EDCI (40 mg, 0.21 mmol), HOBt (28 mg, 0.21 mmol) and DIPEA (70 μL, 0.42 mmol). The reaction mixture was stirred at room temperature for 18 hours. The reaction mixture was diluted with ethyl acetate and washed with saturated aqueous sodium hydrogen carbonate then water, dried (Na$_2$SO$_4$), filtered and concentrated in vacuo. The resultant residue was triturated in cyclohexane to give the title compound as a pale tan solid (39 mg, 49%). LCMS (Method A): R$_T$=8.23 min, [M+H]$^+$=453. $^1$H NMR (DMSO-d$_6$, 400 MHz) 13.17 (1 H, s), 9.55 (1 H, s), 7.63 (1 H, dd, J=10.47, 1.94 Hz), 7.41-7.37 (1 H, m), 7.37 (1 H, s), 7.32 (1 H, d, J=8.69 Hz), 7.05-7.00 (1 H, m), 6.92-6.82 (1 H, m), 5.67 (1 H, d, J=6.13 Hz), 4.44-4.37 (1 H, m), 4.24 (2 H, br, s), 3.83 (2 H, br, s).

Example 20

4-(2-Fluoro-4-iodo-phenylamino)-benzo[d]isothiazole-5-carboxylic acid ((S)-2-hydroxy-propoxy)-amide

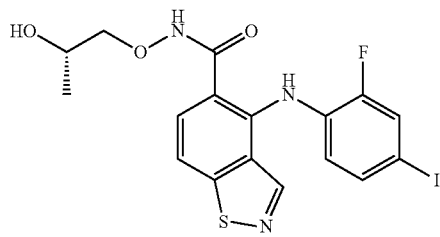 [SMILES: C[C@H](O)CONC(=O)c1ccc2sncc2c1Nc1ccc(I)cc1F]

To a solution of 4-(2-fluoro-4-iodo-phenylamino)-benzo[d]iso-thiazole-5-carboxylic acid (150 mg, 0.362 mmol), diisopropylethylamine (0.25 mL, 1.45 mmol), HOBt (98 mg, 0.724 mmol) and (S)-1-aminooxy-propan-2-ol (92 mg, 0.724 mmol in DMF (2 mL) was added EDCI (139 mg, 0.724 mmol). The reaction mixture was stirred for 16 hours at room temperature, diluted with ethyl acetate, and washed with water, a saturated aqueous solution of sodium hydrogen carbonate, then brine before being dried (Na$_2$SO$_4$), filtered and concentrated in vacuo. The resultant residue was subjected to flash chromatography (Si—PPC, gradient 30% to 80%, EtOAc in cyclohexane) to afford the title compound as a solid (45 mg, 26%). LCMS (method A): R$_T$=10.26 min, [M+H]$^+$=488. $^1$H NMR (DMSO-d$_6$, 400 MHz) 11.72 (1 H, s), 9.22 (1 H, s), 8.69 (1 H, s), 7.86-7.81 (1 H, m), 7.64-7.55 (2 H, m), 7.30 (1 H, dd, J=8.47, 1.83 Hz), 6.63 (1 H, t, J=8.72 Hz), 4.73 (1 H, s), 3.76-3.68 (1 H, m), 3.53 (2 H, d, J=5.78 Hz), 0.99 (3 H, d, J=6.33 Hz).

Example 21

4-(2-Fluoro-4-iodo-phenylamino)-benzo[d]isothiazole-5-carboxylic acid ((R)-2,3-dihydroxy-propoxy)-amide

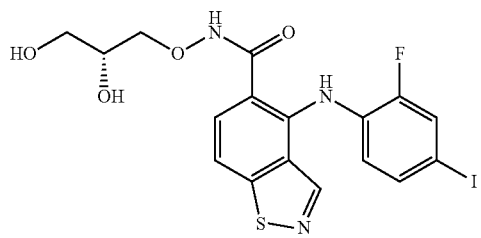 [SMILES: O=C(NOC[C@H](O)CO)c1ccc2sncc2c1Nc1ccc(I)cc1F]

Step 1: 4-(2-Fluoro-4-iodo-phenylamino)-benzo[d]isothiazole-5-carboxylic acid ((R)-2,2-dimethyl-[1,3]-dioxolan-4-ylmethoxy)-amide

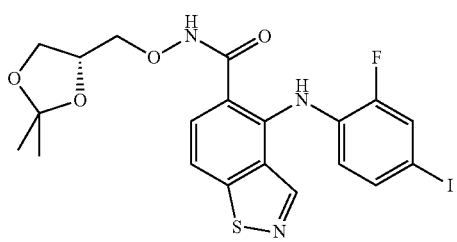 [SMILES: CC1(C)OC[C@H](CONC(=O)c2ccc3sncc3c2Nc2ccc(I)cc2F)O1]

To a solution of 4-(2-fluoro-4-iodo-phenylamino)-benzo[d]iso-thiazole-5-carboxylic acid (250 mg, 0.604 mmol), diisopropylethylamine (0.42 mL, 2.42 mmol), HOBt (163 mg, 0.1.21 mmol) and O—(((R)-2,2-dimethyl-[1,3]dioxolan-4-ylmethyl)-hydroxylamine (178 mg, 1.21 mmol) in DMF (2 mL) was added EDCI (232 mg, 1.21 mmol). The reaction mixture was stirred for 16 hours at room temperature, diluted with ethyl acetate, and washed with water, a saturated aqueous solution of sodium hydrogen carbonate, then brine before being dried (Na$_2$SO$_4$), filtered and concentrated in vacuo. The resultant residue was subjected to flash chromatography (Si—PPC, gradient 0% to 50%, EtOAc in cyclohexane) to afford the title compound as a solid (142 mg, 43%). LCMS (method B): R$_T$=3.92 min, [M+H]$^+$=544.

Step 2: 4-(2-Fluoro-4-iodo-phenylamino)-benzo[d]isothiazole-5-carboxylic acid ((R)-2,3-dihydroxy-propoxy)-amide To a solution of 4-(2-Fluoro-4-iodo-phenylamino)-benzo[d]isothiazole-5-carboxylic acid ((R)-2,2-dimethyl-[1,3]dioxolan-4-ylmethoxy)-amide (142 mg, 0.261 mmol) in MeOH (2 mL) was added a 4M HCl solution in dioxane (2 mL). The reaction mixture was stirred at room temperature for 2 hours before being concentrated in vacuo. The resultant residue was taken up in ethyl acetate, washed with a saturated aqueous solution of sodium hydrogen carbonate, water then brine, dried (Na$_2$SO$_4$), filtered and concentrated in vacuo. The resultant residue was triturated in ethyl acetate/cyclohexane to afford the title compound as a solid (73 mg, 56%). LCMS (method A): R$_T$=8.97 min, [M+H]$^+$=504. NMR (DMSO-d$_6$, 400 MHz) 11.78 (1 H, s), 9.28 (1 H, s), 8.64 (1 H, s), 7.84 (1 H, dd, J=8.48, 0.92 Hz), 7.64-7.57 (2 H, m), 7.31 (1 H, dd, J=8.47, 1.83 Hz), 6.65 (1 H, t, J=8.71 Hz), 4.80 (1 H, s), 4.54 (1 H, s), 3.80 (1 H, t, J=6.46 Hz), 3.68-3.61 (2 H, m), 3.32 (2 H, s).

Example 22

7-(2-Fluoro-4-methylsulfanyl-phenylamino)-benzo[d]isothiazole-6-carboxylic acid ((R)-2,3-dihydroxy-propoxy)-amide

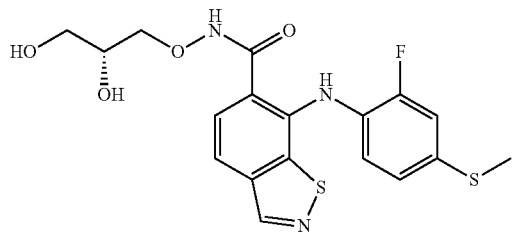 [SMILES: CSc1ccc(Nc2c(C(=O)NOC[C@H](O)CO)ccc3cnsc23)c(F)c1]

Step 1: 7-(2-Fluoro-4-methylsulfanyl-phenylamino)-benzo[d]isothiazole-6-carboxylic acid ((R)-2,2-dimethyl-[1,3]dioxolan-4-ylmethoxy)-amide

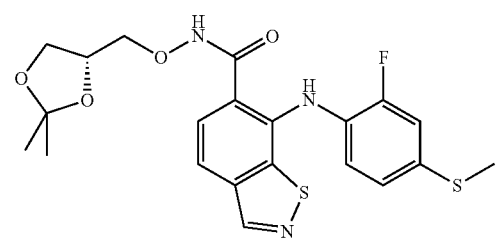 [SMILES: CSc1ccc(Nc2c(C(=O)NOC[C@H]3COC(C)(C)O3)ccc3cnsc23)c(F)c1]

To a solution of 7-(2-fluoro-4-methylsulfanyl-phenylamino)-benzo[d]isothiazole-6-carboxylic acid (200 mg, 0.60 mmol) and diisopropylethylamine (0.31 mL, 1.80 mmol) in DMF (2 mL) were added 0-((R)-2,2-dimethyl-[1,3]dioxolan-4-ylmethyl)-hydroxylamine (176 mg, 1.20 mmol), EDCI (230 mg, 1.20 mmol) and HOBt (162 mg, 1.20 mmol). The reaction mixture was stirred for 18 hours at room temperature, and then diluted with ethyl acetate and washed with water, a saturated aqueous solution of sodium hydrogen carbonate and brine before being dried (Na$_2$SO$_4$), filtered and concentrated in vacuo. The resultant residue was subjected to flash chromatography (Si—PPC, gradient 50% to 100%, Et$_2$O in pentane) to afford the title compound as a yellow oil (171 mg, 61%). LCMS (method B): R$_T$=3.85 min, [M+H]$^+$=464.

Step 2: 7-(2-Fluoro-4-methylsulfanyl-phenylamino)-benzo[d]isothiazole-6-carboxylic acid ((R)-2,3-dihydroxy-propoxy)-amide To a solution of 7-(2-fluoro-4-methylsulfanyl-phenylamino)-benzo[d]isothiazole-6-carboxylic acid ((R)-2,2-dimethyl-[1,3]dioxolan-4-ylmethoxy)-amide (170 mg, 0.37 mmol) in MeOH (2 mL) was added a 1.0M aqueous solution of hydrochloric acid (0.80 mL). The reaction mixture was stirred at room temperature for 1 hour before being concentrated in vacuo. The residue was taken up in ethyl acetate, washed with a saturated aqueous solution of sodium hydrogen carbonate followed by brine, dried (Na$_2$SO$_4$), filtered and evaporated in vacuo. The resultant residue was subjected to flash chromatography (Si—PPC, gradient 0% to 100%, MeOH in DCM) to afford the title compound as a yellow solid (42 mg, 26%). LCMS (Method A): R$_T$=8.80 min, [M+H]$^+$=478. $^1$H NMR (CD$_3$OD) 8.81 (1 H, s), 7.63-7.56 (2 H, m), 7.12-7.04 (3 H, m), 4.10-4.04 (1 H, m), 3.98-3.86 (2 H, m), 3.64-3.55 (2 H, m), 2.50 (3 H, s).

Example 23

7-(4-Cyclopropyl-2-fluoro-phenylamino)-benzo[d]isothiazole-6-carboxylic acid ((R)-2,3-dihydroxy-propoxy)-amide

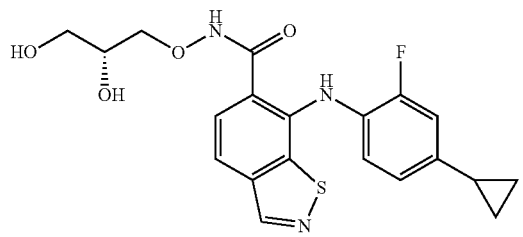 [SMILES: O=C(NOC[C@H](O)CO)c1ccc2cnsc2c1Nc1ccc(C2CC2)cc1F]

Step 1: 7-(4-Cyclopropyl-2-fluoro-phenylamino)-benzo[d]isothiazole-6-carboxylic acid ((R)-2,3-dihydroxy-propoxy)-amide To a solution of 7-(4-cyclopropyl-2-fluoro-phenylamino)-benzo[d]isothiazole-6-carboxylic acid (155 mg, 0.47 mmol) and diisopropylethylamine (0.10 mL, 0.61 mmol) in DMF (5 mL) were added O—((R)-2,2-dimethyl-[1,3]dioxolan-4-yl-methyl)-hydroxylamine (97 mg, 0.66 mmol), EDCI (117 mg, 0.61 mmol) and HOBt (83 mg, 0.61 mmol). The reaction mixture was stirred for 2 hours at room temperature, diluted with ethyl acetate, washed with water, a saturated aqueous solution of sodium hydrogen carbonate, then brine before being dried (Na$_2$SO$_4$), filtered and concentrated in vacuo. The resultant residue was taken in MeOH (10 mL) and a 4.0M solution of hydrochloric acid in dioxane (1.0 mL) was added. The reaction mixture was stirred at room temperature for 1 hour before being diluted with ethyl acetate, washed with a saturated aqueous solution of sodium hydrogen carbonate then brine, dried (Na$_2$SO$_4$), filtered and evaporated in vacuo. The resultant residue was subjected to reverse-phase HPLC (Gemini 5 micron C$_{18}$ 250×21.20 mm column, 0.1% formic acid, gradient acetonitrile/water, 15 to 95%, ramp time 20 minutes) to afford the title compound as a yellow solid (115 mg, 59%). LCMS (method A): R$_T$=9.02 min, [M+H]$^+$=418. $^1$H NMR (DMSO-d$_6$, 400 MHz) 9.98 (1 H, s), 8.97 (1 H, s), 7.72 (1 H, s), 7.61 (1 H, d, J=8.35 Hz), 7.09-6.90 (3 H, m), 3.95 (1 H, dd, J=9.94, 3.81 Hz), 3.79 (2 H, d, J=16.92 Hz), 3.40 (2 H, d, J=5.46 Hz), 2.03-1.94 (1 H, m), 1.03-0.97 (2 H, m), 0.77-0.71 (2 H, m).

Example 24

7-(4-Bromo-2-fluoro-phenylamino)-benzo[d]isothiazole-6-carboxylic acid ((R)-2,3-dihydroxy-propoxy)-amide

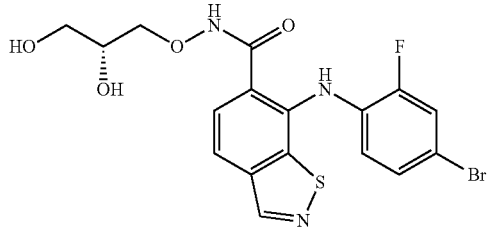 [SMILES: O=C(NOC[C@H](O)CO)c1ccc2cnsc2c1Nc1ccc(Br)cc1F]

Step 1: 7-(4-Bromo-2-fluoro-phenylamino)-benzo[d]isothiazole-6-carboxylic acid ((R)-2,2-dimethyl-[1,3]-dioxolan-4-ylmethoxy)-amide

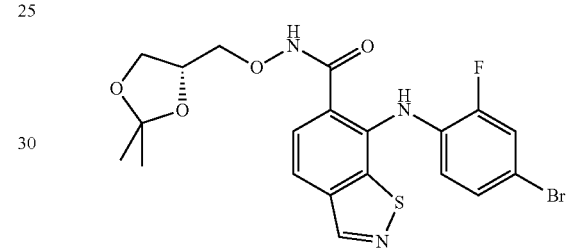

To a solution of 7-(4-bromo-2-fluoro-phenylamino)-benzo[d]isothiazole-6-carboxylic acid (584 mg, 1.59 mmol) and diisopropylethylamine (0.82 mL, 4.77 mmol) in DMF (6 mL) were added O—((R)-2,2-dimethyl-[1,3]dioxolan-4-ylmethyl)-hydroxylamine (468 mg, 3.18 mmol), EDCI (611 mg, 3.18 mmol) and HOBt (430 mg, 3.18 mmol). The reaction mixture was stirred for 18 hours at room temperature, diluted with ethyl acetate, and washed with water, a saturated aqueous solution of sodium hydrogen carbonate then brine before being dried (Na$_2$SO$_4$), filtered and concentrated in vacuo. The resultant residue was subjected to flash chromatography (Si—PPC, gradient 50% to 100%, TBME in cyclohexane) to afford the title compound as a yellow oil (370 mg, 47%). LCMS (method B): R$_T$=3.96 min, [M+H]$^+$=496/498.

Step 2: 7-(4-Bromo-2-fluoro-phenylamino)-benzo[d]isothiazole-6-carboxylic acid ((R)-2,3-dihydroxy-propoxy)-amide To a solution of 7-(4-bromo-2-fluoro-phenylamino)-benzo[d]isothiazole-6-carboxylic acid ((R)-2,2-dimethyl-[1,3]dioxolan-4-ylmethoxy)-amide (370 mg, 0.75 mmol) in MeOH (4 mL) was added a 1.0M aqueous solution of hydrochloric acid (1.50 mL). The reaction mixture was stirred at room temperature for 2 hours before being concentrated in vacuo. The resultant residue was taken up in ethyl acetate, washed with a saturated aqueous solution of sodium hydrogen carbonate then brine, dried (Na$_2$SO$_4$), filtered and evaporated in vacuo. The resultant residue was subjected to flash chromatography (Si—PPC, gradient 0% to 100%, MeOH in DCM) to afford the title compound as a yellow solid (242 mg, 71%). LCMS (method A): R$_T$=8.80 min, [M+H]$^+$=456/458. $^1$H NMR (CD$_3$OD, 400 MHz) 8.87 (1 H, s), 7.76-7.70 (1 H, m), 7.61 (1 H, d, J=8.36 Hz), 7.42-7.36 (1 H, m), 7.30-7.25 (1 H, m), 6.95 (1 H, t, J=8.66 Hz), 4.06 (1 H, dd, J=10.08, 3.55 Hz), 3.96-3.83 (2 H, m), 3.64-3.54 (2 H, m).

Example 25

7-(4-Bromo-2-fluoro-phenylamino)-benzo[d]isothiazole-6-carboxylic acid (2-hydroxy-ethoxy)-amide

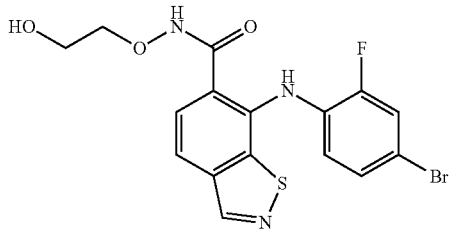 [SMILES: O=C(NOCCO)c1ccc2cnsc2c1Nc1ccc(Br)cc1F]

Step 1: 7-(4-Bromo-2-fluoro-phenylamino)-benzo[d]isothiazole-6-carboxylic acid (2-vinyloxy-ethoxy)-amide

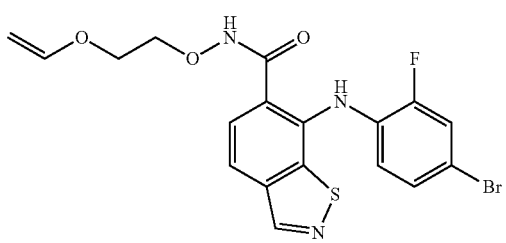 [SMILES: C=COCCONC(=O)c1ccc2cnsc2c1Nc1ccc(Br)cc1F]

To a solution of 7-(4-bromo-2-fluoro-phenylamino)-benzo[d]isothiazole-6-carboxylic acid (210 mg, 0.57 mmol) and diisopropylethylamine (0.29 mL, 1.71 mmol) in DMF (2 mL) were added O-(2-vinyloxy-ethyl)-hydroxylamine (117 mg, 1.14 mmol), EDCI (220 mg, 1.14 mmol) and HOBt (154 mg, 1.14 mmol). The reaction mixture was stirred for 18 hours at room temperature, diluted with ethyl acetate and washed with water, a saturated aqueous solution of sodium hydrogen carbonate then brine before being dried (Na$_2$SO$_4$), filtered and concentrated in vacuo. The resultant residue was subjected to flash chromatography (Si—PPC, gradient 0% to 100%, TBME in cyclohexane) to afford the title compound as a yellow oil (95 mg, 37%). LCMS (method B): R$_T$=3.90 min, [M+H]$^+$=452/454.

Step 2: 7-(4-Bromo-2-fluoro-phenylamino)-benzo[d]isothiazole-6-carboxylic acid (2-hydroxy-ethoxy)-amide To a solution of 7-(4-bromo-2-fluoro-phenylamino)-benzo[d]isothiazole-6-carboxylic acid (2-vinyloxy-ethoxy)-amide (95 mg, 0.21 mmol) in MeOH (4 mL) was added a 1.0M aqueous solution of hydrochloric acid (0.42 mL). The reaction mixture was stirred at room temperature for 1 hour before being concentrated in vacuo. The resultant residue was taken up in ethyl acetate, washed with a saturated aqueous solution of sodium hydrogen carbonate then brine, dried (Na$_2$SO$_4$), filtered and evaporated in vacuo. The resultant residue was subjected to flash chromatography (Si—PPC, gradient 0% to 100%, ethyl acetate in DCM) to afford the title compound as a yellow solid (62 mg, 70%). LCMS (method A): R$_T$=9.51 min, [M+H]$^+$=426/428. $^1$H NMR (CDCl$_3$, 400 MHz) 9.37 (1 H, s), 8.85 (1 H, s), 8.76 (1 H, s), 7.51 (1 H, d, J=8.40 Hz), 7.43 (1 H, d, J=8.40 Hz), 7.34-7.29 (1 H, m), 7.28 (1 H, d, J=8.75 Hz), 7.02 (1 H, t, J=8.46 Hz), 4.10 (2 H, t, J=4.09 Hz), 3.91 (1 H, s), 3.80 (2 H, s).

Example 26

7-(2-Fluoro-4-iodo-phenylamino)-benzo[d]isothiazole-6-carboxylic acid (2-hydroxy-ethoxy)-amide

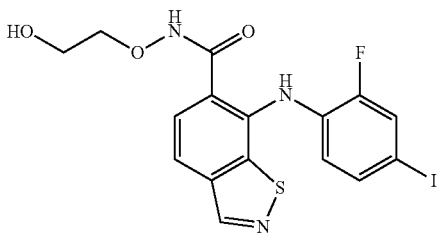 [SMILES: O=C(NOCCO)c1ccc2cnsc2c1Nc1ccc(I)cc1F]

Step 1: 7-(2-Fluoro-4-iodo-phenylamino)-benzo[d]isothiazole-6-carboxylic acid (2-vinyloxy-ethoxy)-amide

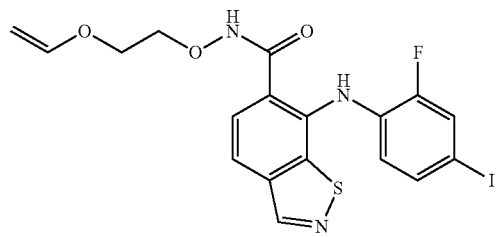 [SMILES: C=COCCONC(=O)c1ccc2cnsc2c1Nc1ccc(I)cc1F]

To a solution of 7-(2-fluoro-4-iodo-phenylamino)-benzo[d]isothiazole-6-carboxylic acid (328 mg, 0.79 mmol) and diisopropylethylamine (0.41 mL, 2.37 mmol) in DMF (2 mL) were added O-(2-vinyloxy-ethyl)-hydroxylamine (163 mg, 1.58 mmol), EDCI (303 mg, 1.58 mmol) and HOBt (213 mg, 1.58 mmol). The reaction mixture was stirred for 18 hours at room temperature, diluted with ethyl acetate, and washed with water then a saturated aqueous solution of sodium hydrogen carbonate, then brine, before being dried (Na$_2$SO$_4$), filtered and concentrated in vacuo. The resultant residue was subjected to flash chromatography (Si—PPC, gradient 0% to 100%, TBME in cyclohexane) to afford the title compound as a yellow foam (194 mg, 49%). LCMS (method B): R$_T$=3.99 min, [M+H]$^+$=500.

Step 2: 7-(2-Fluoro-4-iodo-phenylamino)-benzo[d]isothiazole-6-carboxylic acid (2-hydroxy-ethoxy)-amide To a solution of 7-(2-fluoro-4-iodo-phenylamino)-benzo[d]isothiazole-6-carboxylic acid (2-vinyloxy-ethoxy)-amide (187 mg, 0.37 mmol) in MeOH (4 mL) was added a 1.0M aqueous solution of hydrochloric acid (0.75 mL). The reaction mixture was stirred at room temperature for 1 hour before being concentrated in vacuo. The resultant residue was taken up in ethyl acetate, washed with a saturated aqueous solution of sodium hydrogen carbonate, then brine, dried (Na$_2$SO$_4$), filtered and evaporated in vacuo. The resultant residue was subjected to flash chromatography (Si—PPC, gradient 0% to 100%, ethyl acetate in DCM) to afford the title compound as a yellow solid (128 mg, 72%). LCMS (method A): R$_T$=9.81 min, [M+H]$^+$=474. $^1$H NMR (CDCl$_3$, 400 MHz) 9.33 (1 H, s), 8.86 (1 H, s), 8.77 (1 H, s), 7.55-7.40 (4 H, m), 6.84 (1 H, t, J=8.30 Hz), 4.10 (2 H, t, J=4.16 Hz), 3.91 (1 H, t, J=6.45 Hz), 3.80 (2 H, t, J=4.55 Hz).

Example 27

7-(2-Fluoro-4-iodo-phenylamino)-benzo[d]isothiazole-6-carboxylic acid ((R)-2,3-dihydroxy-propoxy)amide

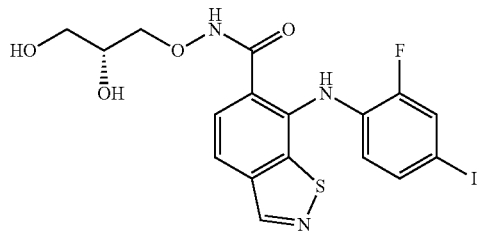 [SMILES: O=C(NOC[C@H](O)CO)c1ccc2cnsc2c1Nc1ccc(I)cc1F]

Step 1: 7-(2-Fluoro-4-iodo-phenylamino)-benzo[d]isothiazole-6-carboxylic acid ((R)-2,2-dimethyl-[1,3]dioxolan-4-ylmethoxy)-amide

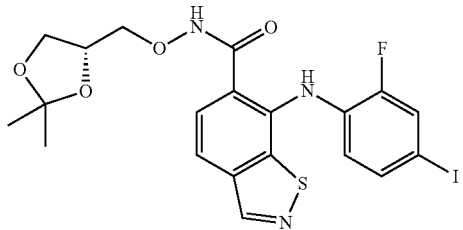 [SMILES: CC1(C)OC[C@H](CONC(=O)c2ccc3cnsc3c2Nc2ccc(I)cc2F)O1]

To a solution of 7-(2-fluoro-4-iodo-phenylamino)-benzo[d]isothiazole-6-carboxylic acid (377 mg, 0.91 mmol) and diisopropylethylamine (0.47 mL, 2.73 mmol) in DMF (4 mL) were added O—((R)-2,2-dimethyl-[1,3]dioxolan-4-ylmethyl)-hydroxylamine (268 mg, 1.82 mmol), EDCI (349 mg, 1.82 mmol) and HOBt (246 mg, 1.82 mmol). The reaction mixture was stirred for 18 hours at room temperature, diluted with ethyl acetate, and washed with water, a saturated aqueous solution of sodium hydrogen carbonate, then brine before being dried (Na$_2$SO$_4$), filtered and concentrated in vacuo. The resultant residue was subjected to flash chromatography (Si—PPC, gradient 0% to 100%, TBME in cyclohexane) to afford the title compound as a yellow solid (266 mg, 54%). LCMS (method B): R$_T$=4.04 min, [M+H]$^+$=544.

Step 2: 7-(2-Fluoro-4-iodo-phenylamino)-benzo[d]isothiazole-6-carboxylic acid ((R)-2,3-dihydroxy-propoxy)amide To a solution of 7-(2-fluoro-4-iodo-phenylamino)-benzo[d]isothiazole-6-carboxylic acid ((R)-2,2-dimethyl-[1,3]dioxolan-4-ylmethoxy)-amide (263 mg, 0.48 mmol) in MeOH (10 mL) was added a 1.0M aqueous solution of hydrochloric acid (0.97 mL). The reaction mixture was stirred at room temperature for 18 hours before being concentrated in vacuo. The resultant residue was taken up in ethyl acetate, washed with a saturated aqueous solution of sodium hydrogen carbonate then brine, dried (Na$_2$SO$_4$), filtered and evaporated in vacuo. The resultant residue was subjected to flash chromatography (Si—PPC, gradient 0% to 100%, ethyl acetate in DCM) to afford the title compound as a yellow solid (127 mg, 53%). LCMS (method A): R$_T$=9.05 min, [M+H]$^+$=504. $^1$H NMR (CD$_3$OD, 400 MHz) 8.88 (1 H, s), 7.74 (1 H, d, J=8.36 Hz), 7.61 (1 H, d, J=8.35 Hz), 7.53 (1 H, dd, J=10.01, 1.93 Hz), 7.44 (1 H, ddd, J=8.36, 1.93, 1.06 Hz), 6.76 (1 H, t, J=8.53 Hz), 4.05 (1 H, dd, J=10.03, 3.50 Hz), 3.96-3.83 (2 H, m), 3.63-3.52 (2 H, m).

Example 28

Cyclopropanesulfonic acid [4-(2-fluoro-4-iodo-phenylamino)-1H-indazol-5-yl]-amide

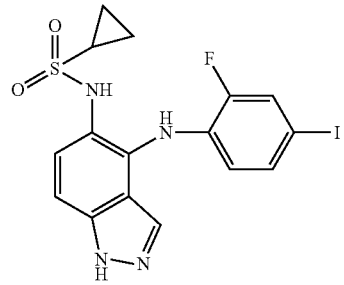 [SMILES: O=S(=O)(Nc1ccc2[nH]ncc2c1Nc1ccc(I)cc1F)C1CC1]

Step 1: 5-Cyclopropanesulfonylamino-4-(2-fluoro-4-iodo-phenylamino)-indazole-1-carboxylic acid tert-butyl ester

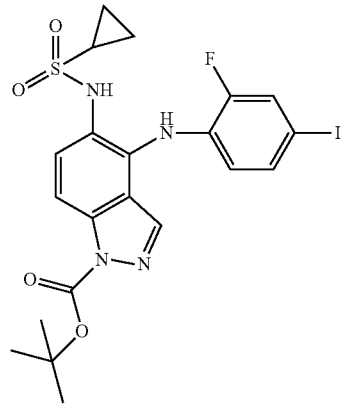 [SMILES: CC(C)(C)OC(=O)n1ncc2c(Nc3ccc(I)cc3F)c(NS(=O)(=O)C3CC3)ccc21]

To a solution of 5-amino-4-(2-fluoro-4-iodo-phenylamino)-indazole-1-carboxylic acid tert-butyl ester (200 mg, 0.43 mmol) in pyridine (2 mL) was added cyclopropyl sulfonyl chloride (0.218 mL, 2.14 mmol) and the mixture stirred at room temperature for 1 hour. The reaction mixture was concentrated in vacuo and the residue partitioned between ethyl acetate (100 mL) and water (100 mL). The organic layer was separated, washed with brine, then dried (Na$_2$SO$_4$), filtered and concentrated in vacuo. The resultant residue was subjected to flash chromatography (Si—PPC, gradient 10-35% ethyl acetate in cyclohexane) to yield the title compound (206 mg, 84%). LCMS (Method B): $R_T$=4.17 min, [MH]$^+$=573.

Step 2: Cyclopropanesulfonic acid [4-(2-fluoro-4-iodo-phenylamino)-1H-indazol-5-yl]-amide To a solution of 5-cyclopropanesulfonylamino-4-(2-fluoro-4-iodo-phenylamino)-indazole-1-carboxylic acid tert-butyl ester (206 mg, 0.36 mmol) in DCM (8 mL) was added TFA (1 mL) and the reaction mixture stirred at room temperature for 2 hours. Additional TFA (1 mL) was added and stirring continued for a further 1 hour before the reaction mixture was concentrated in vacuo and the residue azeotroped with DCM, methanol and then DCM again. The resultant residue was triturated with diethyl ether, the solid filtered off and dried under vacuum at 40° C. to give the title compound as a yellow solid (83 mg, 49%). LCMS (Method A): $R_T$=10.03 [M+H]$^+$=437, $^1$H NMR (DMSO-d$_6$, 400 MHz): 13.14 (1 H, s), 9.07 (1 H, s), 7.80 (1 H, s), 7.57 (1 H, dd, J=10.84, 1.96 Hz), 7.39 (1 H, s), 7.31 (1 H, d, J=8.74 Hz), 7.25-7.20 (2 H, m), 6.45 (1 H, t, J=8.84 Hz), 2.40-2.32 (1 H, m), 0.75-0.62 (4 H, m), −0.05 (1 H, t, J=3.33 Hz).

Example 29

Cyclopropanesulfonic acid [4-(2-fluoro-4-iodo-phenylamino)-6-methoxy-1H-indazol-5-yl]-amide

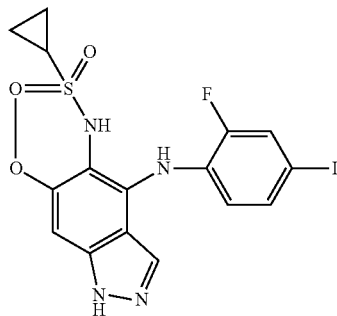

Step 1: 5-Cyclopropanesulfonylamino-4-(2-fluoro-4-iodo-phenylamino)-6-methoxy-indazole-1-carboxylic acid tert-butyl ester

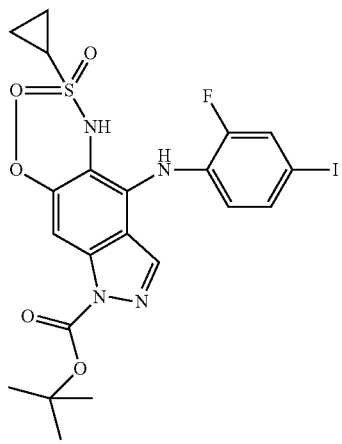

To a solution of 5-amino-4-(2-fluoro-4-iodo-phenylamino)-6-methoxy-indazole-1-carboxylic acid tert-butyl ester (200 mg, 0.401 mmol) in pyridine (2 mL) was added cyclopropyl sulfonyl chloride (281 mg, 2.0 mmol) and the reaction mixture stirred at room temperature for 18 hours. The reaction mixture was treated with water and extracted twice with ethyl acetate. The combined organic extracts were washed with water, dried (Na$_2$SO$_4$), filtered and concentrated in vacuo to give an oily residue. The residue was subjected to flash chromatography (Si—PPC, gradient 0 to 25% ethyl acetate in cyclohexane) to give the title compound as an off-white foam (217 mg, 89%). LCMS (Method B) $R_T$=4.16 min, [M+H]$^+$=603.

Step 2: Cyclopropanesulfonic acid [4-(2-fluoro-4-iodo-phenylamino)-6-methoxy-1H-indazol-5-yl]-amide A solution of 5-cyclopropanesulfonylamino-4-(2-fluoro-4-iodo-phenylamino)-6-methoxy-indazole-1-carboxylic acid tert-butyl ester (217 mg, 0.36 mmol) in DCM (5 mL) was treated with TFA (2 mL) and the reaction mixture stirred at room temperature for 1 hour. The reaction mixture was concentrated in vacuo and the residue triturated with diethyl ether to give the title compound as an off-white solid (102 mg, 52%). LCMS (method A): $R_T$=10.17 [M+H]$^+$=503. $^1$H NMR (DMSO-d$_6$, 400 MHz): 12.92 (1 H, s), 8.72 (1 H, s), 7.60-7.52 (2 H, m), 7.34-7.24 (2 H, m), 6.71 (1 H, s), 6.53 (1 H, t, J=8.80 Hz), 3.84 (3 H, s), 2.53-2.46 (1 H, m), 0.84-0.73 (2 H, m), 0.72-0.66 (2 H, m).

We claim:
1. A compound of formula I or II:

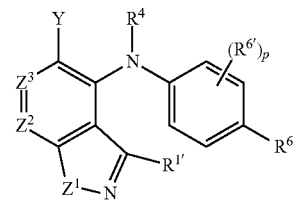

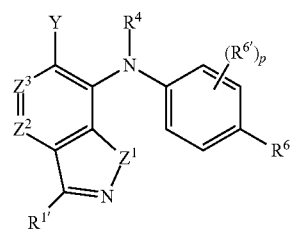

or a salt thereof, wherein:
$Z^1$ is NR$^1$ or S;
R$^1$ is H or C$_1$-C$_3$ alkyl;
R$^{1'}$ is H, C$_1$-C$_3$ alkyl, cyclopropyl, halo, CF$_3$, CHF$_2$, CN, NR$^A$R$^A$ or OR$^B$;
each R$^A$ is independently H or C$_1$-C$_3$ alkyl;
R$^B$ is H, or C$_1$-C$_3$ alkyl optionally substituted with one or more halo;
$Z^2$ is CR$^2$ or N;
$Z^3$ is CR$^3$;
R$^2$ and R$^3$ are independently selected from H, halo, CN, CF$_3$, —OCF$_3$, —NO$_2$, —(CR$^{14}$R$^{15}$)$_n$OR$^{11}$ or C$_1$-C$_{12}$ alkyl;
R$^4$ is H, C$_1$-C$_6$ alkyl or C$_3$-C$_4$ carbocyclyl;
Y is W—C(O)—;

W is

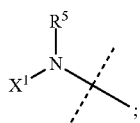

$R^5$ is H or $C_1$-$C_{12}$ alkyl;

$X^1$ is —$OR^{11'}$;

$R^{11'}$ is $C_1$-$C_{12}$ alkyl, tetrahydropyran-4-yl, piperidin-4-yl, piperidiny-3-yl, pyrrolidin-3-yl, azetidinyl-3-yl, 3-hydroxy-azetidin-3-yl, pyrrolidin-2-ylmethyl, 1H-imidazol-5-ylmethyl or 1H-imidazol-2-ylmethyl;

$R^{11}$ is H or $C_1$-$C_{12}$ alkyl;

$R^{14}$ and $R^{15}$ are H;

$R^6$ is halo, $C_2$-$C_8$ alkynyl, $C_3$-$C_5$ cycloalkyl or —$(CR^{19}R^{20})_n SR^{16}$;

each $R^{6'}$ is halo or $C_1$-$C_6$ alkyl;

p is 0, 1 or 2 or 3;

n is 0, 1, 2 or 3;

the alkyl group of $R^{11'}$ is optionally substituted with one or more $(CR^{19}R^{20})_n OR^{16}$ or $R^{21}$;

$R^{16}$ is hydrogen or $C_1$-$C_{12}$ alkyl;

$R^{19}$ and $R^{20}$ are H; and, $R^{21}$ is carbocyclyl.

2. The compound of claim 1 wherein:

$Z^1$ is N or S and $Z^2$ is $CR^2$ or N;

$R^2$ is H, methyl, $CF_3$, Cl, or F; and, $R^3$ is H, methyl, methoxy, $CF_3$, Cl, or F.

3. The compound of claim 2 wherein $Z^2$ is N.

4. The compound of claim 2 wherein $Z^2$ is $CR^2$.

5. The compound of claim 1 wherein:

$Z^1$ is N or S and $Z^2$ is $CR^2$; and, $R^2$ is H or F;

$R^3$ is H, methoxy, or F.

6. The compound of claim 2 wherein $X^1$ is selected from:

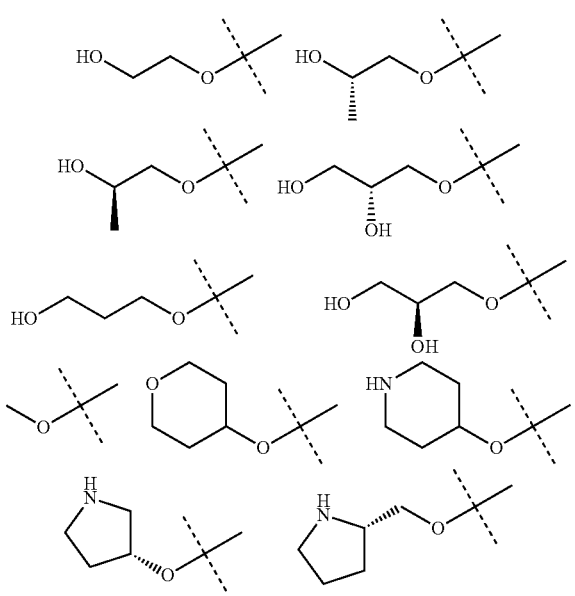

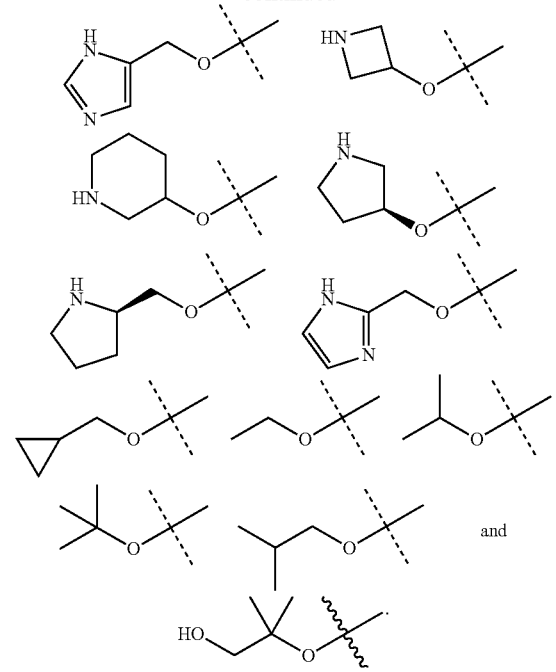

7. The compound of claim 6 wherein $R^6$ is selected from halo, —$SR^{16}$, $C_3$-$C_4$ cycloalkyl or $C_2$-$C_3$ alkynyl.

8. The compound of claim 7 wherein $R^6$ is I, Br, -SMe, $C_3$ cycloalkyl or $C_2$ alkynyl.

9. The compound of claim 8 wherein p is zero or one and when p is one $R^{6'}$ is selected from, halo or $C_1$-$C_3$ alkyl.

10. The compound of claim 9 wherein p is 1 and $R^{6'}$ is F or Cl.

11. The compound of claim 7 wherein p is zero or one and when p is one, $R^{6'}$ is halo or $C_1$-$C_3$ alkyl and $R^4$ is H or methyl.

12. The compound of claim 11 wherein $R^4$ is H.

13. The compound of claim 11 wherein $R^5$ is H or methyl.

14. The compound of claim 13 wherein $R^5$ is H.

15. A compound according to claim 1 selected from the group consisting of:

4-(2-fluoro-4-iodophenylamino)-1H-indazole-5-carboxylic acid (2-hydroxy-ethoxy)-amide;

4-(2-fluoro-4-iodophenylamino)-1H-pyrazolo[3,4-b]pyridine-5-carboxylic acid (2-hydroxyethoxy)-amide;

4-(2-fluoro-4-iodophenylamino)-1H-pyrazolo[3,4-b]pyridine-5-carboxylic acid ((S)2-hydroxypropoxy)-amide;

4-(2-Fluoro-4-iodophenylamino)-1H-pyrazolo[3,4-b]pyridine-5-carboxylic acid ((S)2-hydroxy-1,1-dimethylethoxy)-amide;

4-(2-fluoro-4-iodophenylamino)-1H-indazole-5-carboxylic acid ((R)-2,3-dihydroxy-propoxy)-amide;

4-(4-bromo-2-fluoro-phenylamino)-1H-indazole-5-carboxylic acid (2-hydroxy-ethoxy)-amide;

4-(4-bromo-2-fluoro-phenylamino)-1H-indazole-5-carboxylic acid ((S)-2-hydroxy-propoxy)-amide;

4-(2-fluoro-4-iodo-phenylamino)-benzo[d]isothiazole-5-carboxylic acid (2-hydroxy-ethoxy)-amide;

4-(2-fluoro-4-methylsulfanyl-phenylamino)-1H-indazole-5-carboxylic acid (2-hydroxy-ethoxy)-amide;

4-(2-fluoro-4-iodo-phenylamino)-1H-indazole-5-carboxylic acid ethoxy-amide;

4-(2-fluoro-4-iodo-phenylamino)-1H-indazole-5-carboxylic acid (tetrahydro-pyran-4-yloxy)-amide;

4-(2-fluoro-4-iodo-phenylamino)-1H-indazole-5-carboxylic acid cyclopropylmethoxy-amide;
4-(2-fluoro-4-iodo-phenylamino)-1H-indazole-5-carboxylic acid methoxy-amide;
4-(2-fluoro-4-iodo-phenylamino)-1H-indazole-5-carboxylic acid methoxy-methyl-amide;
4-(2-fluoro-4-iodo-phenylamino)-benzo[d]isothiazole-5-carboxylic acid ((S)-2-hydroxy-propoxy)-amide;
4-(2-fluoro-4-iodo-phenylamino)-benzo[d]isothiazole-5-carboxylic acid ((R)-2,3-dihydroxy-propoxy)-amide;
7-(2-fluoro-4-methylsulfanyl-phenylamino)-benzo[d]isothiazole-6-carboxylic acid ((R)-2,3-dihydroxy-propoxy)-amide;
7-(4-cyclopropyl-2-fluoro-phenylamino)-benzo[d]isothiazole-6-carboxylic acid ((R)-2,3-dihydroxy-propoxy)-amide;
7-(4-bromo-2-fluoro-phenylamino)-benzo[d]isothiazole-6-carboxylic acid ((R)-2,3-dihydroxy-propoxy)-amide;
7-(4-bromo-2-fluoro-phenylamino)-benzo[d]isothiazole-6-carboxylic acid (2-hydroxy-ethoxy)-amide;
7-(2-fluoro-4-iodo-phenylamino)-benzo[d]isothiazole-6-carboxylic acid (2-hydroxy-ethoxy)-amide; and,
7-(2-fluoro-4-iodo-phenylamino)-benzo[d]isothiazole-6-carboxylic acid ((R)-2,3-dihydroxy-propoxy)amide; or,
a pharmaceutically acceptable salt thereof.

16. A pharmaceutical composition comprising a compound of claim 1 and a pharmaceutically acceptable carrier.

17. The pharmaceutical composition of claim 16, further comprising a chemotherapeutic agent.

18. The pharmaceutical composition of claim 16, further comprising an anti-inflammatory agent.

19. The pharmaceutical composition of claim 16 wherein said chemotherapeutic agent is administered sequentially or consecutively.

* * * * *